(12) United States Patent
Stevenson et al.

(10) Patent No.: US 10,202,361 B2
(45) Date of Patent: Feb. 12, 2019

(54) PYRIDAZINONES AS HERBICIDES

(71) Applicant: E I DU PONT DE NEMOURS AND COMPANY, Wilmington, DE (US)

(72) Inventors: Thomas Martin Stevenson, Newark, DE (US); Matthew James Campbell, Rising Sun, MD (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 14/839,289

(22) Filed: Aug. 28, 2015

(65) Prior Publication Data

US 2016/0068509 A1   Mar. 10, 2016

Related U.S. Application Data

(60) Provisional application No. 62/043,651, filed on Aug. 29, 2014.

(51) Int. Cl.
  *C07D 401/06*   (2006.01)
  *A01N 43/58*    (2006.01)

(52) U.S. Cl.
  CPC .......... *C07D 401/06* (2013.01); *A01N 43/58* (2013.01)

(58) Field of Classification Search
  None
  See application file for complete search history.

(56) References Cited

U.S. PATENT DOCUMENTS

| | | | | |
|---|---|---|---|---|
| 5,670,504 A * | 9/1997 | Bochis | ......... | C07D 237/24 514/247 |
| 2010/0210649 A1* | 8/2010 | Djaballah | ......... | C07D 307/68 514/236.5 |
| 2010/0267561 A1 | 10/2010 | Stevenson et al. | | |
| 2013/0137661 A1 | 5/2013 | Kim et al. | | |

FOREIGN PATENT DOCUMENTS

| | | |
|---|---|---|
| DE | 4423934 A1 | 3/1995 |
| JP | 53012979 B * | 5/1978 |
| WO | 1996/25936 A1 | 8/1996 |
| WO | 2002/036576 A1 | 5/2002 |
| WO | 2011/062437 A2 | 5/2011 |
| WO | WO 2014/066164 | 5/2014 |
| WO | 2014/182950 A1 | 11/2014 |
| WO | 2015/168010 A1 | 11/2015 |
| WO | WO 2016/033285 | 3/2016 |

OTHER PUBLICATIONS

Lima, L. M.; Barreiro, E. J. "Bioisosterism: a useful strategy for molecular modification and drug design" Current Medicinal Chemistry, 2005, 12, 23-49.*
Del Olmo, Esther; et al. "Vasorelaxant activity of phthalazinones and related compounds" Bioorganic & Medicinal Chemistry Letters, 2006, v. 16, 2786-2790 (Year: 2006).*
Dovlatyan, V. V., et al., "Synthesis and Transformations of Chlorosubstituted azinyloxypyridazones", Hayastani Kimiakan Handes (2008), 61(2), 264-272.
Del Olmo E., et al., "Vasorelaxant activity of phthalazinones and related compounds", Bioorganic & Medicinal Chemistry Letters (2006), 16(10), 2786-2790.

* cited by examiner

Primary Examiner — Mina Haghighatian
Assistant Examiner — Erin E Hirt
(74) Attorney, Agent, or Firm — Reed A Coats

(57) ABSTRACT

Disclosed are compounds of Formula 1, including all stereoisomers, (N-oxides), and salts thereof,

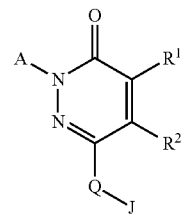

wherein A, $R^1$, $R^2$ Q and J are as defined in the disclosure. Also disclosed are compositions containing the compounds of Formula 1 and methods for controlling undesired vegetation comprising contacting the undesired vegetation or its environment with an effective amount of a compound or a composition of the invention.

12 Claims, No Drawings

PYRIDAZINONES AS HERBICIDES

FIELD OF THE INVENTION

This invention relates to certain pyridazinones, their N-oxides, salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY OF THE INVENTION

This invention is directed to a compound of Formula 1 (including all stereoisomers), N-oxides, and salts thereof, agricultural compositions containing them and their use as herbicides:

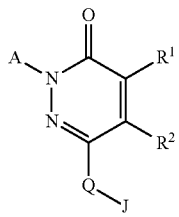

1 wherein
A is phenyl substituted with $R^3$; or a 5- or 6-membered heteroaromatic ring, said ring substituted with $R^4$ on carbon ring members and with $R^5$ on nitrogen ring members and attached to the remainder of Formula 1 through a carbon atom;
$R^1$ is H, halogen, cyano, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_6$ alkylcarbonyloxy, $C_1$-$C_4$ hydroxyalkyl, $SO_p(R^{16})$, $C_2$-$C_4$ alkylthioalkyl, $C_2$-$C_4$ alkylsulfonylalkyl, $C_1$-$C_4$ alkylamino, $C_2$-$C_4$ dialkylamino, $C_3$-$C_6$ cycloalkyl or hydroxy;
$R^2$ is H, halogen, cyano, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_6$ alkylcarbonyloxy, $C_1$-$C_4$ hydroxyalkyl, $SO_q(R^{17})$, $C_2$-$C_4$ alkylthioalkyl, $C_2$-$C_4$ alkylsulfonylalkyl, $C_1$-$C_4$ alkylamino, $C_2$-$C_4$ dialkylamino, $C_3$-$C_6$ cycloalkyl or hydroxy; or
$R^1$ and $R^2$ are taken together as $C_3$-$C_6$ alkylene or $C_3$-$C_6$ alkenylene;
Q is $C(R^6)(R^7)$, O, S or $NR^8$;
J is phenyl substituted with 1 $R^9$ and optionally substituted with up to 2 $R^{10}$; or
J is a 6-membered heteroaromatic ring substituted with 1 $R^9$ and optionally substituted with up to 2 $R^{10}$ on carbon ring members; or
J is a 5-membered heteroaromatic ring substituted with 1 $R^{11}$ on carbon ring members and $R^{13}$ on nitrogen ring members; and optionally substituted with 1 $R^{12}$ on carbon ring members;
each $R^3$ is independently H, halogen, cyano, nitro, $SF_5$, $C_1$-$C_4$ alkoxy, $C_1$-$C_4$ haloalkoxy, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy or $S(O)_rR^{18}$;
each $R^4$ is independently H, halogen, cyano, nitro, $C_1$-$C_4$ alkyl, $C_1$-$C_4$ haloalkyl, $C_1$-$C_4$ alkoxy, $C_1$-$C_4$ haloalkoxy or $S(O)_tR^{19}$;
$R^5$ is H, $C_1$-$C_4$ alkyl or $C_1$-$C_4$ haloalkyl;
$R^6$ is H, F, Cl, Br, cyano, $C_1$-$C_4$ alkyl, OH, $C_1$-$C_4$ haloalkyl, $OR^{14a}$ or $CO_2R^{15a}$;
$R^7$ is H, F, Cl, Br, cyano, $C_1$-$C_4$ alkyl, OH, $C_1$-$C_4$ haloalkyl, $OR^{14b}$ or $CO_2R^{15b}$; or
$R^6$ and $R^7$ are taken together with the carbon to which they both are attached to form C(=O), C(=$NOR^{24}$) or C(=N—N($R^{25}$)($R^{26}$));
$R^8$ is H, $C_1$-$C_4$ alkyl or $C_1$-$C_4$ haloalkyl;
$R^9$ is $SF_5$, $C_1$-$C_4$ haloalkyl, $C_1$-$C_4$ haloalkoxy or $S(O)_uR^{20}$;
each $R^{10}$ is independently halogen, cyano, $C_1$-$C_4$ alkyl, $C_1$-$C_4$ haloalkyl, $C_1$-$C_4$ alkoxy, $C_1$-$C_4$ haloalkoxy or $S(O)_vR^{21}$; or
$R^9$ and $R^{10}$ are taken together with two adjacent carbon atoms to form a 5-membered ring containing ring members selected from carbon atoms and up to two O atoms and up to two S atoms, and optionally substituted on carbon atom ring members with up to five halogen atoms;
$R^{11}$ is $SF_5$, $C_1$-$C_4$ haloalkyl, $C_1$-$C_4$ haloalkoxy or $S(O)_wR^{22}$;
$R^{12}$ is halogen, cyano, $C_1$-$C_4$ alkyl, $C_1$-$C_4$ haloalkyl, $C_1$-$C_4$ alkoxy, $C_1$-$C_4$ haloalkoxy or $S(O)_xR^{23}$;
$R^{13}$ is $C_1$-$C_4$ alkyl or $C_1$-$C_4$ haloalkyl;
each $R^{14a}$ and $R^{14b}$ is independently $C_1$-$C_4$ alkyl or $C_1$-$C_4$ haloalkyl; or
$R^{14a}$ and $R^{14b}$ are taken together as —$CH_2CH_2$— or —$CH_2CH_2CH_2$—;
each $R^{15a}$ and $R^{15b}$ is independently $C_1$-$C_4$ alkyl or $C_1$-$C_4$ haloalkyl;
each $R^{16}$, $R^{17}$, $R^{18}$, $R^{19}$, $R^{20}$, $R^{22}$ and $R^{23}$ is independently $C_1$-$C_4$ alkyl or $C_1$-$C_4$ haloalkyl;
$R^{21}$ is $C_1$-$C_4$ haloalkyl;
$R^{24}$ is H or $C_1$-$C_4$ alkyl;
$R^{25}$ is $C_1$-$C_4$ alkyl or $C_1$-$C_4$ haloalkyl;
$R^{26}$ is $C_1$-$C_4$ alkyl or $C_1$-$C_4$ haloalkyl; and
each p, q, r, t, u, v, w and x is independently 0, 1 or 2.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16).

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of carbon-bound substituent radicals specified for $R^1$ and $R^2$.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$ and the different butylene isomers. "Alkenylene" denotes a straight-chain or branched alkenediyl containing one olefinic bond. Examples of "alkenylene" include $CH=CH$, $CH_2CH=CH$, $CH=C(CH_3)$ and the different butenylene isomers. "Alkynylene" denotes a straight-chain or branched alkynediyl containing one triple bond. Examples of "alkynylene" include $C\equiv C$, $CH_2C\equiv C$, $C\equiv CCH_2$ and the different butynylene isomers.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" denotes a branched or straight-chain alkyl moiety attached through sulfur and includes methylthio, ethylthio, and the different propylthio and butylthio isomers. "Alkylsulfonyl" includes branched or straight-chain alkylsulfonyl moieties such as methylsulfonyl, ethylsulfonyl, and the different propylsulfonyl and butylsulfonyl isomers. Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. Examples of "Alkylsulfonylalkyl" includes $CH_3SO_2CH_2$, $CH_3SO_2CH_2CH_2$, $CH_3CH_2SO_2CH_2$, $CH_3CH_2CH_2CH_2SO_2CH_2$ and $CH_3CH_2SO_2CH_2CH_2$. "Hydroxyalkyl" denotes an alkyl group substituted with one hydroxy group. Examples of "hydroxyalkyl" include $HOCH_2$, $HOCH_2CH_2$ and $CH_3CH(OH)CH_2$. "Alkylamino", "dialkylamino", and the like, are defined analogously to the above examples. "Cycloalkyl" includes, for example, cyclopropyl, cyclobutyl, cyclopentyl and cyclohexyl. The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkoxy", and the like, are defined analogously to the term "haloalkyl". Examples of "haloalkoxy" include CF$_3$O—, CCl$_3$CH$_2$O—, HCF$_2$CH$_2$CH$_2$O— and CF$_3$CH$_2$O—.

"Alkylcarbonyl" denotes a straight-chain or branched alkyl moieties bonded to a C(=O) moiety. Examples of "alkylcarbonyl" include CH$_3$C(=O)—, CH$_3$CH$_2$CH$_2$C(=O)— and (CH$_3$)$_2$CHC(=O)—. Examples of "alkoxycarbonyl" include CH$_3$OC(=O)—, CH$_3$CH$_2$OC(=O)—, CH$_3$CH$_2$CH$_2$OC(=O)—, (CH$_3$)$_2$CHOC(=O)— and the different butoxy- or pentoxycarbonyl isomers. "Alkylcarbonyloxy" denotes an alkoxycarbonyl group bonded through oxygen. Examples of "alkoxycarbonyloxy" include CH$_3$OC(=O)O—, CH$_3$CH$_2$OC(=O)O—, CH$_3$CH$_2$CH$_2$OC(=O)O—, (CH$_3$)$_2$CHOC(=O)O— and the different butoxy- or pentoxycarbonyl isomers The total number of carbon atoms in a substituent group is indicated by the "C$_i$-C$_j$" prefix where i and j are numbers from 1 to 6. For example, C$_1$-C$_4$ alkylsulfonyl designates methylsulfonyl through butylsulfonyl; C$_2$ alkoxyalkyl designates CH$_3$OCH$_2$—; C$_3$ alkoxyalkyl designates, for example, CH$_3$CH(OCH$_3$)—, CH$_3$OCH$_2$CH$_2$— or CH$_3$CH$_2$OCH$_2$—; and C$_4$ alkoxyalkyl designates the various isomers of an alkyl group substituted with an alkoxy group containing a total of four carbon atoms, examples including CH$_3$CH$_2$CH$_2$OCH$_2$— and CH$_3$CH$_2$OCH$_2$CH$_2$—.

When a compound is substituted with a substituent bearing a subscript that indicates the number of said substituents can exceed 1, said substituents (when they exceed 1) are independently selected from the group of defined substituents, e.g., (R$^{10}$)$_n$, n is 1, 2, 3, 4 or 5). When a group contains a substituent which can be hydrogen, for example (R$^1$ or R$^2$), then when this substituent is taken as hydrogen, it is recognized that this is equivalent to said group being unsubstituted. When a variable group is shown to be optionally attached to a position, for example [R$^{12}$$_n$] wherein n may be 0, then hydrogen may be at the position even if not recited in the variable group definition. When one or more positions on a group are said to be "not substituted" or "unsubstituted", then hydrogen atoms are attached to take up any free valency.

Unless otherwise indicated, a "ring" or as a component of Formula 1 (e.g., substituent A or J) is carbocyclic or heterocyclic. The term "ring member" (e.g., when R$^9$ and R$^{10}$ are taken together) refers to an atom or other moiety (e.g., C(=O), C(=S), S(O) or S(O)$_2$) forming the backbone of a ring or ring system.

The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2)π electrons, where n is a positive integer, are associated with the ring to comply with Hückel's rule. The term "aromatic ring system" denotes a carbocyclic or heterocyclic ring system in which at least one ring of the ring system is aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

As noted above, A and J can be (among others) phenyl optionally substituted with one or more substituents selected from a group of substituents as defined in the Summary of the Invention. An example of phenyl optionally substituted with one to five substituents is the ring illustrated as U-1 in Exhibit 1, wherein R$^v$ is R$^3$ or R$^9$ as defined in the Summary of the Invention for A and J and r is an integer from 0 to 5.

As noted above, A and J can be (among others) a 5- or 6-membered heteroaromatic ring optionally substituted with one or more substituents selected from a group of substituents as defined in the Summary of the Invention. Examples of a 5- or 6-membered heteroaromatic ring optionally substituted with from one or more substituents include the rings U-2 through U-61 illustrated in Exhibit 1 wherein R$^v$ is any substituent as defined in the Summary of the Invention for A and J (i.e. R$^4$ or R$^9$, or R$^{11}$ or R$^{12}$) and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by (R$^v$)$_r$.

Exhibit 1

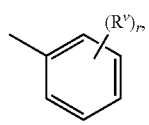

U-1

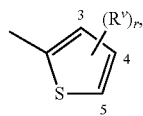

U-2

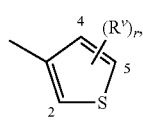

U-3

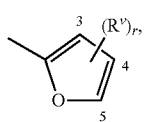
U-4
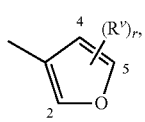
U-5
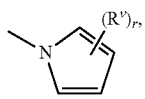
U-6
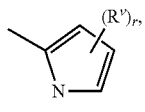
U-7
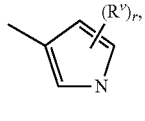
U-8
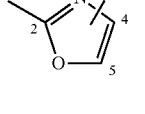
U-9
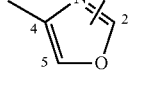
U-10
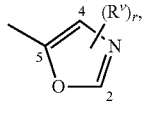
U-11
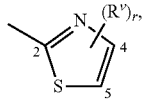
U-12
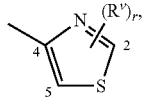
U-13
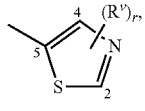
U-14
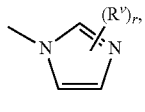
U-15
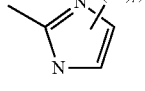
U-16
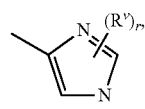
U-17
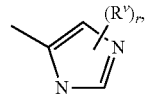
U-18
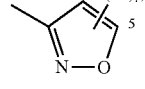
U-19
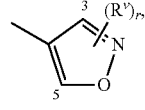
U-20
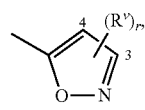
U-21
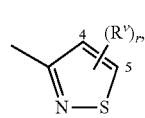
U-22
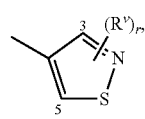
U-23
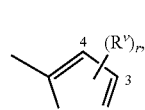
U-24
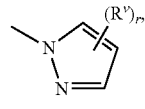
U-25
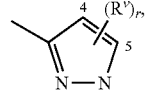
U-26
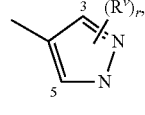
U-27
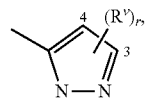
U-28
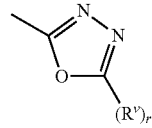
U-29

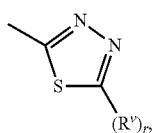 U-30
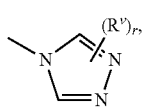 U-31
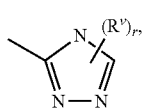 U-32
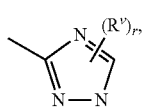 U-33
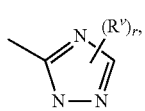 U-34
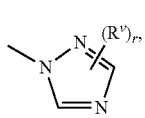 U-35
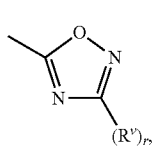 U-36
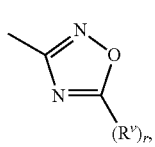 U-37
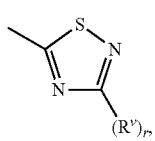 U-38
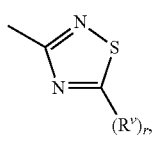 U-39
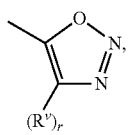 U-40
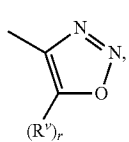 U-41
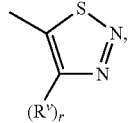 U-42
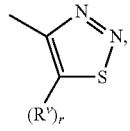 U-43
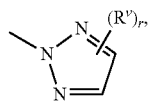 U-44
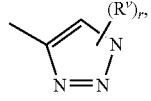 U-45
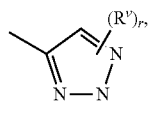 U-46
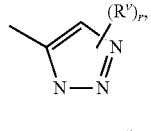 U-47
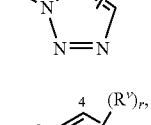 U-48
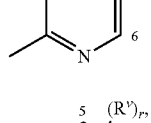 U-49
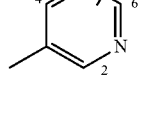 U-50
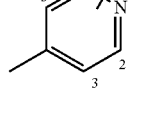 U-51
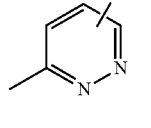 U-52
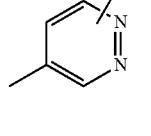 U-53

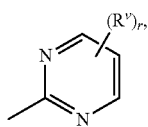 U-54

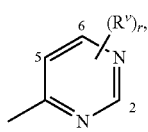 U-55

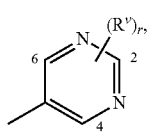 U-56

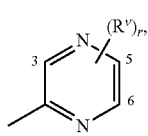 U-57

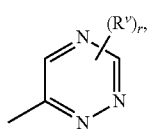 U-58

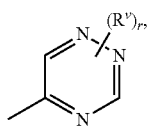 U-59

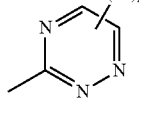 U-60 and

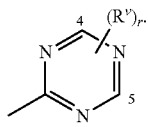 U-61.

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds of Formula 1 can comprise additional chiral centers. For example, substituents and other molecular constituents such as $R^2$ and $R^3$ may themselves contain chiral centers. This invention comprises racemic mixtures as well as enriched and essentially pure stereoconfigurations at these additional chiral centers.

Compounds of this invention can exist as one or more conformational isomers due to restricted rotation about the amide bond (e.g., when Q is $NR^8$) in Formula 1. This invention comprises mixtures of conformational isomers. In addition, this invention includes compounds that are enriched in one conformer relative to others.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M.

Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include (where Formula 1 as used in the following Embodiments includes N-oxides and salts thereof):

Embodiment 1

A compound of Formula 1 including all stereoisomers, N-oxides, and salts thereof, agricultural compositions containing them and their use as herbicides as described in the Summary of the Invention.

Embodiment 2

A compound of Embodiment 1 wherein A is phenyl substituted with $R^3$; or a 6-membered heteroaromatic ring, said ring substituted with $R^4$ on carbon ring members and with $R^5$ on nitrogen ring members and attached to the remainder of Formula 1 through a carbon atom.

Embodiment 3

A compound of Embodiment 1 or 2 wherein A is phenyl substituted with $R^3$.

Embodiment 4

A compound of Embodiment 3 wherein A is phenyl substituted with $R^3$ at the 3- or 4-position.

Embodiment 5

A compound of Embodiment 4 wherein A is phenyl substituted with $R^3$ at the 4-position.

Embodiment 5A

A compound of Embodiment 1 wherein A is phenyl optionally substituted with $R^3$; or a 6-membered heteroaromatic ring, said ring optionally substituted with $R^4$ on carbon ring members and with $R^5$ on nitrogen ring members and attached to the remainder of Formula 1 through a carbon atom.

Embodiment 5B

A compound of Embodiment 5A wherein A is phenyl optionally substituted with $R^3$.

Embodiment 5C

A compound of Embodiment 5A wherein A is phenyl substituted with $R^3$ only at the 3- or 4-position.

Embodiment 5D

A compound of Embodiment 5A wherein A is phenyl substituted with $R^3$ only at the 4-position.

Embodiment 5E

A compound of any one of Embodiments 1 through 5 wherein $R^1$ is H, halogen, cyano, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_1$-$C_4$ hydroxyalkyl, $SO_p(R^{16})$, $C_2$-$C_4$ alkylthioalkyl, $C_2$-$C_4$ alkylsulfonylalkyl, $C_1$-$C_4$ alkylamino, $C_2$-$C_4$ dialkylamino, $C_3$-$C_6$ cycloalkyl or hydroxy.

Embodiment 6

A compound of any one of Embodiments 1 through 5 wherein $R^1$ is H, halogen, cyano, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl or $C_2$-$C_4$ alkynyl.

Embodiment 7

A compound of Embodiment 6 wherein $R^1$ is H, $C_1$-$C_4$ alkyl or $C_1$-$C_4$ haloalkyl.

Embodiment 8

A compound of Embodiment 7 wherein $R^1$ is H or $C_1$-$C_4$ alkyl.

Embodiment 9

A compound of Embodiment 8 wherein $R^1$ is H or $CH_3$.

Embodiment 10

A compound of Embodiment 8 wherein $R^1$ is H.

Embodiment 10A

A compound of Embodiment 8 wherein $R^1$ is $CH_3$.

Embodiment 11

A compound of any one of Embodiments 1 through 10 wherein $R^2$ is H, halogen, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_6$ alkylcarbonyloxy, $C_1$-$C_4$ hydroxyalkyl, $SO_q$ ($R^{17}$), $C_2$-$C_4$ alkylthioalkyl, $C_2$-$C_4$ alkylsulfonylalkyl, $C_1$-$C_4$ alkylamino, $C_2$-$C_4$ dialkylamino or $C_3$-$C_6$ cycloalkyl.

Embodiment 12

A compound of Embodiment 11 wherein $R^2$ is H, $C_1$-$C_4$ alkoxy, $C_1$-$C_4$ haloalkoxy, $C_1$-$C_4$ alkyl, $C_1$-$C_4$ haloalkyl, $C_3$-$C_4$ alkenyloxy, $C_3$-$C_4$ alkynyloxy, $C_2$-$C_6$ alkylcarbonyloxy, $C_1$-$C_4$ alkylamino or $C_2$-$C_4$ dialkylamino.

Embodiment 13

A compound of Embodiment 12 wherein $R^2$ is $C_1$-$C_4$ alkoxy, $C_1$-$C_4$ alkyl or $C_2$-$C_4$ dialkylamino.

Embodiment 14

A compound of Embodiment 13 wherein $R^2$ is $C_1$-$C_4$ alkoxy or $C_1$-$C_4$ alkyl.

Embodiment 15

A compound of Embodiment 14 wherein $R^2$ is $C_1$-$C_4$ alkoxy.

Embodiment 16

A compound of Embodiment 15 wherein $R^2$ is —OCH$_2$CH$_3$ or —OCH$_3$.

Embodiment 17

A compound of Embodiment 15 wherein $R^2$ is —OCH$_2$CH$_3$.

Embodiment 18

A compound of Embodiment 14 wherein $R^2$ is $C_1$-$C_4$ alkyl.

Embodiment 19

A compound of Embodiment 18 wherein $R^2$ is CH$_3$ or CH$_2$CH$_3$.

Embodiment 20

A compound of Embodiment 18 wherein $R^2$ is CH$_3$.

Embodiment 21

A compound of any one of Embodiments 1 through 5 wherein $R^1$ and $R^2$ are taken together as $C_3$-$C_6$ alkylene.

Embodiment 22

A compound of Embodiments 21 wherein $R^1$ and $R^2$ are taken together as $C_4$ alkylene (i.e. —CH$_2$CH$_2$CH$_2$CH$_2$—).

Embodiment 22A

A compound of any one of Embodiments 1 through 20 wherein $R^1$ and $R^2$ are are taken alone (i.e. a compound of Embodiments 1 through 20 wherein $R^1$ and $R^2$ are other than taken together as $C_3$-$C_6$ alkylene or $C_3$-$C_6$ alkenylene).

Embodiment 22B

A compound of any one of Embodiments 1 through 22A wherein when $R^1$ is H, $R^2$ is other than H.

Embodiment 22C

A compound of any one of Embodiments 1 through 22 wherein when $R^2$ is H, $R^1$ is other than H.

Embodiment 22D

A compound of any one of Embodiments 1 through 22 wherein when $R^1$ is other than cyano.

Embodiment 22E

A compound of any one of Embodiments 1 through 22 wherein when $R^1$ is cyano, $R^2$ is other than CH$_3$.

Embodiment 23

A compound of any one of Embodiments 1 through 22 wherein Q is C($R^6$)($R^7$), O or S.

Embodiment 24

A compound of Embodiment 23 wherein Q is C($R^6$)($R^7$) or O.

Embodiment 25

A compound of Embodiment 23 wherein Q is C($R^6$)($R^7$).

Embodiment 26

A compound of Embodiment 23 wherein Q is S.

Embodiment 27

A compound of Embodiment 23 wherein Q is O.

Embodiment 28

A compound of any one of Embodiments 1 through 27 wherein J is selected from J-1 through J-33

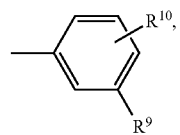

J-1

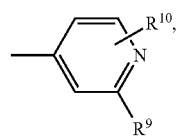

J-2

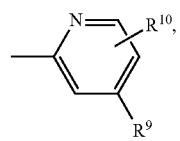

J-3

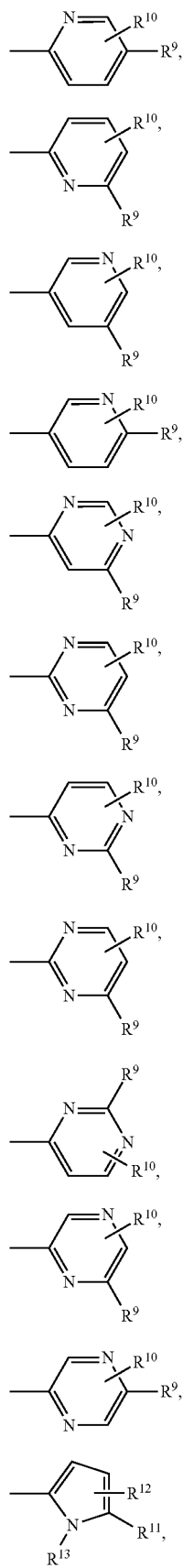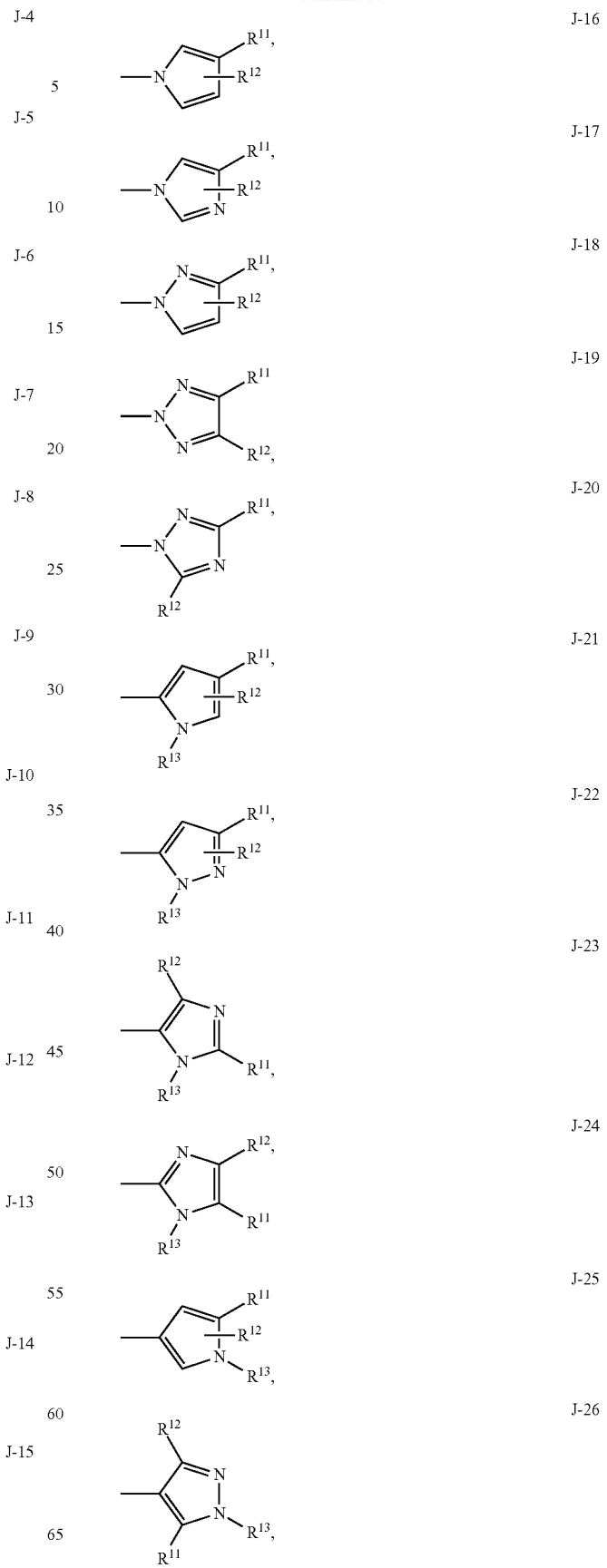

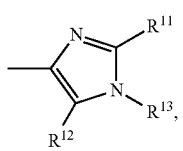 J-27
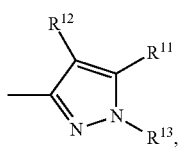 J-28
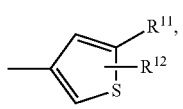 J-29
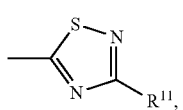 J-30
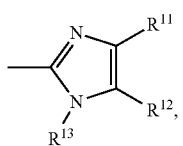 J-31
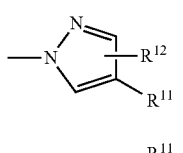 J-32
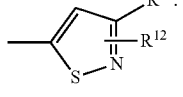 J-33
and
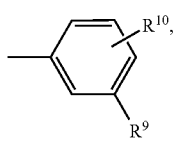
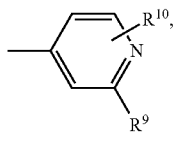
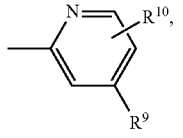
Embodiment 28A
A compound of any one of Embodiments 1 through 27 wherein J is selected from
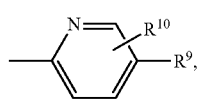 J-1
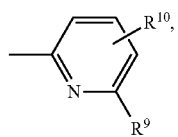 J-2
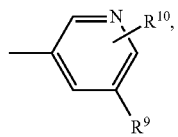 J-3
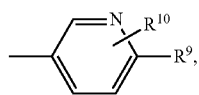 J-4
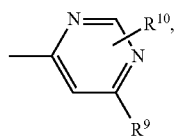 J-5
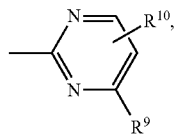 J-6
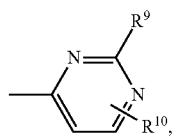 J-7
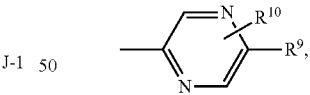 J-8
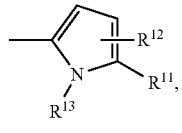 J-9
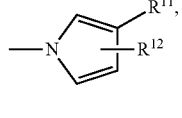 J-12
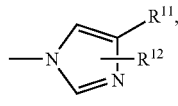 J-13
J-14
J-15
J-16
J-17

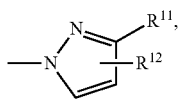 J-18

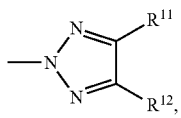 J-19

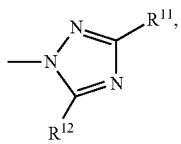 J-20

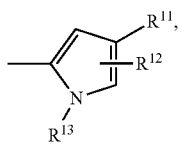 J-21

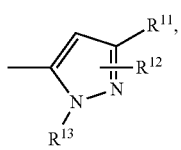 J-22

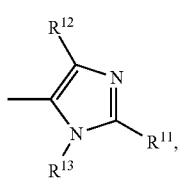 J-23

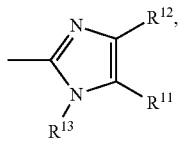 J-24

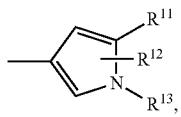 J-25

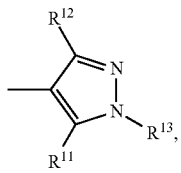 J-26

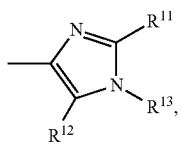 J-27

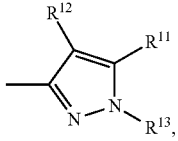 J-28

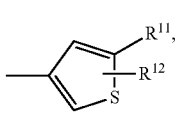 J-29

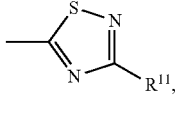 J-30

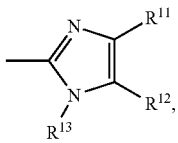 J-31

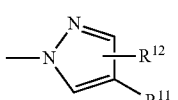 J-32 and

J-33

Embodiment 29

A compound of Embodiment 28 wherein J is selected from J-1 through J-14 (i.e. phenyl or a 6-membered heterocyclic ring).

Embodiment 30

A compound of Embodiment 28 wherein J is selected from J-15 through J-33 (i.e. a 5-membered heterocyclic ring).

Embodiment 31

A compound of Embodiment 28 wherein J is selected from J-1 and J-2.

Embodiment 32

A compound of Embodiment 31 wherein J is J-1.

Embodiment 33

A compound of Embodiment 31 wherein J is J-2.

Embodiment 34

A compound of Embodiment 32 wherein J is J-1 and $R^7$ is $CF_3$ (i.e. J is 3-trifluoromethylphenyl).

Embodiment 35

A compound of Embodiment 33 wherein J is J-2 and $R^7$ is $CF_3$ (i.e. J is 2-trifluoromethyl-4-pyridyl).

Embodiment 35A

A compound of Formula 1 wherein J is other than phenyl substituted with 1 $R^9$ and optionally substituted with up to 2 $R^{10}$.

Embodiment 35B

A compound of Formula 1 wherein J is a 6-membered aromatic heterocyclic ring substituted with 1 $R^9$ and optionally substituted with up to 2 $R^{10}$ on carbon ring members; or J is a 5-membered aromatic heterocyclic ring substituted with 1 $R^{11}$ on carbon ring members and $R^{13}$ on nitrogen ring members and optionally substituted with 1 $R^{12}$ on carbon ring members.

Embodiment 35C

A compound of any one of Embodiments 35A through 35B wherein J is selected from

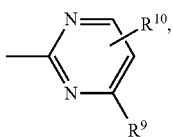
J-2

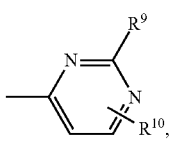
J-3

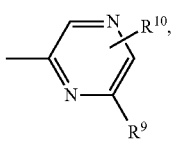
J-4

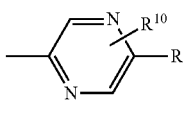
J-5

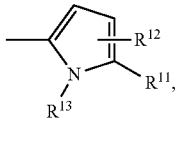
J-6

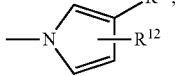
J-7

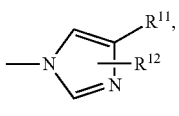
J-8

-continued

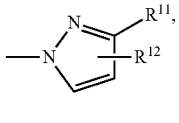
J-11

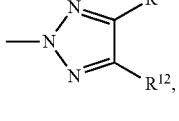
J-12

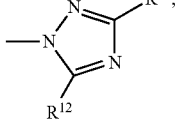
J-13

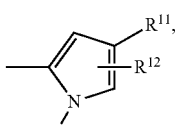
J-14

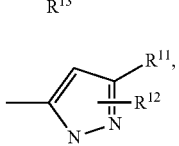
J-15

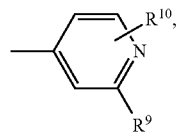
J-16

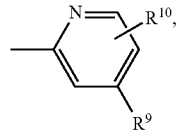
J-17

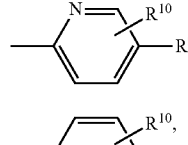
J-18

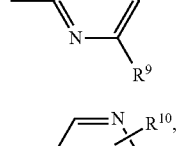
J-19

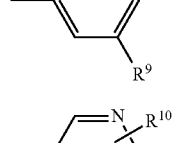
J-20

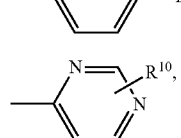
J-21

J-22

-continued

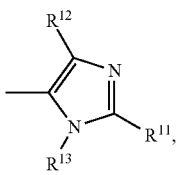
J-23

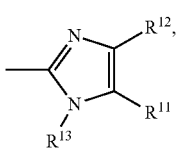
J-24

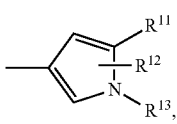
J-25

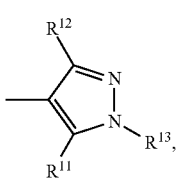
J-26

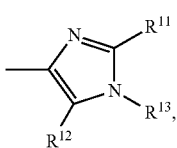
J-27

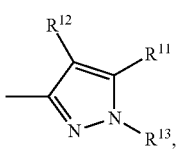
J-28

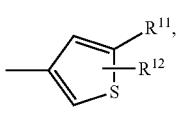
J-29

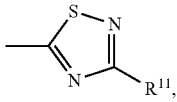
J-30

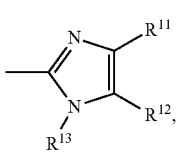
J-31

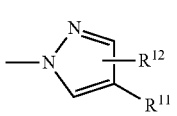
J-32 and

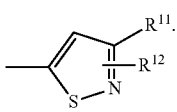
J-33

Embodiment 35D

A compound of Embodiment 35C wherein J is selected from J-2 through J-14 (i.e. a 6-membered heteroaromatic ring).

Embodiment 35E

A compound of Embodiment 35C wherein J is selected from J-15 through J-33 (i.e. a 5-membered heteroaromatic ring).

Embodiment 35F

A compound of Embodiment 35C wherein J is selected from J-2, J-3, J-4, J-5, J-6, J-7, J-9, J-12, J-17, J-18, J-20, J-22, J-26, J-29 and J-30.

Embodiment 35G

A compound of Embodiment 35C wherein J is selected from J-2, J-12, J-17, J-18, J-20 and J-22.

Embodiment 35H

A compound of Embodiment 35H wherein J is selected from J-2, J-20 and J-22.

Embodiment 35I

A compound of Embodiment 35H wherein J is J-2.

Embodiment 35J

A compound of Embodiment 35H wherein J is J-22.

Embodiment 35K

A compound of Embodiment 35H wherein J is J-2 and $R^7$ is $CF_3$.

Embodiment 35L

A compound of Formula 1 wherein J is other than a 1,3,5-triazen-2-yl substituted with 1 $R^9$ and optionally substituted with up to 1 $R^{10}$ on carbon ring members (e.g. U-61).

Embodiment 36

A compound of any one of Embodiments 1 through 35L wherein each $R^3$ is independently H, halogen, cyano, $C_1$-$C_4$ alkoxy, $C_1$-$C_4$ haloalkoxy, $C_1$-$C_4$ alkyl or $C_1$-$C_4$ haloalkyl.

Embodiment 37

A compound of Embodiment 36 wherein each $R^3$ is independently H, halogen or $C_1$-$C_4$ haloalkyl.

Embodiment 38

A compound of Embodiment 37 wherein $R^3$ is H, F, Cl, Br or $CF_3$.

Embodiment 39

A compound of Embodiment 38 wherein $R^3$ is H, F or $CF_3$.

Embodiment 39A

A compound of Formula 1 wherein when A is phenyl optionally substituted with $R^3$, each $R^3$ is independently halogen, cyano, $C_1$-$C_4$ alkoxy, $C_1$-$C_4$ haloalkoxy, $C_1$-$C_4$ alkyl or $C_1$-$C_4$ haloalkyl.

Embodiment 39B

A compound of Embodiment 39A wherein when A is phenyl optionally substituted with $R^3$, each $R^3$ is independently halogen or $C_1$-$C_4$ haloalkyl.

Embodiment 39C

A compound of Embodiment 39B wherein when A is phenyl optionally substituted with $R^3$, each $R^3$ is independently F, Cl, Br or $CF_3$.

Embodiment 39D

A compound of Embodiment 39C wherein when A is phenyl optionally substituted with $R^3$, each $R^3$ is independently F or $CF_3$.

Embodiment 40

A compound of any one of Embodiments 1 through 39 wherein each $R^4$ is independently H, halogen, nitro, $C_1$-$C_4$ alkyl, $C_1$-$C_4$ haloalkyl or $C_1$-$C_4$ alkoxy.

Embodiment 41

A compound of Embodiment 40 wherein each $R^4$ is independently H, halogen, $C_1$-$C_4$ alkyl, $C_1$-$C_4$ haloalkyl.

Embodiment 42

A compound of Embodiment 41 wherein each $R^4$ is independently H, F, Cl, Br, $CH_3$ or $CF_3$.

Embodiment 43

A compound of Embodiment 42 wherein each $R^4$ is independently H, F or $CF_3$.

Embodiment 43A

A compound of Formula 1 wherein when A is a 5- or 6-membered heteroaromatic ring, said ring optionally substituted with $R^4$ on carbon ring members, each $R^4$ is independently halogen, nitro, $C_1$-$C_4$ alkyl, $C_1$-$C_4$ haloalkyl or $C_1$-$C_4$ alkoxy.

Embodiment 43B

A compound of Embodiment 43A wherein when A is a 5- or 6-membered heteroaromatic ring, said ring optionally substituted with $R^4$ on carbon ring members, each $R^4$ is independently halogen, $C_1$-$C_4$ alkyl, $C_1$-$C_4$ haloalkyl.

Embodiment 43C

A compound of Embodiment 43A wherein when A is a 5- or 6-membered heteroaromatic ring, said ring optionally substituted with $R^4$ on carbon ring members, each $R^4$ is independently F, Cl, Br, $CH_3$ or $CF_3$.

Embodiment 43D

A compound of Embodiment 43A wherein when A is a 5- or 6-membered heteroaromatic ring, said ring optionally substituted with $R^4$ on carbon ring members, each $R^4$ is independently F or $CF_3$.

Embodiment 44

A compound of any one of Embodiments 1 through 43 wherein $R^5$ is H, halogen or $C_1$-$C_4$ haloalkyl.

Embodiment 45

A compound of Embodiment 44 wherein $R^5$ is H, $CH_3$ or $CH_2CF_3$.

Embodiment 46

A compound of any one of Embodiments 1 through 45 wherein $R^6$ is H, Cl or $C_1$-$C_4$ alkyl.

Embodiment 47

A compound of Embodiment 46 wherein $R^6$ is H, Cl or $CH_3$.

Embodiment 48

A compound of Embodiment 47 wherein $R^6$ is H or $CH_3$.

Embodiment 49

A compound of Embodiment 48 wherein $R^6$ is H.

Embodiment 50

A compound of Embodiment 48 wherein $R^6$ is $CH_3$.

Embodiment 51

A compound of any one of Embodiments 1 through 50 wherein $R^7$ is H, F, Cl, OH, $C_1$-$C_4$ haloalkyl, $OR^{14a}$ or $CO_2R^{15a}$.

Embodiment 52

A compound of Embodiment 51 wherein $R^7$ is H, OH or $OR^{14a}$.

Embodiment 53

A compound of Embodiment 52 wherein $R^7$ is H or OH.

Embodiment 54

A compound of Embodiment 53 wherein $R^7$ is H.

Embodiment 55

A compound of any one of Embodiments 1 through 45 wherein $R^6$ and $R^7$ are taken together with the carbon to which they both are attached to form C(=O).

Embodiment 56

A compound of Embodiment 1 wherein $R^8$ is H, $CH_3$ or $CH_2CF_3$.

Embodiment 57

A compound of Embodiment 56 wherein $R^8$ is H or $CH_3$.

Embodiment 58

A compound of any one of Embodiments 1 through 57 wherein $R^9$ is $C_1$-$C_4$ haloalkyl, $C_1$-$C_4$ haloalkoxy or $S(O)_u R^{20}$.

Embodiment 59

A compound of Embodiment 58 wherein $R^9$ is $CF_3$, $CH_2CF_3$, —$OCF_3$ or —$SCF_3$.

Embodiment 60

A compound of Embodiment 59 wherein $R^9$ is $CF_3$.

Embodiment 61

A compound of any one of Embodiments 1 through 60 wherein each $R^{10}$ is independently halogen, $C_1$-$C_4$ alkyl or $C_1$-$C_4$ haloalkyl.

Embodiment 62

A compound of Embodiment 61 wherein each $R^{10}$ is independently Cl, F or $CH_3$.

Embodiment 63

A compound of Embodiment 62 wherein each $R^{10}$ is independently F.

Embodiment 64

A compound of any one of Embodiments 1 through 57 wherein $R^9$ and $R^{10}$ (i.e. $R^{10}$ is present) are taken together with two adjacent carbon atoms to form a 5-membered ring containing ring members selected from carbon atoms and two O atoms, and optionally substituted on carbon atom ring members with up to 2 halogen atoms.

Embodiment 65

A compound of any one of Embodiments 1 through 64 wherein $R^{11}$ is $C_1$-$C_4$ haloalkyl, $C_1$-$C_4$ haloalkoxy or $S(O)_w R^{22}$.

Embodiment 66

A compound of Embodiment 65 wherein $R^{11}$ is $CF_3$, $CH_2CF_3$, —$OCF_3$ or —$SCF_3$.

Embodiment 67

A compound of Embodiment 66 wherein $R^{11}$ is $CF_3$.

Embodiment 68

A compound of any one of Embodiments 1 through 67 wherein $R^{12}$ is halogen, $C_1$-$C_4$ alkyl or $C_1$-$C_4$ haloalkyl.

Embodiment 69

A compound of Embodiment 68 wherein $R^{12}$ is Cl, $CH_3$ or $CF_3$.

Embodiment 70

A compound of Embodiment 69 wherein $R^{12}$ is $CF_3$.

Embodiment 71

A compound of any one of Embodiments 1 through 70 wherein $R^{13}$ is H, $CH_3$ or $CH_2CF_3$.

Embodiment 72

A compound of Embodiment 71 wherein $R^{13}$ is H or $CH_3$.

Embodiment 73

A compound of Embodiment 72 wherein $R^{13}$ is $CH_3$.

Embodiment 74

A compound of any one of Embodiments 1 through 73 wherein each $R^{14a}$ and $R^{14b}$ is independently $C_1$-$C_4$ alkyl.

Embodiment 75

A compound of Embodiment 74 wherein each $R^{14a}$ and $R^{14b}$ is independently $CH_3$.

Embodiment 76

A compound of any one of Embodiments 1 through 75 wherein each $R^{15a}$ and $R^{15b}$ is independently $C_1$-$C_4$ alkyl.

Embodiment 77

A compound of Embodiment 76 wherein each $R^{15a}$ and $R^{15b}$ is independently $CH_3$.

Embodiment 78

A compound of any one of Embodiments 1 through 77 wherein each $R^{17}$, $R^{20}$ and $R^{22}$ is independently $C_1$-$C_4$ alkyl.

Embodiment 79

A compound of any one of Embodiments 1 through 78 wherein $R^{21}$ is $CF_3$.

Embodiment 80

A compound of any one of Embodiments 77 or 79 wherein each q, u, w and x is independently 0 or 2.

Embodiments of this invention, including Embodiments 1-80 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-80 above as well as any other embodiments described herein, and any combination thereof, pertain to the compositions and methods of the present invention.

Combinations of Embodiments 1-80 are illustrated by:

Embodiment A

A compound of Formula 1 as described in the Summary of the Invention wherein

A is phenyl substituted with $R^3$; or a 6-membered heteroaromatic ring, said ring substituted with $R^4$ on carbon ring members and with $R^5$ on nitrogen ring members and attached to the remainder of Formula 1 through a carbon atom;

$R^1$ is H, halogen, cyano, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl or $C_2$-$C_4$ alkynyl;

$R^2$ is H, halogen, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_6$ alkylcarbonyloxy, $C_1$-$C_4$ hydroxyalkyl, $SO_q(R^{17})$, $C_2$-$C_4$ alkylthioalkyl, $C_2$-$C_4$ alkylsulfonylalkyl, $C_1$-$C_4$ alkylamino, $C_2$-$C_4$ dialkylamino or $C_3$-$C_6$ cycloalkyl; or $R^1$ and $R^2$ are taken together as $C_3$-$C_6$ alkylene;

Q is $C(R^6)(R^7)$, O or S;

J is independently selected from J-1 through J-33;

each $R^3$ is independently H, halogen, cyano, $C_1$-$C_4$ alkoxy, $C_1$-$C_4$ haloalkoxy, $C_1$-$C_4$ alkyl or $C_1$-$C_4$ haloalkyl;

each $R^4$ is independently H, halogen, nitro, $C_1$-$C_4$ alkyl, $C_1$-$C_4$ haloalkyl or $C_1$-$C_4$ alkoxy;

$R^5$ is H, halogen or $C_1$-$C_4$ haloalkyl;

$R^6$ is H, Cl or $C_1$-$C_4$ alkyl;

$R^7$ is H, F, Cl, OH, $C_1$-$C_4$ haloalkyl, $OR^{14b}$ or $CO_2R^{15b}$; or $R^6$ and $R^7$ are taken together with the carbon to which they both are attached to form $C(=O)$;

$R^9$ is $C_1$-$C_4$ haloalkyl, $C_1$-$C_4$ haloalkoxy or $S(O)_uR^{20}$;

each $R^{10}$ is independently halogen, $C_1$-$C_4$ alkyl or $C_1$-$C_4$ haloalkyl; or $R^9$ and $R^{10}$ are taken together with two adjacent carbon atoms to form a 5-membered ring containing ring members selected from carbon atoms and two O atoms, and optionally substituted on carbon atom ring members with up to 2 halogen atoms;

$R^{11}$ is $C_1$-$C_4$ haloalkyl, $C_1$-$C_4$ haloalkoxy or $S(O)_wR^{22}$;

$R^{12}$ is halogen, $C_1$-$C_4$ alkyl or $C_1$-$C_4$ haloalkyl;

$R^{13}$ is H, $CH_3$ or $CH_2CF_3$;

each $R^{14b}$ is independently $C_1$-$C_4$ alkyl;

each $R^{15b}$ is independently $C_1$-$C_4$ alkyl;

each $R^{17}$, $R^{20}$ and $R^{22}$ is independently $C_1$-$C_4$ alkyl;

$R^{21}$ is $CF_3$; and each q, u, w and x is independently 0 or 2.

Embodiment A1

A compound of Formula 1 as described in the Summary of the Invention wherein

A is phenyl optionally substituted with $R^3$; or a 6-membered heteroaromatic ring, said ring substituted optionally with $R^4$ on carbon ring members and with $R^5$ on nitrogen ring members and attached to the remainder of Formula 1 through a carbon atom;

$R^1$ is H, halogen, cyano, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl or $C_2$-$C_4$ alkynyl;

$R^2$ is H, halogen, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_6$ alkylcarbonyloxy, $C_1$-$C_4$ hydroxyalkyl, $SO_q(R^{17})$, $C_2$-$C_4$ alkylthioalkyl, $C_2$-$C_4$ alkylsulfonylalkyl, $C_1$-$C_4$ alkylamino, $C_2$-$C_4$ dialkylamino or $C_3$-$C_6$ cycloalkyl; or $R^1$ and $R^2$ are taken together as $C_3$-$C_6$ alkylene;

Q is $C(R^6)(R^7)$, O or S;

J is independently selected from J-1 through J-33;

each $R^3$ is independently halogen, cyano, $C_1$-$C_4$ alkoxy, $C_1$-$C_4$ haloalkoxy, $C_1$-$C_4$ alkyl or $C_1$-$C_4$ haloalkyl;

each $R^4$ is independently halogen, nitro, $C_1$-$C_4$ alkyl, $C_1$-$C_4$ haloalkyl or $C_1$-$C_4$ alkoxy;

$R^5$ is H, halogen or $C_1$-$C_4$ haloalkyl;

$R^6$ is H, Cl or $C_1$-$C_4$ alkyl;

$R^7$ is H, F, Cl, OH, $C_1$-$C_4$ haloalkyl, $OR^{14b}$ or $CO_2R^{15b}$; or $R^6$ and $R^7$ are taken together with the carbon to which they both are attached to form $C(=O)$;

$R^9$ is $C_1$-$C_4$ haloalkyl, $C_1$-$C_4$ haloalkoxy or $S(O)_uR^{20}$;

each $R^{10}$ is independently halogen, $C_1$-$C_4$ alkyl or $C_1$-$C_4$ haloalkyl; or $R^9$ and $R^{10}$ are taken together with two adjacent carbon atoms to form a 5-membered ring containing ring members selected from carbon atoms and two O atoms, and optionally substituted on carbon atom ring members with up to 2 halogen atoms;

$R^{11}$ is $C_1$-$C_4$ haloalkyl, $C_1$-$C_4$ haloalkoxy or $S(O)_wR^{22}$;

$R^{12}$ is halogen, $C_1$-$C_4$ alkyl or $C_1$-$C_4$ haloalkyl;

$R^{13}$ is H, $CH_3$ or $CH_2CF_3$;

each $R^{14b}$ is independently $C_1$-$C_4$ alkyl;

each $R^{15b}$ is independently $C_1$-$C_4$ alkyl;

each $R^{17}$, $R^{20}$ and $R^{22}$ is independently $C_1$-$C_4$ alkyl;

$R^{21}$ is $CF_3$; and each q, u, w and x is independently 0 or 2.

Embodiment B

A compound of Embodiment A wherein

A is phenyl substituted with $R^3$;

$R^1$ is H, $C_1$-$C_4$ alkyl or $C_1$-$C_4$ haloalkyl;

$R^2$ is H, $C_1$-$C_4$ alkoxy, $C_1$-$C_4$ haloalkoxy, $C_1$-$C_4$ alkyl, $C_1$-$C_4$ haloalkyl, $C_3$-$C_4$ alkenyloxy, $C_3$-$C_4$ alkynyloxy, $C_2$-$C_6$ alkylcarbonyloxy, $C_1$-$C_4$ alkylamino or $C_2$-$C_4$ dialkylamino; or $R^1$ and $R^2$ are taken together as $C_4$ alkylene;

Q is $C(R^6)(R^7)$ or O;

J is selected from J-1 through J-14 (i.e. phenyl or a 6-membered heterocyclic ring);

each $R^3$ is independently H, halogen or $C_1$-$C_4$ haloalkyl;

each $R^4$ is independently H, halogen, $C_1$-$C_4$ alkyl, $C_1$-$C_4$ haloalkyl;

$R^6$ is H, Cl or $CH_3$;

$R^7$ is H, OH or $OR^{14b}$;

$R^9$ is $CF_3$, $CH_2CF_3$, $-OCF_3$ or $-SCF_3$; and each $R^{10}$ is independently Cl, F or $CH_3$.

Embodiment B1

A compound of Embodiment A1 wherein

A is phenyl optionally substituted with $R^3$;

$R^1$ is H, $C_1$-$C_4$ alkyl or $C_1$-$C_4$ haloalkyl;

$R^2$ is H, $C_1$-$C_4$ alkoxy, $C_1$-$C_4$ haloalkoxy, $C_1$-$C_4$ alkyl, $C_1$-$C_4$ haloalkyl, $C_3$-$C_4$ alkenyloxy, $C_3$-$C_4$ alkynyloxy, $C_2$-$C_6$ alkylcarbonyloxy, $C_1$-$C_4$ alkylamino or $C_2$-$C_4$ dialkylamino; or $R^1$ and $R^2$ are taken together as $C_4$ alkylene;

Q is $C(R^6)(R^7)$ or O;

J is selected from J-1 through J-14 (i.e. phenyl or a 6-membered heterocyclic ring);

each $R^3$ is independently halogen or $C_1$-$C_4$ haloalkyl;

$R^6$ is H, Cl or $CH_3$;

$R^7$ is H, OH or $OR^{14b}$;

$R^9$ is $CF_3$, $CH_2CF_3$, $-OCF_3$ or $-SCF_3$; and each $R^{10}$ is independently Cl, F or $CH_3$.

Embodiment C

A compound of Embodiment A wherein
$R^1$ is H or $C_1$-$C_4$ alkyl;
$R^2$ is $C_1$-$C_4$ alkoxy, $C_1$-$C_4$ alkyl or $C_2$-$C_4$ dialkylamino;
Q is O;
J is selected from J-1 and J-2;
each $R^3$ is H, F, Cl, Br or $CF_3$;
each $R^4$ is independently H, F, Cl, Br, $CH_3$ or $CF_3$;
$R^9$ is $CF_3$; and
each $R^{10}$ is independently F.

Embodiment C

A compound of Embodiment A wherein
$R^1$ is H or $C_1$-$C_4$ alkyl;
$R^2$ is $C_1$-$C_4$ alkoxy, $C_1$-$C_4$ alkyl or $C_2$-$C_4$ dialkylamino;
Q is O;
J is selected from J-1 and J-2;
each $R^3$ is F, Cl, Br or $CF_3$;
$R^9$ is $CF_3$; and
each $R^{10}$ is independently F.

Embodiment D

A compound of Embodiment C wherein
$R^1$ is H or $CH_3$;
$R^2$ is $C_1$-$C_4$ alkoxy;
Q is $C(R^6)(R^7)$;
$R^6$ is H, Cl or $CH_3$; and
$R^7$ is H or OH.

Embodiment E

A compound of Embodiment A wherein
A is phenyl substituted with $R^3$;
$R^1$ is H, $C_1$-$C_4$ alkyl or $C_1$-$C_4$ haloalkyl;
$R^2$ is H, $C_1$-$C_4$ alkoxy, $C_1$-$C_4$ haloalkoxy, $C_1$-$C_4$ alkyl, $C_1$-$C_4$ haloalkyl, $C_3$-$C_4$ alkenyloxy, $C_3$-$C_4$ alkynyloxy, $C_2$-$C_6$ alkylcarbonyloxy, $C_1$-$C_4$ alkylamino or $C_2$-$C_4$ dialkylamino; or
$R^1$ and $R^2$ are taken together as $C_4$ alkylene;
Q is $C(R^6)(R^7)$ or O;
J is selected from J-15 through J-33;
$R^6$ is H, Cl or $CH_3$;
$R^7$ is H, OH or $OR^{14b}$;
$R^{11}$ is $CF_3$, $CH_2CF_3$, $-OCF_3$ or $-SCF_3$;
$R^{12}$ is Cl, $CH_3$ or $CF_3$;
$R^{13}$ is H or $CH_3$;
$R^{14b}$ is $CH_3$; and
$R^{15b}$ is $CH_3$.

Embodiment E1

A compound of Embodiment A wherein
A is phenyl optionally substituted with $R^3$;
$R^1$ is H, $C_1$-$C_4$ alkyl or $C_1$-$C_4$ haloalkyl;
$R^2$ is H, $C_1$-$C_4$ alkoxy, $C_1$-$C_4$ haloalkoxy, $C_1$-$C_4$ alkyl, $C_1$-$C_4$ haloalkyl, $C_3$-$C_4$ alkenyloxy, $C_3$-$C_4$ alkynyloxy, $C_2$-$C_6$ alkylcarbonyloxy, $C_1$-$C_4$ alkylamino or $C_2$-$C_4$ dialkylamino; or
$R^1$ and $R^2$ are taken together as $C_4$ alkylene;
Q is $C(R^6)(R^7)$ or O;
J is selected from J-15 through J-33;
$R^6$ is H, Cl or $CH_3$;
$R^7$ is H, OH or $OR^{14b}$;
$R^{11}$ is $CF_3$, $CH_2CF_3$, $-OCF_3$ or $-SCF_3$;
$R^{12}$ is Cl, $CH_3$ or $CF_3$;
$R^{13}$ is H or $CH_3$;
$R^{14b}$ is $CH_3$; and
$R^{15b}$ is $CH_3$.

Embodiment F

A compound of Embodiment E wherein
$R^1$ is H or $C_1$-$C_4$ alkyl
$R^2$ is $C_1$-$C_4$ alkoxy, $C_1$-$C_4$ alkyl or $C_2$-$C_4$ dialkylamino;
Q is $C(R^6)(R^7)$;
J is selected from J-1 and J-2;
each $R^3$ is H, F, Cl, Br or $CF_3$;
each $R^4$ is independently H, F, Cl, Br, $CH_3$ or $CF_3$;
$R^6$ is H or $CH_3$;
$R^7$ is H or OH;
$R^9$ is $CF_3$; and
each $R^{10}$ is independently F.

Embodiment F1

A compound of Embodiment E1 wherein
$R^1$ is H or $C_1$-$C_4$ alkyl
$R^2$ is $C_1$-$C_4$ alkoxy, $C_1$-$C_4$ alkyl or $C_2$-$C_4$ dialkylamino;
Q is $C(R^6)(R^7)$;
J is selected from J-1 and J-2;
each $R^3$ is F, Cl, Br or $CF_3$;
$R^6$ is H or $CH_3$;
$R^7$ is H or OH;
$R^9$ is $CF_3$; and
each $R^{10}$ is independently F.

Embodiment G

A compound of Embodiment F wherein
$R^1$ is H or $CH_3$;
$R^2$ is $C_1$-$C_4$ alkoxy;
$R^3$ is H, F or $CF_3$;
$R^6$ is H; and
$R^7$ is H or OH.

Embodiment G1

A compound of Embodiment F1 wherein
$R^1$ is H or $CH_3$;
$R^2$ is $C_1$-$C_4$ alkoxy;
$R^3$ is F or $CF_3$;
$R^6$ is H; and
$R^7$ is H or OH.

Specific Embodiments include a compound of Formula 1 selected from the group consisting of
2-(4-fluorophenyl)-5-methyl-6-[[2-(trifluoromethyl)-4-pyridinyl]methyl]-3 (2H)-pyridazinone (Compound 1);
5-methyl-2-[4-(trifluoromethyl)phenyl]-6-[[2-(trifluoromethyl)-4-pyridinyl]methyl]-3(2H)-pyridazinone (Compound 2);
4-methyl-2-[4-(trifluoromethyl)phenyl]-6-[[2-(trifluoromethyl)-4-pyridinyl]oxy]-3(2H)-pyridazinone (Compound 6);
2-(4-fluorophenyl)-5-methyl-6-[[2-(trifluoromethyl)-4-pyridinyl]oxy]-3 (2H)-pyridazinone (Compound 14);
5-methoxy-2-[4-(trifluoromethyl)phenyl]-6-[[2-(trifluoromethyl)-4-pyridinyl]methyl]-3(2H)-pyridazinone (Compound 16);

2-(4-fluorophenyl)-5-methoxy-6-[[2-(trifluoromethyl)-4-pyridinyl]methyl]-3 (2H)-pyridazinone (Compound 17);

5-ethoxy-2-(4-fluorophenyl)-6-[hydroxy[2-(trifluoromethyl)-4-pyridinyl]methyl]-3(2H)-pyridazinone (Compound 23); and 5-ethoxy-2-(4-fluorophenyl)-6-[[2-(trifluoromethyl)-4-pyridinyl]methyl]-3 (2H)-pyridazinone (Compound 25).

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenzmethyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-

2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate) and 3-[7-fluoro-3,4-dihydro-3-oxo-4-(2-propyn-1-yl)-2H-1,4-benzoxazin-6-yl]dihydro-1,5-dimethyl-6-thioxo-1,3,5-triazine-2,4(1H,3H)-dione.

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, napropanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenyl-pyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3 (2H)-pyridazinone, 4-(4-fluorophenyl)-6-[(2-hydroxy-6-oxo-1-cyclohexen-1-yl)carbonyl]-2-methyl-1,2,4-triazine-3,5 (2H,4H)-dione, 5-[(2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

"HST inhibitors" (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, 3-(2-chloro-3,6-difluorophenyl)-4-hydroxy-1-methyl-1,5-naphthyridin-2 (1H)-one, 7-(3,5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3 (2H)-pyridazinone.

HST inhibitors also include compounds of Formulae A and B.

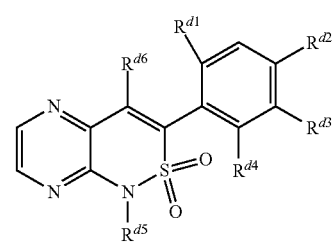

A

B

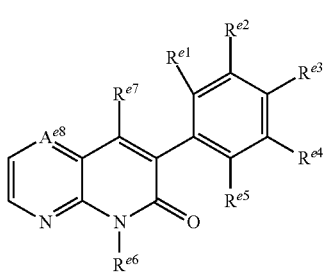

wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(=O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(=O)Et, —OC(=O)-i-Pr or —OC(=O)-t-Bu; and $A^{e8}$ is N or CH.

"Cellulose biosynthesis inhibitors" (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, cyclopyrimorate (6-chloro-3-(2-cyclopropyl-6-methylphenoxy)-4-pyridazinyl 4-morpholinecarboxylate), daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660).

The compounds of Formula 1 can be prepared by general methods known in the art of synthetic organic chemistry. One or more of the following methods and variations as described in Schemes X can be used to prepare the compounds of Formula 1. The definitions of A, Q, J, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ in the compounds of Formulae 1 through 28 below are as defined above in the Summary of the Invention unless otherwise noted. Compounds of Formulae 1a, 1b, 1c, 1d, 1e, 1f, 4a, 4b, 7a, 12a, 12b and 12c are various subsets of Formulae 1, 4, 7 and 12, respectively. All substituents for compounds of Formulae 1a-1f are as defined above for Formula 1 unless otherwise noted.

Compounds of Formula 1a, 1b or 1c (i.e. wherein Q is O, S or $NR^8$, respectively) can be synthesized from a compound of Formula 2 by the reaction shown in Scheme 1 of an electron-deficient aromatic or heteroaromatic compound of Formula 3 wherein X is a suitable carbon-bound leaving group, for example, a halogen, sulfonate or alkoxide, in the presence of an appropriate base such as potassium carbonate, cesium carbonate or potassium hydroxide. Typically the reaction is conducted in a polar aprotic solvent such as dimethylsulfoxide, N,N-dimethylformamide, N,N-dimethylacetamide, N-methylpyrrolidinone or acetonitrile at temperatures ranging from ambient temperature to the reflux temperature of the solvent. A compound of Formula 3 is commercially available or its preparation is known in the art. For reaction conditions for this general coupling methodology, see Carey, F. A.; Sundberg, R. J., *Advanced Organic Chemistry Part B, 4th Edition*; Kluwer Academic/Plenum Publishers, New York, 2001; Chapter 11.2.2 and references cited therein.

Scheme 1

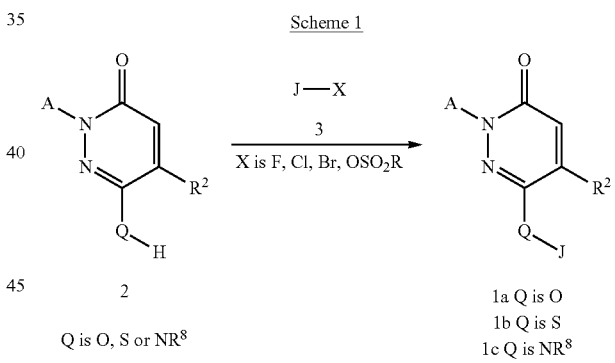

Q is O, S or $NR^8$

1a Q is O
1b Q is S
1c Q is $NR^8$

Compounds of Formulae 1d or 1e (i.e. wherein Q is $CH_2$ or C=O, respectively) can be synthesized from a compound of Formula 4 by the reaction shown in Scheme 2. Benzyl halides of Formula 4 are reacted with a suitable boronic acid or boronate ester of Formula 5 in the presence of a palladium salt or complex such as palladium(II) acetate, tetrakis(triphenylphosphine)palladium(0) or bis(triphenylphosphine)palladium(II) chloride, an appropriate ligand and an inorganic base such as potassium phosphate, potassium carbonate or sodium carbonate. Typically the reaction is conducted in a mixture of a solvent such as 1,2-dimethoxyethane, 1,4-dioxane, toluene, tetrahydrofuran or t-butanol and water at temperatures ranging from ambient temperature to the reflux temperature of the solvent. Typical procedures using benzyl bromides are disclosed in *Eur. J. Chem.* 2011, 46(2), 488-496 and in PCT Patent publication WO 2012/004714. A typical procedure using a benzyl chloride is disclosed in *Angew. Chem. Int. Ed.* 2011, 50(46), 10913-

10916. A compound of Formula 5 is commercially available or its preparation is known in the art.

Scheme 2

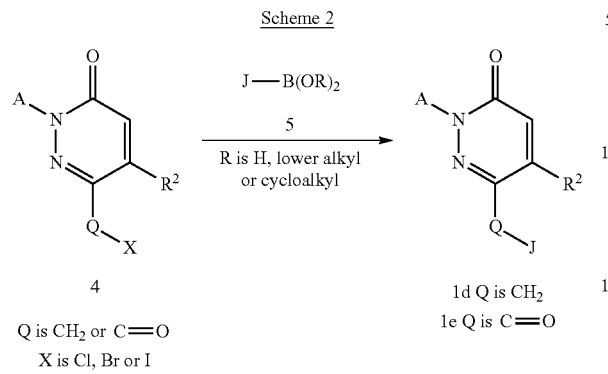

Compounds of Formulae 1d and 1e can alternatively be synthesized from a compound of Formula 4 by the reaction shown in Scheme 3. Benzyl halides or acid halides, typically acid chlorides, of Formula 4 are reacted with a suitable organozinc halide of Formula 6a or diorganozinc of Formula 6b in the presence of a palladium, nickel or copper salt or complex such as palladium(II) acetate, tetrakis(triphenylphosphine)palladium(0), bis(triphenylphosphine)palladium(II) chloride, nickel(II) chloride, nickel(II) bromide, nickel(II) acetoacetate, bis(tricyclohexylphosphine)nickel(II) chloride or copper(I) cyanide and an appropriate ligand. Typically the reaction is conducted in a mixture of a solvent such as 1,2-dimethoxyethane, 1,4-dioxane, toluene, or tetrahydrofuran at temperatures ranging from −78° C. to the reflux temperature of the solvent. A typical procedure using an acid chloride is disclosed in *J. Org. Chem.* 2008, 73(4), 1601-1604. A typical procedure using a benzyl chloride is disclosed in *Synth. Commun.* 2012, 42(11), 1613-1621. Compounds of Formulae 6a and 6b are commercially available or their preparation is known in the art.

Scheme 3

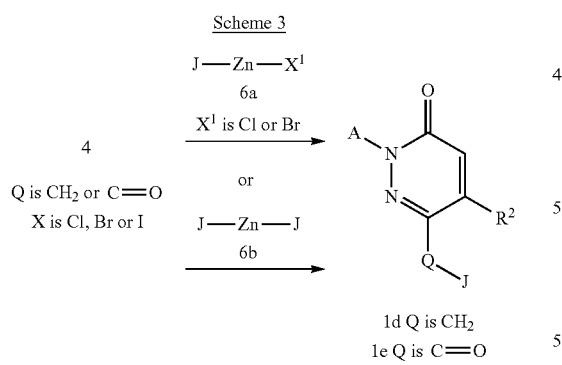

A compound of Formula 1d can be synthesized from a compound of Formula 7 by the reaction shown in Scheme 4. Benzyl alcohols of Formula 7 are reacted with a suitable organomagnesium halide of Formula 8 in the presence of a nickel salt or complex such as nickel(II) chloride, nickel(II) bromide, nickel(II) acetoacetate or bis(tricyclohexylphosphine)nickel(II) chloride and an appropriate ligand such as tricyclohexylphosphine, 1,2-bis(diphenylphosphino)ethane or 1,3-bis(2,6-diisopropylphenyl)-1,3-dihydro-2H-imidazol-2-ylidene. Typically the reaction is conducted in a mixture of solvents including, but not limited to, dibutyl ether, diisopropyl ether and toluene at temperatures ranging from ambient temperature to the reflux temperature of the solvent. For the discovery and optimization of this reaction, see D-G. Yu et al. in *J. Am. Chem. Soc.* 2012, 134, 14638-14641. A compound of Formula 8 is commercially available or its preparation is known in the art.

Scheme 4

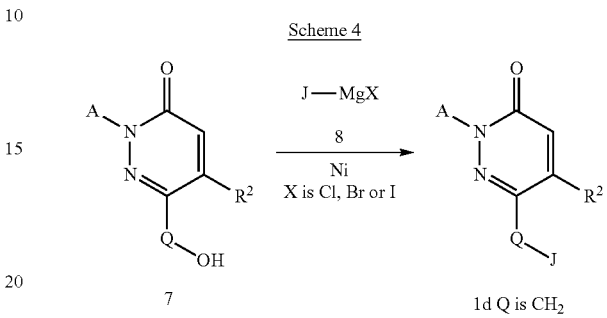

A compound of Formula 1f (wherein Q is CH$_2$ and J is bound to Q through a nitrogen atom) can be synthesized from a compound of Formula 4a by the reaction shown in Scheme 4 wherein X is a suitable leaving group, for example, a halogen or sulfonate, and wherein J is a nitrogen-containing heterocycle (i.e. a heteroaromatic ring containing N—H). The reaction is typically conducted in the presence of an appropriate base such as potassium carbonate, cesium carbonate or potassium hydroxide. Typically the reaction is conducted in a solvent such as dimethylsulfoxide, N,N-dimethylformamide, N,N-dimethylacetamide, N-methylpyrrolidinone or acetonitrile at temperatures ranging from ambient temperature to the reflux temperature of the solvent. A compound of Formula 9 is commercially available or its preparation is known in the art. A typical procedure is discussed in *Nature Chemical Biology* 2008, 4(11), 691-699.

Scheme 5

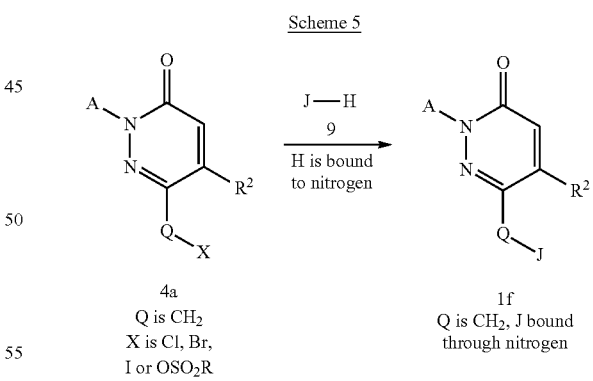

As shown in Scheme 6, a compound of Formula 1e can be synthesized from a compound of Formula 10 and an organolithium or organomagnesium compound of Formula 11. Typically, these reactions are conducted in a solvent mixture containing tetrahydrofuran, diethyl ether or toluene at a temperature ranging from −78° C. to ambient temperature. A compound of Formula 11 is commercially available or its preparation is known in the art. A typical procedure is disclosed in PCT Patent publication WO 2009/121939.

Scheme 6

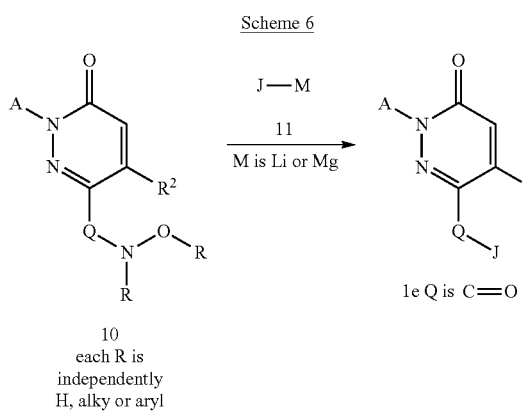

10
each R is
independently
H, alky or aryl

Compounds of Formulae 1a, 1b or 1c can alternatively be synthesized by the reaction of pyridazinones of Formula 12 with a compound of Formula 13 in the presence of a base as shown in Scheme 7. Appropriate solvents for these substitution reactions include acetonitrile, methanol and tetrahydrofuran either alone or mixtures thereof. These reactions are usually conducted at temperatures ranging from 0° C. to the reflux temperature of the solvent. Bases such as potassium carbonate, sodium hydride, sodium carbonate, potassium tert-butoxide, and many others can be employed. The use of an exogenous base is not necessary when anilines are used as the nucleophile. A typical procedure using a phenol is disclosed in UK Patent Application GB 2193493. A typical procedure using a thiophenol is disclosed in *Pest. Sci.* 1996, 48(2), 189-196. A typical procedure using an aniline is disclosed in *J. Chem. Soc., Perkin Transactions* 1 1981, 503-513. Compounds of Formulae 12 and 13 are commercially available or their preparation is known in the art.

Scheme 7

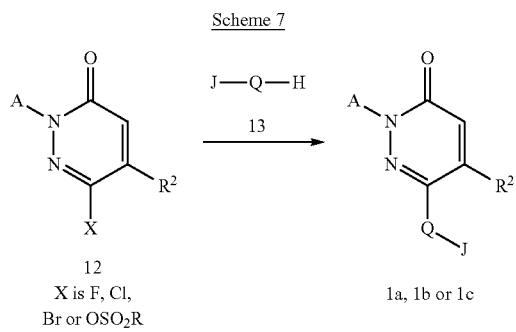

A compound of Formula 1d or 1e can be synthesized from compounds of Formula 12 by the reaction shown in Scheme 8. Halides or sulfonates of Formula 12 are reacted with a suitable benzyl (i.e. a compound of Formula 14a) or aryl (i.e. a compound of Formula 14b) metallic reagent where the identity of the metal (i.e. M) is Li, MgX, ZnX, B(OR)$_2$ or SnR$_3$, optionally in the presence of carbon monoxide (or a carbon monoxide source such as Mo(CO)$_6$), optionally in the presence of a suitable base and in the presence of a palladium or nickel salt or complex such as palladium(II) acetate, tetrakis(triphenylphosphine)palladium(0), bis(triphenylphosphine)palladium(II) chloride, nickel(II) chloride, nickel(II) bromide, nickel(II) acetoacetate or bis(tricyclohexylphosphine)nickel(II) chloride and an appropriate ligand. Bases such as potassium carbonate, sodium hydride, sodium carbonate, potassium tert-butoxide, triethylamine and many others can be employed. Typically the reaction is conducted in a mixture of a solvent such as N,N-dimethylformamide, 1,2-dimethoxyethane, 1,4-dioxane, toluene, or tetrahydrofuran at temperatures ranging from −78° C. to the reflux temperature of the solvent. Typical procedures using benzyl bromides are disclosed in *Eur. J. Chem.* 2011, 46(2), 488-496 and in PCT Patent publication WO 2012/004714. A typical procedure using a benzyl chloride is disclosed in *Angew. Chem. Int. Ed.* 2011, 50(46), 10913-10916. Compounds of Formulae 14a and 14b are commercially available or their preparation is known in the art.

Scheme 8

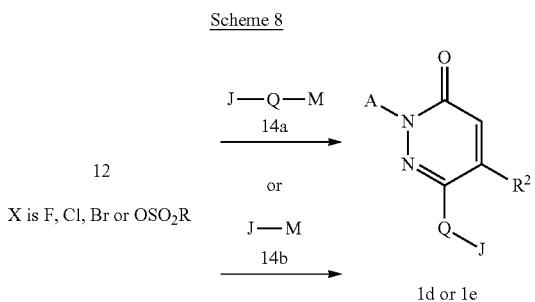

Compounds of Formulae 1a, 1b or 1c can also be synthesized from a compound of Formula 15 by the reaction shown in Scheme 9 of an electron-deficient aromatic or heteroaromatic compound of Formula 16 wherein X is a suitable leaving group, for example, a halogen, sulfonyl (such as alkylsulfonyl, trifluoromethanesulfonyl, phenylsulfonyl or p-toluenesulfonyl) or lower alkoxide, in the presence of an appropriate base such as potassium carbonate, cesium carbonate or potassium hydroxide. Typically the reaction is conducted in a solvent such as dimethylsulfoxide, N,N-dimethylformamide, N,N-dimethylacetamide, N-methylpyrrolidinone or acetonitrile at temperatures ranging from ambient temperature to the reflux temperature of the solvent. For reaction conditions for this general coupling methodology, see Carey, F. A.; Sundberg, R. J., *Advanced Organic Chemistry Part B*, 4$^{th}$ Edition; Kluwer Academic/Plenum Publishers, New York, 2001; Chapter 11.2.2 and references cited therein. In cases where a compound of Formula 16 lacks sufficiently electron-withdrawing substituents to enable the aromatic substitution in a practical time frame, a suitable nitro-containing aromatic or heteroaromatic compound of Formula 17 can be used to enhance the reaction rate. It is obvious to one skilled in the art that reduction of the nitro group followed by diazotization/reduction of the resulting aniline will satisfactorily remove the activating nitro group. A typical procedure for this series of steps is disclosed in *Angew. Chem. Int. Ed.* 2010, 49(11), 2018-2022. Compounds of Formulae 16 and 17 are commercially available or their preparation is known in the art.

Scheme 9

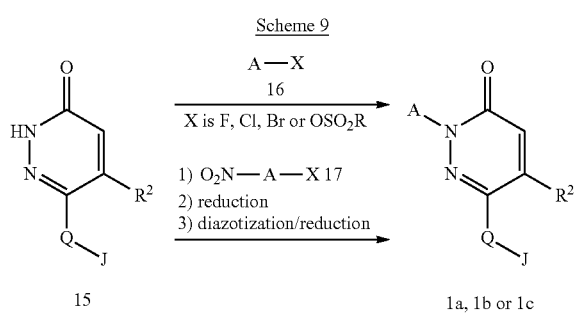

A Compound of Formulae 1a, 1b or 1c can be synthesized from a compound of Formula 18 by the reaction shown in Scheme 10. A compound of Formula 18 is reacted with a suitable boronic acid or boronate ester of Formula 19 in the presence of a copper salt or complex such as copper(II) acetate, di-µ-hydroxy-bis(N,N,N',N'-tetramethylenediamine)copper(II), copper(II) oxide, copper(I) thiophene-2-carboxylate or copper(II) sulfate and a base such as pyridine, triethylamine, diisopropylethylamine, 1,8-diazabicyclo[5.4.0]undec-7-ene or tetramethylethylenediamine. Typically the reaction is conducted in a mixture of a solvent such as dichloromethane, dimethylsulfoxide, N-methylpyrrolidinone or acetonitrile at temperatures ranging from ambient temperature to the reflux temperature of the solvent. For reaction conditions for this general coupling methodology, see *Synthesis* 2011, 6, 829-856. A compound of Formula 19 is commercially available or its preparation is known in the art.

Scheme 11

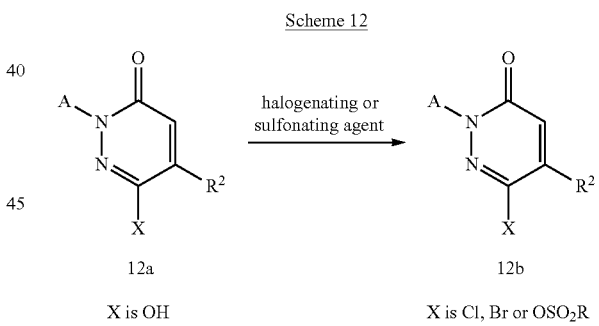

A compound of Formula 12a can be synthesized from a compound of Formula 12b by the reaction shown in Scheme 9 by the action of a halogenating agent such as phosphorus oxybromide or phosphorus oxychloride, in solvents such as excess halogenating reagent, 1,4-dioxane, 1,2-dichloroethane, chloroform or toluene, at temperatures ranging from ambient to the reflux temperature of the solvent. Alternatively, a sulfonate can be formed by the action of a sulfonyl chloride, sulfonyl fluoride or sulfonyl anhydride, in the presence of an appropriate base such as triethylamine, pyridine, 4-dimethylaminopyridine, in solvents such as 1,4-dioxane, dichloromethane, 1,2-dichloroethane, chloroform or toluene, at temperatures ranging from ambient to the reflux temperature of the solvent. A typical chlorination procedure using phosphorus oxychloride is reported in *J. Med. Chem.* 2011, 54, 2102-2113.

Scheme 10

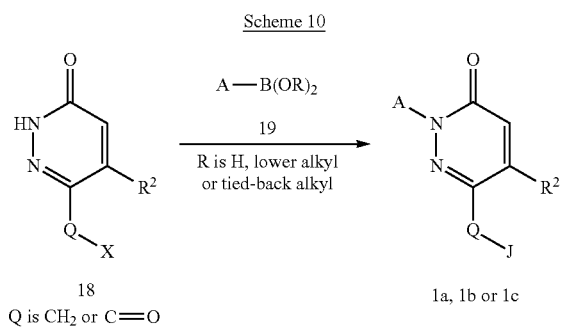

As illustrated in Scheme 11, using reaction conditions similar to those discussed in the method of Scheme 7, pyridazinones of Formula 20 can be converted into pyridazinones of Formula 21. Compounds of Formulae 20 and 13 are commercially available or their preparation is known in the art.

Scheme 12

Compounds of Formulae 12a and 25 can be synthesized from a compound of Formula 23 by the reaction shown in Scheme 13 of an arylhydrazine of Formula 24 with an appropriately substituted maleic anhydride of Formula 23. Typically the reaction is conducted in a polar protic solvent such as water or acetic acid at temperatures ranging from ambient temperature to the reflux temperature of the solvent. Acid promotors for the reaction are typically hydrohalides, sulfuric acid, phosphoric acid or acetic acid. A typical procedure is reported in *Helv. Chim. Acta* 1954, 37, 510-523. Compounds of Formulae 23 and 24 are commercially available or their preparation is known in the art.

Scheme 13

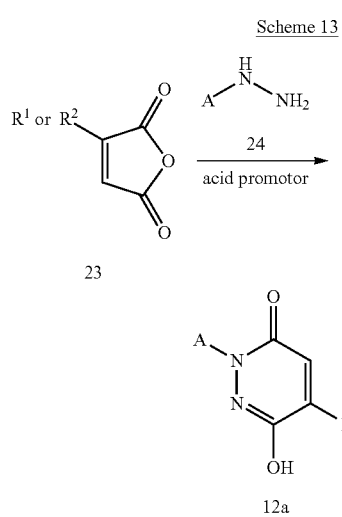

As shown in Scheme 14, a compound of Formula 4a can be prepared from esters of Formula 26 by general methods well known to one skilled in the art. Esters of Formula 26 can be reduced to the corresponding alcohols using a wide variety of reagents, but metal hydride reagents such as lithium aluminum hydride, diisobuyl aluminum hydride or lithium borohydride are particularly general and effective. Typically, these reductions are performed in an ethereal solvent such as diethyl ether, tetrahydrofuran or 1,2-dimethoxyethane at temperatures ranging from −78° C. to the reflux temperature of the solvent. For a comprehensive overview of the methodologies available to reduce esters to alcohols, see R. Larock, C., *Comprehensive Organic Transformations: A Guide to Functional Group Preparations*, 2nd Ed., Wiley-VCH, New York, 1999; and references cited therein. Alcohols of Formula 7a can then be converted to the compounds of Formula 4b using a wide range of reagents such as thionyl chloride, phosphorus trichloride, phosphorus tribromide, triphenylphosphine/bromine, triphenylphosphine/iodine. Alternatively, halogenation methods using hydrohalides in solvents such as acetic acid, acetonitrile, diethyl ether, tetrahydrofuran, dichloromethane, water or a mixture of water with the aforementioned solvents, at temperatures ranging from 0° C. to the reflux temperature of the solvent can be used. Typical procedures for the production of a bromomethyl compound are disclosed in PCT Patent publication WO 2005/115383.

Scheme 14

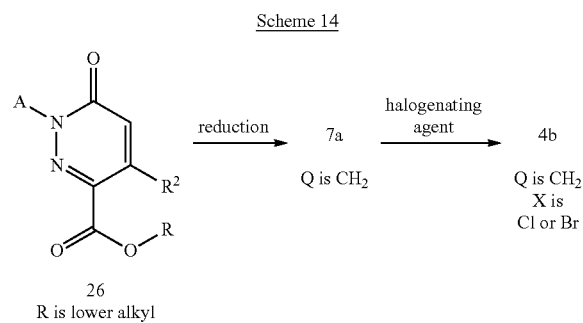

As illustrated in Scheme 15, using reaction conditions similar to those discussed in the method of Scheme 9, pyridazinones of Formula 27 can be converted into N-aryl pyridazinones of Formula 12c, 26 or 28. Compounds of Formulae 27 (where $Q^1$ is lower alkyl) are commercially available or their preparation is known in the art.

Scheme 15

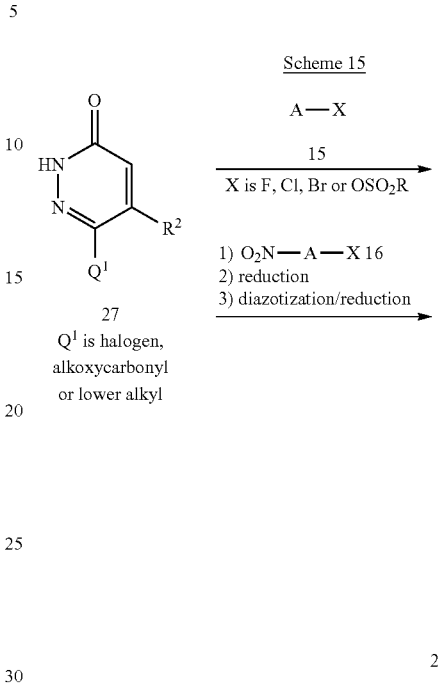

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular order presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following non-limiting Examples are illustrative of the invention. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "m" means multiplet, and "br s" means broad singlet. Mass spectra are reported as the molecular weight of the highest isotopic abundance parent ion (M+1) formed by addition of H+(molecular weight of 1) to the molecule, or (M−1) formed by the loss of H+(molecular weight of 1) from the molecule, observed by using liquid chromatography coupled to a mass spectrometer (LCMS) using either atmospheric pressure chemical ionization (AP$^+$) or electrospray ionization (ES$^+$ or ES$^-$).

Synthesis Example 1

Preparation of 5-ethoxy-2-(4-fluorophenyl)-6-[[2-(trifluoromethyl)-4-pyridinyl]carbonyl]-3(2H)-pyridazinone (Compound 22)

Step A: Preparation of ethyl ester 1-(4-fluorophenyl)-1,6-dihydro-4-hydroxy-6-oxo-3-pyridazinecarboxylic acid A stirred mixture of 4-fluoroaniline (5.00 g, 45.0 mmol) in 2.2 M aqueous hydrochloric acid (60 mL) was cooled to 0° C. A cold solution of sodium nitrite (3.26 g, 47.3 mmol) in water (10 mL) was added over 5 min. Ice was added directly to the reaction mixture to keep the temperature below 5° C. The reaction mixture was stirred at 0° C. for 1 h, then sodium acetate (14.8 g, 180 mmol) and diethyl 1,3-acetonedicarboxylate (9.10 g, 45.0 mmol) were added sequentially. A dark semisolid precipitated out of solution immediately. The mixture was allowed to warm to 23° C. and was stirred at this temperature for 75 min. The aqueous layer was decanted from the dark semisolid. The semisolid was dissolved in ethyl acetate (50 mL) and the residual water was separated off. The organic layer was dried over MgSO$_4$, filtered, and evaporated under reduced pressure to afford a mixture of hydrazones as a dark oil. This dark oil was dissolved in 1,2-dichlorobenzene (25 mL) and heated to 180° C. for 15 h. The solution was concentrated under reduced pressure to afford the title compound as a dark brown solid (14.5 g).
$^1$H NMR δ 10.54 (s, 1H), 7.50-7.62 (m, 2H), 7.11-7.24 (m, 2H), 6.37 (s, 1H), 4.45-4.55 (m, 2H), 1.40-1.46 (m, 3H).

Step B: Preparation of ethyl ester 4-ethoxy-1-(4-fluorophenyl)-1,6-dihydro-6-oxo-3-pyridazinecarboxylic acid To a stirred solution of ethyl ester 1-(4-fluorophenyl)-1,6-dihydro-4-hydroxy-6-oxo-3-pyridazinecarboxylic acid (i.e. the product of Step A, 0.50 g, 1.8 mmol) in N,N-dimethylformamide (3 mL) was added potassium carbonate (0.50 g, 3.6 mmol) and iodoethane (0.29 mL, 3.6 mmol). The reaction mixture was stirred at 50° C. for 22.5 h. The reaction mixture was diluted with water (30 mL). The precipitated solid was collected by filtration and washed with water. This material was purified by chromatography on silica gel eluting with 0 to 40% ethyl acetate in hexanes to afford the title compound as a beige solid (0.48 g). [M+1]$^+$=307.3 amu Step C: Preparation of 4-ethoxy-1-(4-fluorophenyl)-1,6-dihydro-6-oxo-3-pyridazinecarbonyl chloride Ethyl ester 4-ethoxy-1-(4-fluorophenyl)-1,6-dihydro-6-oxo-3-pyridazinecarboxylic acid (i.e. the product of Step B, 0.48 g, 1.6 mmol) was dissolved in tetrahydrofuran (10 mL). A 1.0 M aqueous solution of sodium hydroxide (10 mL) was added, and the biphasic reaction mixture was stirred vigorously at 23° C. for 2.3 h. The reaction mixture was acidified to pH 1 with concentrated hydrochloric acid and then extracted with ethyl acetate. The organic layer was dried over MgSO$_4$ and concentrated under reduced pressure to afford the crude carboxylic acid as a beige solid. This solid was suspended in dichloromethane (10 mL). N,N-Dimethylformamide (1 drop) and oxalyl chloride (0.20 mL, 2.4 mmol) were added, and the mixture was stirred at 23° C. for 18 h. The pale yellow solution was concentrated under reduced pressure to afford the title compound as a pale yellow solid (0.40 g).
$^1$H NMR δ 7.62-7.69 (m, 2H), 7.15-7.23 (m, 2H), 6.27 (s, 1H), 4.12-4.18 (m, 2H), 1.50-1.55 (m, 3H).

Step D: Preparation of 5-ethoxy-2-(4-fluorophenyl)-6-[[2-(trifluoromethyl)-4-pyridinyl]carbonyl]-3(2H)-pyridazinone A solution of isopropylmagnesium chloride lithium chloride complex (1.3 M in tetrahydrofuran, 1.19 mL, 1.54 mmol) was added to a solution of 4-iodo-2-(trifluoromethyl)pyridine (0.40 g, 1.47 mmol) in tetrahydrofuran (1 mL) cooled to −78° C. The solution was stirred at this temperature for 1 h. A solution of zinc chloride in 2-methyltetrahydrofuran (1.9 M, 0.77 mL, 1.47 mmol) was added at −78° C. and then stirred at 23° C. for 10 min. 4-Ethoxy-1-(4-fluorophenyl)-1,6-dihydro-6-oxo-3-pyridazinecarbonyl chloride (i.e. the product of Step C, 0.40 g, 1.47 mmol) and tetrakis(triphenylphosphine)palladium(0) (0.17 g, 0.15 mmol) were added, and the reaction was stirred for 6 h. The reaction mixture was directly adsorbed onto silica gel and was purified by chromatography on silica gel eluting with 0 to 80% ethyl acetate in hexanes to afford the title compound (0.21 g) as a beige solid.
$^1$H NMR δ 8.90-8.95 (m, 1H), 8.12-8.14 (m, 1H), 7.89-7.94 (m, 1H), 7.48-7.54 (m, 2H), 7.11-7.17 (m, 2H), 6.38 (s, 1H), 4.10-4.20 (m, 2H), 1.42-1.48 (m, 3H).

Synthesis Example 2

Preparation of 5-ethoxy-2-(4-fluorophenyl)-6-[hydroxy[2-(trifluoromethyl)-4-pyridinyl]methyl]-3(2H)-pyridazinone (Compound 23)

Step A: Preparation of 5-ethoxy-2-(4-fluorophenyl)-6-[hydroxy[2-(trifluoromethyl)-4-pyridinyl]methyl]-3(2H)-pyridazinone A solution of 5-ethoxy-2-(4-fluorophenyl)-6-[[2-(trifluoromethyl)-4-pyridinyl]carbonyl]-3(2H)-pyridazinone (i.e.

the product of Example 1, Step D) (0.15 g, 0.37 mmol) in methanol (2 mL) and tetrahydrofuran (2 mL) was cooled to 0° C. Sodium borohydride (0.028 g, 0.74 mmol) was added, and the mixture was allowed to warm to 23° C. over 2 h. The reaction was quenched with the addition of 1.0 M aqueous hydrochloric acid and then extracted with ethyl acetate (2×15 mL). The combined organic layers were dried over MgSO$_4$ and concentrated under reduced pressure. The crude residue was purified by filtration through a short (~2.5 cm) silica gel plug eluting with ethyl acetate to afford the title compound as a yellow oil (0.15 g).

$^1$H NMR δ 8.70-8.75 (m, 1H), 7.75-7.79 (m, 1H), 7.50-7.58 (m, 3H), 7.14-7.22 (m, 2H), 6.25 (s, 1H), 5.91 (s, 1H), 3.98-4.10 (m, 2H), 3.96 (br s, 1H), 1.38-1.45 (m, 3H).

Synthesis Example 3

Preparation of 2-(4-fluorophenyl)-5-methyl-6-[[2-(trifluoromethyl)-4-pyridinyl]methyl]-3(2H)-pyridazinone (Compound 1)

Step A: Preparation of ethyl ester 4-chloro-1-(4-fluorophenyl)-1,6-dihydro-6-oxo-3-pyridazinecarboxylic acid Ethyl ester 1-(4-fluorophenyl)-1,6-dihydro-4-hydroxy-6-oxo-3-pyridazinecarboxylic acid (i.e. the product of Example 1, Step A, 5.0 g, 18.0 mmol) was dissolved in phosphorus oxychloride (50 mL) and stirred at 90° C. for 24 h. The volatiles were removed under reduced pressure and the resulting residue was partitioned between saturated aqueous sodium bicarbonate solution (50 mL) and ethyl acetate (150 mL) and stirred vigorously for 1 h. The layers were separated, and the aqueous layer was extracted with ethyl acetate (25 mL). The combined organic layers were dried over MgSO$_4$ and concentrated under reduced pressure. The crude residue was purified by chromatography on silica gel eluting with 0 to 40% ethyl acetate in hexanes to afford the title compound as an orange solid (3.1 g).

$^1$H NMR δ 7.55-7.65 (m, 2H), 7.14-7.22 (m, 3H), 4.40-4.48 (m, 2H), 1.35-1.46 (m, 3H).

Step B: Preparation of ethyl ester 1-(4-fluorophenyl)-1,6-dihydro-4-methyl-6-oxo-3-pyridazinecarboxylic acid Ethyl ester 4-chloro-1-(4-fluorophenyl)-1,6-dihydro-6-oxo-3-pyridazinecarboxylic acid (i.e. the product of Step A, 1.40 g, 4.7 mmol) and tetrakis(triphenylphosphine)palladium(0) (0.27 g, 0.24 mmol) were dissolved in anhydrous dioxane (40 mL) under a nitrogen atmosphere. A solution of trimethylaluminum (2.0 M in toluene, 2.6 mL, 5.2 mmol) was added. The reaction mixture was heated to reflux for 4 h. The reaction was cooled to 0° C. and then quenched by the sequential addition of ethyl acetate (5 mL) and methanol (5 mL). When gas evolution ceased, water (2 mL) and then sodium sulfate (5 g) was added. The mixture was stirred at 23° C. for 1 h. The mixture was dried over MgSO$_4$ and concentrated under reduced pressure to afford the title compound as a brown-orange solid.

$^1$H NMR δ 7.59-7.65 (m, 2H), 7.12-7.19 (m, 2H), 6.83-6.86 (m, 1H), 4.36-4.45 (m, 2H), 2.45-2.48 (m, 3H), 1.36-1.43 (m, 3H).

Step C: Preparation of 2-(4-fluorophenyl)-6-(hydroxymethyl)-5-methyl-3(2H)-pyridazinone Crude ethyl ester 1-(4-fluorophenyl)-1,6-dihydro-4-methyl-6-oxo-3-pyridazinecarboxylic acid (i.e. the product of Step B, <4.7 mmol) was suspended in ethanol (50 mL) and heated to 60° C. Sodium borohydride (0.89 g, 24 mmol) was added. The reaction was stirred at 60° C. for 1 h during which time a dark black solution formed. The volatiles were removed under reduced pressure. The residue was partitioned between water and ethyl acetate, and the layers were separated The organic layer was washed with saturated aqueous sodium chloride solution, dried over MgSO$_4$ and concentrated under reduced pressure to afford the title compound as a dark brown solid.

$^1$H NMR δ 7.57-7.63 (m, 2H), 7.12-7.19 (m, 2H), 6.83-6.87 (m, 1H), 4.42 (s, 2H), 2.37-2.43 (m, 3H), 1.54 (br s, 1H).

Step D: Preparation of 6-(bromomethyl)-2-(4-fluorophenyl)-5-methyl-3(2H)-pyridazinone Crude 2-(4-fluorophenyl)-6-(hydroxymethyl)-5-methyl-3(2H)-pyridazinone (i.e. the product of Step C, <4.7 mmol) was suspended in 48% aqueous hydrobromic acid (15 mL) and heated to reflux for 2 h. The mixture was cooled to 0° C., basified to pH 14 and extracted with ethyl acetate (2×50 mL). The combined organic layers were washed with saturated aqueous sodium chloride solution, dried over MgSO$_4$ and concentrated under reduced pressure. The crude residue was purified by filtration through a short (~2.5 cm) silica gel plug eluting with ethyl acetate to afford the title compound as a pale yellow solid (1.05 g).

$^1$H NMR δ 7.57-7.62 (m, 2H), 7.11-7.19 (m, 2H), 6.83-6.87 (m, 1H), 4.42 (s, 2H), 2.39-2.41 (m, 3H).

Step E: Preparation of 2-(4-fluorophenyl)-5-methyl-6-[[2-(trifluoromethyl)-4-pyridinyl]methyl]-3(2H)-pyridazinone To a mixture of 6-(bromomethyl)-2-(4-fluorophenyl)-5-methyl-3(2H)-pyridazinone (i.e. the product of Step D, 1.05 g, 3.5 mmol) in tetrahydrofuran/water (3:1, 16 mL total) was added potassium phosphate tribasic (2.25 g, 10.6 mmol) and 2-(trifluoromethyl)pyridine-4-boronic acid pinacol ester (1.16 g, 4.2 mmol). The mixture was sparged with nitrogen for 15 min, and then tetrakis(triphenylphosphine)palladium (0) (0.20 g, 0.17 mmol) was added. The mixture was heated to 70° C. and stirred for 69 h under an atmosphere of nitrogen. The reaction mixture was diluted with ethyl acetate (30 mL) and washed with saturated aqueous sodium chloride solution (15 mL). The organic layer was dried over MgSO$_4$ and concentrated under reduced pressure. The crude residue was purified by chromatography on silica gel eluting with 0 to 100% ethyl acetate in hexanes, and then was purified by reverse-phase chromatography on C$_{18}$ silica gel to afford the title compound as a yellow solid (0.20 g).

$^1$H NMR δ 8.66-8.71 (m, 1H), 7.55-7.62 (m, 3H), 7.32-7.38 (m, 1H), 7.10-7.19 (m, 2H), 6.83-6.87 (m, 1H), 4.09 (s, 2H), 2.13-2.17 (m, 3H).

Synthesis Example 4

Preparation of 2-(4-fluorophenyl)-5-methyl-6-[[3-(trifluoromethyl)-1H-pyrazol-1-yl]methyl]-3(2H)-pyridazinone (Compound 3)

Step A: Preparation of 2-(4-fluorophenyl)-5-methyl-6-[[3-(trifluoromethyl)-1H-pyrazol-1-yl]methyl]-3(2H)-pyridazinone To a solution of 6-(bromomethyl)-2-(4-fluorophenyl)-5-methyl-3(2H)-pyridazinone (i.e. the product of Example 3, Step D) (0.14 g, 0.47 mmol) in N,N-dimethylformamide (2 mL total), was added 3-(trifluoromethyl)pyrazole (0.064 g, 0.47 mmol) and anhydrous potassium carbonate (0.065 g, 0.47 mmol). The mixture was stirred for 2 h at 23° C. The reaction mixture was diluted with water (10 mL) and extracted with diethyl ether (4×10 mL). The combined organic layers were washed with water (2×10 mL), dried (MgSO₄) and concentrated under reduced pressure. The crude residue was purified by chromatography on silica gel eluting with 0 to 100% ethyl acetate in hexanes to afford the title compound as a pale yellow solid (0.090 g).

$^1$H NMR δ 7.48-7.62 (m, 3H), 7.11-7.20 (m, 2H), 6.82-6.86 (m, 1H), 6.56-6.60 (m, 1H), 5.35 (s, 2H), 2.21-2.26 (m, 3H).

Synthesis Example 5

Preparation of 4-methyl-2-[4-(trifluoromethyl)phenyl]-6-[[2-(trifluoromethyl)-4-pyridinyl]oxy]-3(2H)-pyridazinone (Compound 6) and 5-methyl-2-[4-(trifluoromethyl)phenyl]-6-[[2-(trifluoromethyl)-4-pyridinyl]oxy]-3(2H)-pyridazinone (Compound 5)

Step A: Preparation of 4-methyl-2-[4-(trifluoromethyl)phenyl]-6-[[2-(trifluoromethyl)-4-pyridinyl]oxy]-3(2H)-pyridazinone and 5-methyl-2-[4-(trifluoromethyl)phenyl]-6-[[2-(trifluoromethyl)-4-pyridinyl]oxy]-3(2H)-pyridazinone 4-Trifluoromethylphenyl hydrazine (4.8 g, 27 mmol) was treated with a mixture of 1 N hydrochloric acid (20 mL) and concentrated hydrochloric acid (2 mL) followed by citraconic anhydride (2.6 mL, 27 mmol). The mixture was heated at 100° C. for 2 h. The reaction mixture produced a thick suspension which, upon cooling, was filtered and washed with water (2×25 mL). The solid was mixed with aqueous sodium hydroxide (1 N, 100 mL) and extracted with dichloromethane (2×100 mL). The aqueous layer was acidified with concentrated hydrochloric acid. The solid produced was filtered and washed with water (3×10 mL). Drying afforded a solid mixture of 4- and 5-methylpyridazinones (1.3 g) which was dissolved in dimethylformamide (5 mL) and treated successively with 4-chloro-2-trifluoromethylpyridine (0.9 g, 5 mmol) and potassium carbonate (2.4 g, 17 mmol). The resulting mixture was heated at 110° C. for 18 h and poured onto ice-water (100 g). After standing the aqueous layer was decanted from an oil which was dissolved in dichloromethane (50 mL) and dried over MgSO₄. The residue after filtration and evaporation was subjected to chromatography on silica gel (24 g) eluting with ethyl acetate in hexanes (0-100%). The title compound was eluted first as a thick oil (150 mg).

$^1$H NMR δ 8.72 (m, 1H), 7.76 (m, 1H), 7.70 (m, 2H), 7.59 (m, 2H), 7.37 (m, 1H), 7.15 (m, 1H), 2.38 (s, 3H).

Continued elution produced the Compound 5 of Example 5 as a solid (230 mg).

$^1$H NMR δ 8.74 (m, 1H), 7.74 (m, 1H), 7.68 (m, 2H), 7.62 (m, 2H), 7.39 (m, 1H), 7.01 (m, 1H), 2.34 (s, 3H).

By the procedures described herein together with methods known in the art, the following compounds of Tables 1 to 1504 can be prepared. The following abbreviations are used in the Tables which follow: n means normal, i means iso, Me means methyl, Et means ethyl, Pr means propyl, i-Pr means isopropyl and Ph means phenyl. The following structures are used in the Tables which follow:

TABLE 1

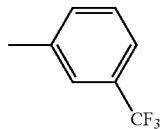  J-1a

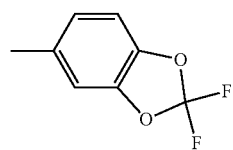  J-1b

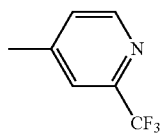  J-2a

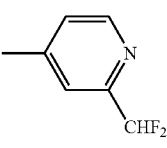  J-2b

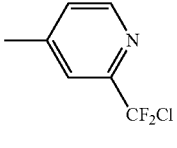  J-2c

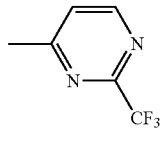  J-10a

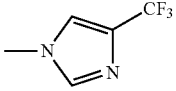  J-17a

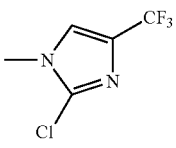  J-17b

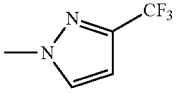  J-18a

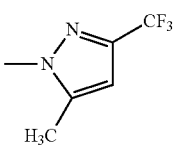  J-18b

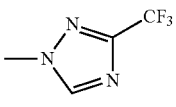  J-20a

TABLE 1-continued

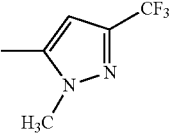

J-22a

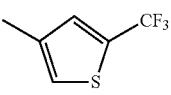

J-29a

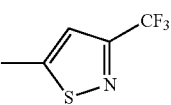

J-33a

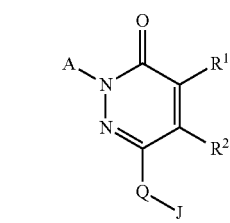

J=J-1, Q=O, R¹=CH₃, R²=H

| A | A | A |
|---|---|---|
| 4-F—Ph | 3-CF₃—Ph | 2-Br—Ph |
| 4-CF₃—Ph | 3-Cl—Ph | 2,4-diF-Ph |
| 4-Cl—Ph | 3-Br—Ph | 3,4-diF-Ph |
| 4-Br—Ph | 3-SF₅—Ph | 2,5-diF-Ph |
| 4-SF₅—Ph | 3-OCF₃—Ph | 2,4,6-tri-Ph |
| 4-OCF₃—Ph | 3-SMe—Ph | 2-Cl-4-F—Ph |
| 4-SMe—Ph | 3-OMe—Ph | 3-Cl-4-F—Ph |
| 4-OMe—Ph | 3-CN—Ph | 4-F-3-CF₃—Ph |
| 4-CN—Ph | 3-Me—Ph | 2-F-4-CF₃—Ph |
| 4-Me—Ph | 2-F—Ph | 3-F-4-CF₃—Ph |
| 4-Ph | 2-CF₃—Ph | 3-Cl-4-CF₃—Ph |
| 3-F—Ph | 2-Cl—Ph | 2-Cl-4-CF₃—Ph |
| 4-Cl-3-CF₃—Ph | 5-CF₃-3-Pyridyl | 5-Cl-2-Pyrimidyl |
| 2-Pyridyl | 2-CF₃-5-Pyridyl | 5-CF₃-2-Pyrimidyl |
| 3-Pyridyl | 5-CF₃-2-Pyrazinyl | 2-CF₃-4-Pyrimidyl |
| 4-Pyridyl | 6-CF₃-3-Pyridazinyl | 4-CF₃-2-Pyrimidyl |
| 5-CF₃-2-Pyridyl | 5-F-2-Pyridyl | 5-Cl-2-Thienyl |
| 5-Cl-2-Pyridyl | 2-F-4-Pyridyl | 5-CF₃-2-Thienyl |
| 2-CF₃-4-Pyridyl | 6-F-2-Pyridyl | 4-CF₃-2-Thiazolyl |
| 2-Cl-4-Pyridyl | 5-F-3-Pyridyl | 5-CF₃-1,2,5-Thiadiazol-2-yl |
| 6-CF₃-2-Pyridyl | 2-F-5-Pyridyl | |

The present disclosure also includes Tables 2-1449. Each Table is constructed in the same manner as Table 1 above, except that the row heading in Table 1 (i.e. "J=J-1, Q=O, R¹=CH₃ R²=H") is replaced with the respective row heading shown below. For example, in Table 2 the row heading is "J=J-2a, Q=O and R¹ is Et, R²=H" and A is as defined in Table 1.

TABLE 1450

| Table | Row Heading |
|---|---|
| 2 | J = J-2a, Q = O, R¹ = Et, R² = H |
| 3 | J = J-2a, Q = O, R¹ = n-Pr, R² = H |
| 4 | J = J-2a, Q = O, R¹ = n-Pi, R² = H |
| 5 | J = J-2a, Q = O, R¹ = CH₂OMe, R² = H |

TABLE 1450-continued

| Table | Row Heading |
|---|---|
| 6 | J = J-2a, Q = O, R¹ = CH₂F, R² = H |
| 7 | J = J-2a, Q = O, R¹ = CHF₂, R² = H |
| 8 | J = J-2a, Q = O, R¹ = CF₃, R² = H |
| 9 | J = J-2a, Q = O, R¹ = OMe, R² = H |
| 10 | J = J-2a, Q = O, R¹ = OEt, R² = H |
| 11 | J = J-2a, Q = O, R¹ = OCHF₂, R² = H |
| 12 | J = J-2a, Q = O, R¹ = OCH₂CF₃, R² = H |
| 13 | J = J-2a, Q = O, R¹ = NHMe, R² = H |
| 14 | J = J-2a, Q = O, R¹ = NHEt, R² = H |
| 15 | J = J-2a, Q = O, R¹ = NMe₂, R² = H |
| 16 | J = J-2a, Q = O, R¹ = NEt₂, R² = H |
| 17 | J = J-2a, Q = O, R¹ = NMeEt, R² = H |
| 18 | J = J-2a, Q = O, R¹ = Cl, R² = H |
| 19 | J = J-2a, Q = O, R¹ = Br, R² = H |
| 20 | J = J-2a, Q = O, R¹ = H, R² = Me |
| 21 | J = J-2a, Q = O, R¹ = H, R² = Et |
| 22 | J = J-2a, Q = O, R¹ = H, R² = n-Pr |
| 23 | J = J-2a, Q = O, R¹ = H, R² = i-Pr |
| 24 | J = J-2a, Q = O, R¹ = H, R² = CH₂OMe |
| 25 | J = J-2a, Q = O, R¹ = H, R² = CH₂F |
| 26 | J = J-2a, Q = O, R¹ = H, R² = CHF₂ |
| 27 | J = J-2a, Q = O, R¹ = H, R² = CF₃ |
| 28 | J = J-2a, Q = O, R¹ = H, R² = OMe |
| 29 | J = J-2a, Q = O, R¹ = H, R² = OEt |
| 30 | J = J-2a, Q = O, R¹ = H, R² = OCHF₂ |
| 31 | J = J-2a, Q = O, R¹ = H, R² = OCH₂CF₃ |
| 32 | J = J-2a, Q = O, R¹ = H, R² = NHMe |
| 33 | J = J-2a, Q = O, R¹ = H, R² = NHEt |
| 34 | J = J-2a, Q = O, R¹ = H, R² = NMe₂ |
| 35 | J = J-2a, Q = O, R¹ = H, R² = NEt₂ |
| 36 | J = J-2a, Q = O, R¹ = H, R² = NMeEt |
| 37 | J = J-2a, Q = O, R¹ = H, R² = Cl |
| 38 | J = J-2a, Q = O, R¹ = H, R² = Br |
| 39 | J = J-2a, Q = O, R¹ = Me, R² = Me |
| 40 | J = J-2a, Q = O, R¹ = Et, R² = Et |
| 41 | J = J-2a, Q = O, R¹ = Me, R² = Cl |
| 42 | J = J-2a, Q = O, R¹ = Cl, R² = Me |
| 43 | J = J-2a, Q = O, R¹ = Cl, R² = Cl |
| 44 | J = J-2a, Q = O, R¹, R² = —(CH₂)₃— |
| 45 | J = J-2a, Q = O, R¹, R² = —(CH₂)₄— |
| 46 | J = J-2a, Q = CH₂, R¹ = Me, R² = H |
| 47 | J = J-2a, Q = CH₂, R¹ = Et, R² = H |
| 48 | J = J-2a, Q = CH₂, R¹ = n-Pr, R² = H |
| 49 | J = J-2a, Q = CH₂, R¹ = i-Pr, R² = H |
| 50 | J = J-2a, Q = CH₂, R¹ = CH₂OMe, R² = H |
| 51 | J = J-2a, Q = CH₂, R¹ = CH₂F, R² = H |
| 52 | J = J-2a, Q = CH₂, R¹ = CHF₂, R² = H |
| 53 | J = J-2a, Q = CH₂, R¹ = CF₃, R² = H |
| 54 | J = J-2a, Q = CH₂, R¹ = OMe, R² = H |
| 55 | J = J-2a, Q = CH₂, R¹ = OEt, R² = H |
| 56 | J = J-2a, Q = CH₂, R¹ = OCHF₂, R² = H |
| 57 | J = J-2a, Q = CH₂, R¹ = OCH₂CF₃, R² = H |
| 58 | J = J-2a, Q = CH₂, R¹ = NHMe, R² = H |
| 59 | J = J-2a, Q = CH₂, R¹ = NHEt, R² = H |
| 60 | J = J-2a, Q = CH₂, R¹ = NMe₂, R² = H |
| 61 | J = J-2a, Q = CH₂, R¹ = NEt₂, R² = H |
| 62 | J = J-2a, Q = CH₂, R¹ = NMeEt, R² = H |
| 63 | J = J-2a, Q = CH₂, R¹ = Cl, R² = H |
| 64 | J = J-2a, Q = CH₂, R¹ = Br, R² = H |
| 65 | J = J-2a, Q = CH₂, R¹ = H, R² = Me |
| 66 | J = J-2a, Q = CH₂, R¹ = H, R² = Et |
| 67 | J = J-2a, Q = CH₂, R¹ = H, R² = n-Pr |
| 68 | J = J-2a, Q = CH₂, R¹ = H, R² = i-Pr |
| 69 | J = J-2a, Q = CH₂, R¹ = H, R² = CH₂OMe |
| 70 | J = J-2a, Q = CH₂, R¹ = H, R² = CH₂F |
| 71 | J = J-2a, Q = CH₂, R¹ = H, R² = CHF₂ |
| 72 | J = J-2a, Q = CH₂, R¹ = H, R² = CF₃ |
| 73 | J = J-2a, Q = CH₂, R¹ = H, R² = OMe |
| 74 | J = J-2a, Q = CH₂, R¹ = H, R² = OEt |
| 75 | J = J-2a, Q = CH₂, R¹ = H, R² = OCHF₂ |
| 76 | J = J-2a, Q = CH₂, R¹ = H, R² = OCH₂CF₃ |
| 77 | J = J-2a, Q = CH₂, R¹ = H, R² = NHMe |
| 78 | J = J-2a, Q = CH₂, R¹ = H, R² = NHEt |
| 79 | J = J-2a, Q = CH₂, R¹ = H, R² = NMe₂ |
| 80 | J = J-2a, Q = CH₂, R¹ = H, R² = NEt₂ |
| 81 | J = J-2a, Q = CH₂, R¹ = H, R² = NMeEt |
| 82 | J = J-2a, Q = CH₂, R¹ = H, R² = Cl |
| 83 | J = J-2a, Q = CH₂, R¹ = Me, R² = Me |

TABLE 1450-continued

| Table | Row Heading |
|---|---|
| 84 | J = J-2a, Q = CH$_2$, R$^1$ = Et, R$^2$ = Et |
| 85 | J = J-2a, Q = CH$_2$, R$^1$ = Me, R$^2$ = Cl |
| 86 | J = J-2a, Q = CH$_2$, R$^1$ = Cl, R$^2$ = Me |
| 87 | J = J-2a, Q = CH$_2$, R$^1$ = Cl, R$^2$ = Cl |
| 88 | J = J-2a, Q = CH$_2$, R$^1$, R$^2$ = —(CH$_2$)$_3$— |
| 89 | J = J-2a, Q = CH$_2$, R$^1$, R$^2$ = —(CH$_2$)$_4$— |
| 90 | J = J-2a, Q = C(=O), R$^1$ = Me, R$^2$ = H |
| 91 | J = J-2a, Q = C(=O), R$^1$ = Et, R$^2$ = H |
| 92 | J = J-2a, Q = C(=O), R$^1$ = n-Pr, R$^2$ = H |
| 93 | J = J-2a, Q = C(=O), R$^1$ = i-Pr, R$^2$ = H |
| 94 | J = J-2a, Q = C(=O), R$^1$ = CH$_2$OMe, R$^2$ = H |
| 95 | J = J-2a, Q = C(=O), R$^1$ = CH$_2$F, R$^2$ = H |
| 96 | J = J-2a, Q = C(=O), R$^1$ = CHF$_2$, R$^2$ = H |
| 97 | J = J-2a, Q = C(=O), R$^1$ = CF$_3$, R$^2$ = H |
| 98 | J = J-2a, Q = C(=O), R$^1$ = OMe, R$^2$ = H |
| 99 | J = J-2a, Q = C(=O), R$^1$ = Et, R$^2$ = H |
| 100 | J = J-2a, Q = C(=O), R$^1$ = OCHF$_2$, R$^2$ = H |
| 101 | J = J-2a, Q = C(=O), R$^1$ = OCH$_2$CF$_3$, R$^2$ = H |
| 102 | J = J-2a, Q = C(=O), R$^1$ = NHMe, R$^2$ = H |
| 103 | J = J-2a, Q = C(=O), R$^1$ = NHEt, R$^2$ = H |
| 104 | J = J-2a, Q = C(=O), R$^1$ = NMe$_2$, R$^2$ = H |
| 105 | J = J-2a, Q = C(=O), R$^1$ = NEt$_2$, R$^2$ = H |
| 106 | J = J-2a, Q = C(=O), R$^1$ = NMeEt, R$^2$ = H |
| 107 | J = J-2a, Q = C(=O), R$^1$ = Cl, R$^2$ = H |
| 108 | J = J-2a, Q = C(=O), R$^1$ = Br, R$^2$ = H |
| 109 | J = J-2a, Q = C(=O), R$^1$ = H, R$^2$ = Me |
| 110 | J = J-2a, Q = C(=O), R$^1$ = H, R$^2$ = Et |
| 111 | J = J-2a, Q = C(=O), R$^1$ = H, R$^2$ = n-Pr |
| 112 | J = J-2a, Q = C(=O), R$^1$ = H, R$^2$ = i-Pr |
| 113 | J = J-2a, Q = C(=O), R$^1$ = H, R$^2$ = CH$_2$OMe |
| 114 | J = J-2a, Q = C(=O), R$^1$ = H, R$^2$ = CH$_2$F |
| 115 | J = J-2a, Q = C(=O), R$^1$ = H, R$^2$ = CHF$_2$ |
| 116 | J = J-2a, Q = C(=O), R$^1$ = H, R$^2$ = CF$_3$ |
| 117 | J = J-2a, Q = C(=O), R$^1$ = H, R$^2$ = OMe |
| 118 | J = J-2a, Q = C(=O), R$^1$ = H, R$^2$ = OEt |
| 119 | J = J-2a, Q = C(=O), R$^1$ = H, R$^2$ = OCHF$_2$ |
| 120 | J = J-2a, Q = C(=O), R$^1$ = H, R$^2$ = OCH$_2$CF$_3$ |
| 121 | J = J-2a, Q = C(=O), R$^1$ = H, R$^2$ = NHMe |
| 122 | J = J-2a, Q = C(=O), R$^1$ = H, R$^2$ = NHEt |
| 123 | J = J-2a, Q = C(=O), R$^1$ = H, R$^2$ = NMe$_2$ |
| 124 | J = J-2a, Q = C(=O), R$^1$ = H, R$^2$ = NEt$_2$ |
| 125 | J = J-2a, Q = C(=O), R$^1$ = H, R$^2$ = NMeEt |
| 126 | J = J-2a, Q = C(=O), R$^1$ = H, R$^2$ = Cl |
| 127 | J = J-2a, Q = C(=O), R$^1$ = Me, R$^2$ = Me |
| 128 | J = J-2a, Q = C(=O), R$^1$ = Et, R$^2$ = Et |
| 129 | J = J-2a, Q = C(=O), R$^1$ = Me, R$^2$ = Cl |
| 130 | J = J-2a, Q = C(=O), R$^1$ = Cl, R$^2$ = Me |
| 131 | J = J-2a, Q = C(=O), R$^1$ = Cl, R$^2$ = Cl |
| 132 | J = J-2a, Q = C(=O), R$^1$, R$^2$ = —(CH$_2$)$_3$— |
| 133 | J = J-2a, Q = C(=O), R$^1$, R$^2$ = —(CH$_2$)$_4$— |
| 134 | J = J-2a, Q = C(OH)H, R$^1$ = Me, R$^2$ = H |
| 135 | J = J-2a, Q = C(OH)H, R$^1$ = Et, R$^2$ = H |
| 136 | J = J-2a, Q = C(OH)H, R$^1$ = n-Pr, R$^2$ = H |
| 137 | J = J-2a, Q = C(OH)H, R$^1$ = i-Pr, R$^2$ = H |
| 138 | J = J-2a, Q = C(OH)H, R$^1$ = CH$_2$OMe, R$^2$ = H |
| 139 | J = J-2a, Q = C(OH)H, R$^1$ = CH$_2$F, R$^2$ = H |
| 140 | J = J-2a, Q = C(OH)H, R$^1$ = CHF$_2$, R$^2$ = H |
| 141 | J = J-2a, Q = C(OH)H, R$^1$ = CF$_3$, R$^2$ = H |
| 142 | J = J-2a, Q = C(OH)H, R$^1$ = OMe, R$^2$ = H |
| 143 | J = J-2a, Q = C(OH)H, R$^1$ = OEt, R$^2$ = H |
| 144 | J = J-2a, Q = C(OH)H, R$^1$ = OCHF$_2$, R$^2$ = H |
| 145 | J = J-2a, Q = C(OH)H, R$^1$ = OCH$_2$CF$_3$, R$^2$ = H |
| 146 | J = J-2a, Q = C(OH)H, R$^1$ = NHMe, R$^2$ = H |
| 147 | J = J-2a, Q = C(OH)H, R$^1$ = NHEt, R$^2$ = H |
| 148 | J = J-2a, Q = C(OH)H, R$^1$ = NMe$_2$, R$^2$ = H |
| 149 | J = J-2a, Q = C(OH)H, R$^1$ = NEt$_2$, R$^2$ = H |
| 150 | J = J-2a, Q = C(OH)H, R$^1$ = NMeEt, R$^2$ = H |
| 151 | J = J-2a, Q = C(OH)H, R$^1$ = Cl, R$^2$ = H |
| 152 | J = J-2a, Q = C(OH)H, R$^1$ = Br, R$^2$ = H |
| 153 | J = J-2a, Q = C(OH)H, R$^1$ = H, R$^2$ = Me |
| 154 | J = J-2a, Q = C(OH)H, R$^1$ = H, R$^2$ = Et |
| 155 | J = J-2a, Q = C(OH)H, R$^1$ = H, R$^2$ = n-Pr |
| 156 | J = J-2a, Q = C(OH)H, R$^1$ = H, R$^2$ = i-Pr |
| 157 | J = J-2a, Q = C(OH)H, R$^1$ = H, R$^2$ = CH$_2$OMe |
| 158 | J = J-2a, Q = C(OH)H, R$^1$ = H, R$^2$ = CH$_2$F |
| 159 | J = J-2a, Q = C(OH)H, R$^1$ = H, R$^2$ = CHF$_2$ |
| 160 | J = J-2a, Q = C(OH)H, R$^1$ = H, R$^2$ = CF$_3$ |
| 161 | J = J-2a, Q = C(OH)H, R$^1$ = H, R$^2$ = OMe |
| 162 | J = J-2a, Q = C(OH)H, R$^1$ = H, R$^2$ = OEt |
| 163 | J = J-2a, Q = C(OH)H, R$^1$ = H, R$^2$ = OCHF$_2$ |
| 164 | J = J-2a, Q = C(OH)H, R$^1$ = H, R$^2$ = OCH$_2$CF$_3$ |
| 165 | J = J-2a, Q = C(OH)H, R$^1$ = H, R$^2$ = NHMe |
| 166 | J = J-2a, Q = C(OH)H, R$^1$ = H, R$^2$ = NHEt |
| 167 | J = J-2a, Q = C(OH)H, R$^1$ = H, R$^2$ = NMe$_2$ |
| 168 | J = J-2a, Q = C(OH)H, R$^1$ = H, R$^2$ = NEt$_2$ |
| 169 | J = J-2a, Q = C(OH)H, R$^1$ = H, R$^2$ = NMeEt |
| 170 | J = J-2a, Q = C(OH)H, R$^1$ = H, R$^2$ = Cl |
| 171 | J = J-2a, Q = C(OH)H, R$^1$ = Me, R$^2$ = Me |
| 172 | J = J-2a, Q = C(OH)H, R$^1$ = Et, R$^2$ = Et |
| 173 | J = J-2a, Q = C(OH)H, R$^1$ = Me, R$^2$ = Cl |
| 174 | J = J-2a, Q = C(OH)H, R$^1$ = Cl, R$^2$ = Me |
| 175 | J = J-2a, Q = CHF, R$^1$ = Me, R$^2$ = H |
| 176 | J = J-2a, Q = CHF, R$^1$ = Et, R$^2$ = H |
| 177 | J = J-2a, Q = CHF, R$^1$ = n-Pr, R$^2$ = H |
| 178 | J = J-2a, Q = CHF, R$^1$ = i-Pr, R$^2$ = H |
| 179 | J = J-2a, Q = CHF, R$^1$ = CH$_2$OMe, R$^2$ = H |
| 180 | J = J-2a, Q = CHF, R$^1$ = CH$_2$F, R$^2$ = H |
| 181 | J = J-2a, Q = CHF, R$^1$ = CHF$_2$, R$^2$ = H |
| 182 | J = J-2a, Q = CHF, R$^1$ = CF$_3$, R$^2$ = H |
| 183 | J = J-2a, Q = CHF, R$^1$ = OMe, R$^2$ = H |
| 184 | J = J-2a, Q = CHF, R$^1$ = OEt, R$^2$ = H |
| 185 | J = J-2a, Q = CHF, R$^1$ = OCHF$_2$, R$^2$ = H |
| 186 | J = J-2a, Q = CHF, R$^1$ = OCH$_2$CF$_3$, R$^2$ = H |
| 187 | J = J-2a, Q = CHF, R$^1$ = NHMe, R$^2$ = H |
| 188 | J = J-2a, Q = CHF, R$^1$ = NHEt, R$^2$ = H |
| 189 | J = J-2a, Q = CHF, R$^1$ = NMe$_2$, R$^2$ = H |
| 190 | J = J-2a, Q = CHF, R$^1$ = NEt$_2$, R$^2$ = H |
| 191 | J = J-2a, Q = CHF, R$^1$ = NMeEt, R$^2$ = H |
| 192 | J = J-2a, Q = CHF, R$^1$ = Cl, R$^2$ = H |
| 193 | J = J-2a, Q = CHF, R$^1$ = Br, R$^2$ = H |
| 194 | J = J-2a, Q = CHF, R$^1$ = H, R$^2$ = Me |
| 195 | J = J-2a, Q = CHF, R$^1$ = H, R$^2$ = Et |
| 196 | J = J-2a, Q = CHF, R$^1$ = H, R$^2$ = n-Pr |
| 197 | J = J-2a, Q = CHF, R$^1$ = H, R$^2$ = i-Pr |
| 198 | J = J-2a, Q = CHF, R$^1$ = H, R$^2$ = CH$_2$OMe |
| 199 | J = J-2a, Q = CHF, R$^1$ = H, R$^2$ = CH$_2$F |
| 200 | J = J-2a, Q = CHF, R$^1$ = H, R$^2$ = CHF$_2$ |
| 201 | J = J-2a, Q = CHF, R$^1$ = H, R$^2$ = CF$_3$ |
| 202 | J = J-2a, Q = CHF, R$^1$ = H, R$^2$ = OMe |
| 203 | J = J-2a, Q = CHF, R$^1$ = H, R$^2$ = OEt |
| 204 | J = J-2a, Q = CHF, R$^1$ = H, R$^2$ = OCHF$_2$ |
| 205 | J = J-2a, Q = CHF, R$^1$ = H, R$^2$ = OCH$_2$CF$_3$ |
| 206 | J = J-2a, Q = CHF, R$^1$ = H, R$^2$ = NHMe |
| 207 | J = J-2a, Q = CHF, R$^1$ = H, R$^2$ = NHEt |
| 208 | J = J-2a, Q = CHF, R$^1$ = H, R$^2$ = NMe$_2$ |
| 209 | J = J-2a, Q = CHF, R$^1$ = H, R$^2$ = NEt$_2$ |
| 210 | J = J-2a, Q = CHF, R$^1$ = H, R$^2$ = NMeEt |
| 211 | J = J-2a, Q = CHF, R$^1$ = H, R$^2$ = Cl |
| 212 | J = J-2a, Q = CHF, R$^1$ = Me, R$^2$ = Me |
| 213 | J = J-2a, Q = CHF, R$^1$ = Et, R$^2$ = Et |
| 214 | J = J-2a, Q = CHF, R$^1$ = Me, R$^2$ = Cl |
| 215 | J = J-2a, Q = CHF, R$^1$ = Cl, R$^2$ = Me |
| 216 | J = J-2a, Q = CHF, R$^1$ = Cl, R$^2$ = Cl |
| 217 | J = J-2a, Q = CHF, R$^1$, R$^2$ = —(CH$_2$)$_3$— |
| 218 | J = J-2a, Q = CHF, R$^1$, R$^2$ = —(CH$_2$)$_4$— |
| 219 | J = J-2a, Q = S, R$^1$ = Me, R$^2$ = H |
| 220 | J = J-2a, Q = S, R$^1$ = Et, R$^2$ = H |
| 221 | J = J-2a, Q = S, R$^1$ = n-Pr, R$^2$ = H |
| 222 | J = J-2a, Q = S, R$^1$ = i-Pr, R$^2$ = H |
| 223 | J = J-2a, Q = S, R$^1$ = CH$_2$OMe, R$^2$ = H |
| 224 | J = J-2a, Q = S, R$^1$ = CH$_2$F, R$^2$ = H |
| 225 | J = J-2a, Q = S, R$^1$ = CHF$_2$, R$^2$ = H |
| 226 | J = J-2a, Q = S, R$^1$ = CF$_3$, R$^2$ = H |
| 227 | J = J-2a, Q = S, R$^1$ = OMe, R$^2$ = H |
| 228 | J = J-2a, Q = S, R$^1$ = OEt, R$^2$ = H |
| 229 | J = J-2a, Q = S, R$^1$ = OCHF$_2$, R$^2$ = H |
| 230 | J = J-2a, Q = S, R$^1$ = OCH$_2$CF$_3$, R$^2$ = H |
| 231 | J = J-2a, Q = S, R$^1$ = NHMe, R$^2$ = H |
| 232 | J = J-2a, Q = S, R$^1$ = NHEt, R$^2$ = H |
| 233 | J = J-2a, Q = S, R$^1$ = NMe$_2$, R$^2$ = H |
| 234 | J = J-2a, Q = S, R$^1$ = NEt$_2$, R$^2$ = H |
| 235 | J = J-2a, Q = S, R$^1$ = NMeEt, R$^2$ = H |
| 236 | J = J-2a, Q = S, R$^1$ = Cl, R$^2$ = H |
| 237 | J = J-2a, Q = S, R$^1$ = Br, R$^2$ = H |
| 238 | J = J-2a, Q = S, R$^1$ = H, R$^2$ = Me |
| 239 | J = J-2a, Q = S, R$^1$ = H, R$^2$ = Et |

TABLE 1450-continued

| Table | Row Heading |
|---|---|
| 240 | J = J-2a, Q = S, $R^1$ = H, $R^2$ = n-Pr |
| 241 | J = J-2a, Q = S, $R^1$ = H, $R^2$ = i-Pr |
| 242 | J = J-2a, Q = S, $R^1$ = H, $R^2$ = $CH_2OMe$ |
| 243 | J = J-2a, Q = S, $R^1$ = H, $R^2$ = $CH_2F$ |
| 244 | J = J-2a, Q = S, $R^1$ = H, $R^2$ = $CHF_2$ |
| 245 | J = J-2a, Q = S, $R^1$ = H, $R^2$ = $CF_3$ |
| 246 | J = J-2a, Q = S, $R^1$ = H, $R^2$ = OMe |
| 247 | J = J-2a, Q = S, $R^1$ = H, $R^2$ = OEt |
| 248 | J = J-2a, Q = S, $R^1$ = H, $R^2$ = $OCHF_2$ |
| 249 | J = J-2a, Q = S, $R^1$ = H, $R^2$ = $OCH_2CF_3$ |
| 250 | J = J-2a, Q = S, $R^1$ = H, $R^2$ = NHMe |
| 251 | J = J-2a, Q = S, $R^1$ = H, $R^2$ = NHEt |
| 252 | J = J-2a, Q = S, $R^1$ = H, $R^2$ = $NMe_2$ |
| 253 | J = J-2a, Q = S, $R^1$ = H, $R^2$ = $NEt_2$ |
| 254 | J = J-2a, Q = S, $R^1$ = H, $R^2$ = NMeEt |
| 255 | J = J-2a, Q = S, $R^1$ = H, $R^2$ = Cl |
| 256 | J = J-2a, Q = S, $R^1$ = Me, $R^2$ = Me |
| 257 | J = J-2a, Q = S, $R^1$ = Et, $R^2$ = Et |
| 258 | J = J-2a, Q = S, $R^1$ = Me, $R^2$ = Cl |
| 259 | J = J-2a, Q = S, $R^1$ = Cl, $R^2$ = Me |
| 260 | J = J-2a, Q = NH, $R^1$ = Me, $R^2$ = H |
| 261 | J = J-2a, Q = NH, $R^1$ = Et, $R^2$ = H |
| 262 | J = J-2a, Q = NH, $R^1$ = n-Pr, $R^2$ = H |
| 263 | J = J-2a, Q = NH, $R^1$ = i-Pr, $R^2$ = H |
| 264 | J = J-2a, Q = NH, $R^1$ = $CH_2OMe$, $R^2$ = H |
| 265 | J = J-2a, Q = NH, $R^1$ = $CH_2F$, $R^2$ = H |
| 266 | J = J-2a, Q = NH, $R^1$ = $NH_2$, $R^2$ = H |
| 267 | J = J-2a, Q = NH, $R^1$ = $CF_3$, $R^2$ = H |
| 268 | J = J-2a, Q = NH, $R^1$ = OMe, $R^2$ = H |
| 269 | J = J-2a, Q = NH, $R^1$ = OEt, $R^2$ = H |
| 270 | J = J-2a, Q = NH, $R^1$ = $OCHF_2$, $R^2$ = H |
| 271 | J = J-2a, Q = NH, $R^1$ = $OCH_2CF_3$, $R^2$ = H |
| 272 | J = J-2a, Q = NH, $R^1$ = NHMe, $R^2$ = H |
| 273 | J = J-2a, Q = NH, $R^1$ = NHEt, $R^2$ = H |
| 274 | J = J-2a, Q = NH, $R^1$ = $NMe_2$, $R^2$ = H |
| 275 | J = J-2a, Q = NH, $R^1$ = $NEt_2$, $R^2$ = H |
| 276 | J = J-2a, Q = NH, $R^1$ = NMeEt, $R^2$ = H |
| 277 | J = J-2a, Q = NH, $R^1$ = Cl, $R^2$ = H |
| 278 | J = J-2a, Q = NH, $R^1$ = Br, $R^2$ = H |
| 279 | J = J-2a, Q = NH, $R^1$ = H, $R^2$ = Me |
| 280 | J = J-2a, Q = NH, $R^1$ = H, $R^2$ = Et |
| 281 | J = J-2a, Q = NH, $R^1$ = H, $R^2$ = n-Pr |
| 282 | J = J-2a, Q = NH, $R^1$ = H, $R^2$ = i-Pr |
| 283 | J = J-2a, Q = NH, $R^1$ = H, $R^2$ = $CH_2OMe$ |
| 284 | J = J-2a, Q = NH, $R^1$ = H, $R^2$ = $CH_2F$ |
| 285 | J = J-2a, Q = NH, $R^1$ = H, $R^2$ = $CHF_2$ |
| 286 | J = J-2a, Q = NH, $R^1$ = H, $R^2$ = $CF_3$ |
| 287 | J = J-2a, Q = NH, $R^1$ = H, $R^2$ = OMe |
| 288 | J = J-2a, Q = NH, $R^1$ = H, $R^2$ = OEt |
| 289 | J = J-2a, Q = NH, $R^1$ = H, $R^2$ = $OCHF_2$ |
| 290 | J = J-2a, Q = NH, $R^1$ = H, $R^2$ = $OCH_2CF_3$ |
| 291 | J = J-2a, Q = NH, $R^1$ = H, $R^2$ = NHMe |
| 292 | J = J-2a, Q = NH, $R^1$ = H, $R^2$ = NHEt |
| 293 | J = J-2a, Q = NH, $R^1$ = H, $R^2$ = $NMe_2$ |
| 294 | J = J-2a, Q = NH, $R^1$ = H, $R^2$ = $NEt_2$ |
| 295 | J = J-2a, Q = NH, $R^1$ = H, $R^2$ = NMeEt |
| 296 | J = J-2a, Q = NH, $R^1$ = H, $R^2$ = Cl |
| 297 | J = J-2a, Q = NH, $R^1$ = Me, $R^2$ = Me |
| 298 | J = J-2a, Q = NH, $R^1$ = Et, $R^2$ = Et |
| 299 | J = J-2a, Q = NH, $R^1$ = Me, $R^2$ = Cl |
| 300 | J = J-2a, Q = NH, $R^1$ = Cl, $R^2$ = Me |
| 301 | J = J-2a, Q = NH, $R^1$ = Cl, $R^2$ = Cl |
| 302 | J = J-2a, Q = NH, $R^1$, $R^2$ = —$(CH_2)_3$— |
| 303 | J = J-2a, Q = NH, $R^1$, $R^2$ = —$(CH_2)_4$— |
| 304 | J = J-2b, Q = O, $R^1$ = Me, $R^2$ = H |
| 305 | J = J-2b, Q = O, $R^1$ = Et, $R^2$ = H |
| 306 | J = J-2b, Q = O, $R^1$ = n-Pr, $R^2$ = H |
| 307 | J = J-2b, Q = O, $R^1$ = i-Pr, $R^2$ = H |
| 308 | J = J-2b, Q = O, $R^1$ = $CH_2OMe$, $R^2$ = H |
| 309 | J = J-2b, Q = O, $R^1$ = $CH_2F$, $R^2$ = H |
| 310 | J = J-2b, Q = O, $R^1$ = $CHF_2$, $R^2$ = H |
| 311 | J = J-2b, Q = O, $R^1$ = $CF_3$, $R^2$ = H |
| 312 | J = J-2b, Q = O, $R^1$ = OMe, $R^2$ = H |
| 313 | J = J-2b, Q = O, $R^1$ = OEt, $R^2$ = H |
| 314 | J = J-2b, Q = O, $R^1$ = $OCHF_2$, $R^2$ = H |
| 315 | J = J-2b, Q = O, $R^1$ = $OCH_2CF_3$, $R^2$ = H |
| 316 | J = J-2b, Q = O, $R^1$ = NHMe, $R^2$ = H |
| 317 | J = J-2b, Q = O, $R^1$ = NHEt, $R^2$ = H |
| 318 | J = J-2b, Q = O, $R^1$ = $NMe_2$, $R^2$ = H |
| 319 | J = J-2b, Q = O, $R^1$ = $NEt_2$, $R^2$ = H |
| 320 | J = J-2b, Q = O, $R^1$ = NMeEt, $R^2$ = H |
| 321 | J = J-2b, Q = O, $R^1$ = Cl, $R^2$ = H |
| 322 | J = J-2b, Q = O, $R^1$ = Br, $R^2$ = H |
| 323 | J = J-2b, Q = O, $R^1$ = H, $R^2$ = Me |
| 324 | J = J-2b, Q = O, $R^1$ = H, $R^2$ = Et |
| 325 | J = J-2b, Q = O, $R^1$ = H, $R^2$ = n-Pr |
| 326 | J = J-2b, Q = O, $R^1$ = H, $R^2$ = i-Pr |
| 327 | J = J-2b, Q = O, $R^1$ = H, $R^2$ = $CH_2OMe$ |
| 328 | J = J-2b, Q = O, $R^1$ = H, $R^2$ = $CH_2F$ |
| 329 | J = J-2b, Q = O, $R^1$ = H, $R^2$ = $CHF_2$ |
| 330 | J = J-2b, Q = O, $R^1$ = H, $R^2$ = $CF_3$ |
| 331 | J = J-2b, Q = O, $R^1$ = H, $R^2$ = OMe |
| 332 | J = J-2b, Q = O, $R^1$ = H, $R^2$ = OEt |
| 333 | J = J-2b, Q = O, $R^1$ = H, $R^2$ = $OCHF_2$ |
| 334 | J = J-2b, Q = O, $R^1$ = H, $R^2$ = $OCH_2CF_3$ |
| 335 | J = J-2b, Q = O, $R^1$ = H, $R^2$ = NHMe |
| 336 | J = J-2b, Q = O, $R^1$ = H, $R^2$ = NHEt |
| 337 | J = J-2b, Q = O, $R^1$ = H, $R^2$ = $NMe_2$ |
| 338 | J = J-2b, Q = O, $R^1$ = H, $R^2$ = $NEt_2$ |
| 339 | J = J-2b, Q = O, $R^1$ = H, $R^2$ = NMeEt |
| 340 | J = J-2b, Q = O, $R^1$ = H, $R^2$ = Cl |
| 341 | J = J-2b, Q = O, $R^1$ = H, $R^2$ = Br |
| 342 | J = J-2b, Q = O, $R^1$ = Me, $R^2$ = Me |
| 343 | J = J-2b, Q = O, $R^1$ = Et, $R^2$ = Et |
| 344 | J = J-2b, Q = O, $R^1$ = Me, $R^2$ = Cl |
| 345 | J = J-2b, Q = O, $R^1$ = Cl, $R^2$ = Me |
| 346 | J = J-2b, Q = O, $R^1$ = Cl, $R^2$ = Cl |
| 347 | J = J-2b, Q = O, $R^1$, $R^2$ = —$(CH_2)_3$— |
| 348 | J = J-2b, Q = O, $R^1$, $R^2$ = —$(CH_2)_4$— |
| 349 | J = J-2b, Q = $CH_2$, $R^1$ = Me, $R^2$ = H |
| 350 | J = J-2b, Q = $CH_2$, $R^1$ = Et, $R^2$ = H |
| 351 | J = J-2b, Q = $CH_2$, $R^1$ = n-Pr, $R^2$ = H |
| 352 | J = J-2b, Q = $CH_2$, $R^1$ = i-Pr, $R^2$ = H |
| 353 | J = J-2b, Q = $CH_2$, $R^1$ = $CH_2OMe$, $R^2$ = H |
| 354 | J = J-2b, Q = $CH_2$, $R^1$ = $CH_2F$, $R^2$ = H |
| 355 | J = J-2b, Q = $CH_2$, $R^1$ = $CHF_2$, $R^2$ = H |
| 356 | J = J-2b, Q = $CH_2$, $R^1$ = $CF_3$, $R^2$ = H |
| 357 | J = J-2b, Q = $CH_2$, $R^1$ = OMe, $R^2$ = H |
| 358 | J = J-2b, Q = $CH_2$, $R^1$ = OEt, $R^2$ = H |
| 359 | J = J-2b, Q = $CH_2$, $R^1$ = $OCHF_2$, $R^2$ = H |
| 360 | J = J-2b, Q = $CH_2$, $R^1$ = $OCH_2CF_3$, $R^2$ = H |
| 361 | J = J-2b, Q = $CH_2$, $R^1$ = NHMe, $R^2$ = H |
| 362 | J = J-2b, Q = $CH_2$, $R^1$ = NHEt, $R^2$ = H |
| 363 | J = J-2b, Q = $CH_2$, $R^1$ = $NMe_2$, $R^2$ = H |
| 364 | J = J-2b, Q = $CH_2$, $R^1$ = $NEt_2$, $R^2$ = H |
| 365 | J = J-2b, Q = $CH_2$, $R^1$ = NMeEt, $R^2$ = H |
| 366 | J = J-2b, Q = $CH_2$, $R^1$ = Cl, $R^2$ = H |
| 367 | J = J-2b, Q = $CH_2$, $R^1$ = Br, $R^2$ = H |
| 368 | J = J-2b, Q = $CH_2$, $R^1$ = H, $R^2$ = Me |
| 369 | J = J-2b, Q = $CH_2$, $R^1$ = H, $R^2$ = Et |
| 370 | J = J-2b, Q = $CH_2$, $R^1$ = H, $R^2$ = n-Pr |
| 371 | J = J-2b, Q = $CH_2$, $R^1$ = H, $R^2$ = i-Pr |
| 372 | J = J-2b, Q = $CH_2$, $R^1$ = H, $R^2$ = $CH_2OMe$ |
| 373 | J = J-2b, Q = $CH_2$, $R^1$ = H, $R^2$ = $CH_2F$ |
| 374 | J = J-2b, Q = $CH_2$, $R^1$ = H, $R^2$ = $CHF_2$ |
| 375 | J = J-2b, Q = $CH_2$, $R^1$ = H, $R^2$ = $CF_3$ |
| 376 | J = J-2b, Q = $CH_2$, $R^1$ = H, $R^2$ = OMe |
| 377 | J = J-2b, Q = $CH_2$, $R^1$ = H, $R^2$ = OEt |
| 378 | J = J-2b, Q = $CH_2$, $R^1$ = H, $R^2$ = $OCHF_2$ |
| 379 | J = J-2b, Q = $CH_2$, $R^1$ = H, $R^2$ = $OCH_2CF_3$ |
| 380 | J = J-2b, Q = $CH_2$, $R^1$ = H, $R^2$ = NHMe |
| 381 | J = J-2b, Q = $CH_2$, $R^1$ = H, $R^2$ = NHEt |
| 382 | J = J-2b, Q = $CH_2$, $R^1$ = H, $R^2$ = $NMe_2$ |
| 383 | J = J-2b, Q = $CH_2$, $R^1$ = H, $R^2$ = $NEt_2$ |
| 384 | J = J-2b, Q = $CH_2$, $R^1$ = H, $R^2$ = NMeEt |
| 385 | J = J-2b, Q = $CH_2$, $R^1$ = H, $R^2$ = Cl |
| 386 | J = J-2b, Q = $CH_2$, $R^1$ = Me, $R^2$ = Me |
| 387 | J = J-2b, Q = $CH_2$, $R^1$ = Et, $R^2$ = Et |
| 388 | J = J-2b, Q = $CH_2$, $R^1$ = Me, $R^2$ = Cl |
| 389 | J = J-2b, Q = $CH_2$, $R^1$ = Cl, $R^2$ = Me |
| 390 | J = J-2b, Q = $CH_2$, $R^1$ = Cl, $R^2$ = Cl |
| 391 | J = J-2b, Q = $CH_2$, $R^1$, $R^2$ = —$(CH_2)_3$— |
| 392 | J = J-2b, Q = $CH_2$, $R^1$, $R^2$ = —$(CH_2)_4$— |
| 393 | J = J-2b, Q = C(=O), $R^1$ = Me, $R^2$ = H |
| 394 | J = J-2b, Q = C(=O), $R^1$ = Et, $R^2$ = H |
| 395 | J = J-2b, Q = C(=O), $R^1$ = n-Pr, $R^2$ = H |

TABLE 1450-continued

| Table | Row Heading |
|---|---|
| 396 | J = J-2b, Q = C(=O), R$^1$ = i-Pr, R$^2$ = H |
| 397 | J = J-2b, Q = C(=O), R$^1$ = CH$_2$OMe, R$^2$ = H |
| 398 | J = J-2b, Q = C(=O), R$^1$ = CH$_2$F, R$^2$ = H |
| 399 | J = J-2b, Q = C(=O), R$^1$ = CHF$_2$, R$^2$ = H |
| 400 | J = J-2b, Q = C(=O), R$^1$ = CF$_3$, R$^2$ = H |
| 401 | J = J-2b, Q = C(=O), R$^1$ = OMe, R$^2$ = H |
| 402 | J = J-2b, Q = C(=O), R$^1$ = OEt, R$^2$ = H |
| 403 | J = J-2b, Q = C(=O), R$^1$ = OCHF$_2$, R$^2$ = H |
| 404 | J = J-2b, Q = C(=O), R$^1$ = OCH$_2$CF$_3$, R$^2$ = H |
| 405 | J = J-2b, Q = C(=O), R$^1$ = NHMe, R$^2$ = H |
| 406 | J = J-2b, Q = C(=O), R$^1$ = NHEt, R$^2$ = H |
| 407 | J = J-2b, Q = C(=O), R$^1$ = NMe$_2$, R$^2$ = H |
| 408 | J = J-2b, Q = C(=O), R$^1$ = NEt$_2$, R$^2$ = H |
| 409 | J = J-2b, Q = C(=O), R$^1$ = NMeEt, R$^2$ = H |
| 410 | J = J-2b, Q = C(=O), R$^1$ = Cl, R$^2$ = H |
| 411 | J = J-2b, Q = C(=O), R$^1$ = Br, R$^2$ = H |
| 412 | J = J-2b, Q = C(=O), R$^1$ = H, R$^2$ = Me |
| 413 | J = J-2b, Q = C(=O), R$^1$ = H, R$^2$ = Et |
| 414 | J = J-2b, Q = C(=O), R$^1$ = H, R$^2$ = n-Pr |
| 415 | J = J-2b, Q = C(=O), R$^1$ = H, R$^2$ = i-Pr |
| 416 | J = J-2b, Q = C(=O), R$^1$ = H, R$^2$ = CH$_2$OMe |
| 417 | J = J-2b, Q = C(=O), R$^1$ = H, R$^2$ = CH$_2$F |
| 418 | J = J-2b, Q = C(=O), R$^1$ = H, R$^2$ = CHF$_2$ |
| 419 | J = J-2b, Q = C(=O), R$^1$ = H, R$^2$ = CF$_3$ |
| 420 | J = J-2b, Q = C(=O), R$^1$ = H, R$^2$ = OMe |
| 421 | J = J-2b, Q = C(=O), R$^1$ = H, R$^2$ = OEt |
| 422 | J = J-2b, Q = C(=O), R$^1$ = H, R$^2$ = OCHF$_2$ |
| 423 | J = J-2b, Q = C(=O), R$^1$ = H, R$^2$ = OCH$_2$CF$_3$ |
| 424 | J = J-2b, Q = C(=O), R$^1$ = H, R$^2$ = NHMe |
| 425 | J = J-2b, Q = C(=O), R$^1$ = H, R$^2$ = NHEt |
| 426 | J = J-2b, Q = C(=O), R$^1$ = H, R$^2$ = NMe$_2$ |
| 427 | J = J-2b, Q = C(=O), R$^1$ = H, R$^2$ = NEt$_2$ |
| 428 | J = J-2b, Q = C(=O), R$^1$ = H, R$^2$ = NMeEt |
| 429 | J = J-2b, Q = C(=O), R$^1$ = H, R$^2$ = Cl |
| 430 | J = J-2b, Q = C(=O), R$^1$ = Me, R$^2$ = Me |
| 431 | J = J-2b, Q = C(=O), R$^1$ = Et, R$^2$ = Et |
| 432 | J = J-2b, Q = C(=O), R$^1$ = Me, R$^2$ = Cl |
| 433 | J = J-2b, Q = C(=O), R$^1$ = Cl, R$^2$ = Me |
| 434 | J = J-2b, Q = C(=O), R$^1$ = Cl, R$^2$ = Cl |
| 435 | J = J-2b, Q = C(=O), R$^1$, R$^2$ = —(CH$_2$)$_3$— |
| 436 | J = J-2b, Q = C(=O), R$^1$, R$^2$ = —(CH$_2$)$_4$— |
| 437 | J = J-2b, Q = C(OH)H, R$^1$ = Me, R$^2$ = H |
| 438 | J = J-2b, Q = C(OH)H, R$^1$ = Et, R$^2$ = H |
| 439 | J = J-2b, Q = C(OH)H, R$^1$ = n-Pr, R$^2$ = H |
| 440 | J = J-2b, Q = C(OH)H, R$^1$ = i-Pr, R$^2$ = H |
| 441 | J = J-2b, Q = C(OH)H, R$^1$ = CH$_2$OMe, R$^2$ = H |
| 442 | J = J-2b, Q = C(OH)H, R$^1$ = CH$_2$F, R$^2$ = H |
| 443 | J = J-2b, Q = C(OH)H, R1 = CHF$_2$, R$^2$ = H |
| 444 | J = J-2b, Q = C(OH)H, R$^1$ = CF$_3$, R$^2$ = H |
| 445 | J = J-2b, Q = C(OH)H, R$^1$ = OMe, R$^2$ = H |
| 446 | J = J-2b, Q = C(OH)H, R$^1$ = OEt, R$^2$ = H |
| 447 | J = J-2b, Q = C(OH)H, R$^1$ = OCHF$_2$, R$^2$ = H |
| 448 | J = J-2b, Q = C(OH)H, R$^1$ = OCH$_2$CF$_3$, R$^2$ = H |
| 449 | J = J-2b, Q = C(OH)H, R$^1$ = NHMe, R$^2$ = H |
| 450 | J = J-2b, Q = C(OH)H, R$^1$ = NHEt, R$^2$ = H |
| 451 | J = J-2b, Q = C(OH)H, R$^1$ = NMe$_2$, R$^2$ = H |
| 452 | J = J-2b, Q = C(OH)H, R$^1$ = NEt$_2$, R$^2$ = H |
| 453 | J = J-2b, Q = C(OH)H, R$^1$ = NMeEt, R$^2$ = H |
| 454 | J = J-2b, Q = C(OH)H, R$^1$ = Cl, R$^2$ = H |
| 455 | J = J-2b, Q = C(OH)H, R$^1$ = Br, R$^2$ = H |
| 456 | J = J-2b, Q = C(OH)H, R$^1$ = H, R$^2$ = Me |
| 457 | J = J-2b, Q = C(OH)H, R$^1$ = H, R$^2$ = Et |
| 458 | J = J-2b, Q = C(OH)H, R$^1$ = H, R$^2$ = n-Pr |
| 459 | J = J-2b, Q = C(OH)H, R$^1$ = H, R$^2$ = i-Pr |
| 460 | J = J-2b, Q = C(OH)H, R$^1$ = H, R$^2$ = CH$_2$OMe |
| 461 | J = J-2b, Q = C(OH)H, R$^1$ = H, R$^2$ = CH$_2$F |
| 462 | J = J-2b, Q = C(OH)H, R$^1$ = H, R$^2$ = CHF$_2$ |
| 463 | J = J-2b, Q = C(OH)H, R$^1$ = H, R$^2$ = CF$_3$ |
| 464 | J = J-2b, Q = C(OH)H, R$^1$ = H, R$^2$ = OMe |
| 465 | J = J-2b, Q = C(OH)H, R$^1$ = H, R$^2$ = OEt |
| 466 | J = J-2b, Q = C(OH)H, R$^1$ = H, R$^2$ = OCHF$_2$ |
| 467 | J = J-2b, Q = C(OH)H, R$^1$ = H,R$^2$ = OCH$_2$CF$_3$ |
| 468 | J = J-2b, Q = C(OH)H, R$^1$ = H, R$^2$ = NHMe |
| 469 | J = J-2b, Q = C(OH)H, R$^1$ = H, R$^2$ = NHEt |
| 470 | J = J-2b, Q = C(OH)H, R$^1$ = H, R$^2$ = NMe$_2$ |
| 471 | J = J-2b, Q = C(OH)H, R$^1$ = H, R$^2$ = NEt$_2$ |
| 472 | J = J-2b, Q = C(OH)H, R$^1$ = H, R$^2$ = NMeEt |
| 473 | J = J-2b, Q = C(OH)H, R$^1$ = H, R$^2$ = Cl |
| 474 | J = J-2b, Q = C(OH)H, R$^1$ = Me, R$^2$ = Me |
| 475 | J = J-2b, Q = C(OH)H, R$^1$ = Et, R$^2$ = Et |
| 476 | J = J-2b, Q = C(OH)H, R$^1$ = Me, R$^2$ = Cl |
| 477 | J = J-2b, Q = C(OH)H, R$^1$ = Cl, R$^2$ = Me |
| 478 | J = J-2b, Q = CHF, R$^1$ = Me, R$^2$ = H |
| 479 | J = J-2b, Q = CHF, R$^1$ = Et, R$^2$ = H |
| 480 | J = J-2b, Q = CHF, R$^1$ = n-Pr, R$^2$ = H |
| 481 | J = J-2b, Q = CHF, R$^1$ = i-Pr, R$^2$ = H |
| 482 | J = J-2b, Q = CHF, R$^1$ = CH$_2$OMe, R$^2$ = H |
| 483 | J = J-2b, Q = CHF, R$^1$ = CH$_2$F, R$^2$ = H |
| 484 | J = J-2b, Q = CHF, R$^1$ = CHF$_2$, R$^2$ = H |
| 485 | J = J-2b, Q = CHF, R$^1$ = CF$_3$, R$^2$ = H |
| 486 | J = J-2b, Q = CHF, R$^1$ = OMe, R$^2$ = H |
| 487 | J = J-2b, Q = CHF, R$^1$ = OEt, R$^2$ = H |
| 488 | J = J-2b, Q = CHF, R$^1$ = OCHF$_2$, R$^2$ = H |
| 489 | J = J-2b, Q = CHF, R$^1$ = OCH$_2$CF$_3$, R$^2$ = H |
| 490 | J = J-2b, Q = CHF, R$^1$ = NHMe, R$^2$ = H |
| 491 | J = J-2b, Q = CHF, R$^1$ = NHEt, R$^2$ = H |
| 492 | J = J-2b, Q = CHF, R$^1$ = NMe$_2$, R$^2$ = H |
| 493 | J = J-2b, Q = CHF, R$^1$ = NEt$_2$, R$^2$ = H |
| 494 | J = J-2b, Q = CHF, R$^1$ = NMeEt, R$^2$ = H |
| 495 | J = J-2b, Q = CHF, R$^1$ = Cl, R$^2$ = H |
| 496 | J = J-2b, Q = CHF, R$^1$ = Br, R$^2$ = H |
| 497 | J = J-2b, Q = CHF, R$^1$ = H, R$^2$ = Me |
| 498 | J = J-2b, Q = CHF, R$^1$ = H, R$^2$ = Et |
| 499 | J = J-2b, Q = CHF, R$^1$ = H, R$^2$ = n-Pr |
| 500 | J = J-2b, Q = CHF, R$^1$ = H, R$^2$ = i-Pr |
| 501 | J = J-2b, Q = CHF, R$^1$ = H, R$^2$ = CH$_2$OMe |
| 502 | J = J-2b, Q = CHF, R$^1$ = H, R$^2$ = CH$_2$F |
| 503 | J = J-2b, Q = CHF, R$^1$ = H, R$^2$ = CHF$_2$ |
| 504 | J = J-2b, Q = CHF, R$^1$ = H, R$^2$ = CF$_3$ |
| 505 | J = J-2b, Q = CHF, R$^1$ = H, R$^2$ = OMe |
| 506 | J = J-2b, Q = CHF, R$^1$ = H, R$^2$ = OEt |
| 507 | J = J-2b, Q = CHF, R$^1$ = H, R$^2$ = OCHF$_2$ |
| 508 | J = J-2b, Q = CHF, R$^1$ = H, R$^2$ = OCH$_2$CF$_3$ |
| 509 | J = J-2b, Q = CHF, R$^1$ = H, R$^2$ = NHMe |
| 510 | J = J-2b, Q = CHF, R$^1$ = H, R$^2$ = NHEt |
| 511 | J = J-2b, Q = CHF, R$^1$ = H, R$^2$ = NMe$_2$ |
| 512 | J = J-2b, Q = CHF, R$^1$ = H, R$^2$ = NEt$_2$ |
| 513 | J = J-2b, Q = CHF, R$^1$ = H, R$^2$ = NMeEt |
| 514 | J = J-2b, Q = CHF, R$^1$ = H, R$^2$ = Cl |
| 515 | J = J-2b, Q = CHF, R$^1$ = Me, R$^2$ = Me |
| 516 | J = J-2b, Q = CHF, R$^1$ = Et, R$^2$ = Et |
| 517 | J = J-2b, Q = CHF, R$^1$ = Me, R$^2$ = Cl |
| 518 | J = J-2b, Q = CHF, R$^1$ = Cl, R$^2$ = Me |
| 519 | J = J-2b, Q = CHF, R$^1$ = Cl, R$^2$ = Cl |
| 520 | J = J-2b, Q = CHF, R$^1$, R$^2$ = —(CH$_2$)$_3$— |
| 521 | J = J-2b, Q = CHF, R$^1$, R$^2$ = —(CH$_2$)$_4$— |
| 522 | J = J-2b, Q = S, R$^1$ = Me, R$^2$ = H |
| 523 | J = J-2b, Q = S, R$^1$ = Et, R$^2$ = H |
| 524 | J = J-2b, Q = S, R$^1$ = n-Pr, R$^2$ = H |
| 525 | J = J-2b, Q = S, R$^1$ = i-Pr, R$^2$ = H |
| 526 | J = J-2b, Q = S, R$^1$ = CH$_2$OMe, R$^2$ = H |
| 527 | J = J-2b, Q = S, R$^1$ = CH$_2$F, R$^2$ = H |
| 528 | J = J-2b, Q = S, R$^1$ = CHF$_2$, R$^2$ = H |
| 529 | J = J-2b, Q = S, R$^1$ = CF$_3$, R$^2$ = H |
| 530 | J = J-2b, Q = S, R$^1$ = OMe, R$^2$ = H |
| 531 | J = J-2b, Q = S, R$^1$ = OEt, R$^2$ = H |
| 532 | J = J-2b, Q = S, R$^1$ = OCHF$_2$, R$^2$ = H |
| 533 | J = J-2b, Q = S, R$^1$ = OCH$_2$CF$_3$, R$^2$ = H |
| 534 | J = J-2b, Q = S, R$^1$ = NHMe, R$^2$ = H |
| 535 | J = J-2b, Q = S, R$^1$ = NHEt, R$^2$ = H |
| 536 | J = J-2b, Q = S, R$^1$ = NMe$_2$, R$^2$ = H |
| 537 | J = J-2b, Q = S, R$^1$ = NEt$_2$, R$^2$ = H |
| 538 | J = J-2b, Q = S, R$^1$ = NMeEt, R$^2$ = H |
| 539 | J = J-2b, Q = S, R$^1$ = Cl, R$^2$ = H |
| 540 | J = J-2b, Q = S, R$^1$ = Br, R$^2$ = H |
| 541 | J = J-2b, Q = S, R$^1$ = H, R$^2$ = Me |
| 542 | J = J-2b, Q = S, R$^1$ = H, R$^2$ = Et |
| 543 | J = J-2b, Q = S, R$^1$ = H, R$^2$ = n-Pr |
| 544 | J = J-2b, Q = S, R$^1$ = H, R$^2$ = i-Pr |
| 545 | J = J-2b, Q = S, R$^1$ = H, R$^2$ = CH$_2$OMe |
| 546 | J = J-2b, Q = S, R$^1$ = H, R$^2$ = CH$_2$F |
| 547 | J = J-2b, Q = S, R$^1$ = H, R$^2$ = CHF$_2$ |
| 548 | J = J-2b, Q = S, R$^1$ = H, R$^2$ = CF$_3$ |
| 549 | J = J-2b, Q = S, R$^1$ = H, R$^2$ = OMe |
| 550 | J = J-2b, Q = S, R$^1$ = H, R$^2$ = OEt |
| 551 | J = J-2b, Q = S, R$^1$ = H, R$^2$ = OCHF$_2$ |

TABLE 1450-continued

| Table | Row Heading |
|---|---|
| 552 | J = J-2b, Q = S, R$^1$ = H, R$^2$ = OCH$_2$CF$_3$ |
| 553 | J = J-2b, Q = S, R$^1$ = H, R$^2$ = NHMe |
| 554 | J = J-2b, Q = S, R$^1$ = H, R$^2$ = NHEt |
| 555 | J = J-2b, Q = S, R$^1$ = H, R$^2$ = NMe$_2$ |
| 556 | J = J-2b, Q = S, R$^1$ = H, R$^2$ = NEt$_2$ |
| 557 | J = J-2b, Q = S, R$^1$ = H, R$^2$ = NMeEt |
| 558 | J = J-2b, Q = S, R$^1$ = H, R$^2$ = Cl |
| 559 | J = J-2b, Q = S, R$^1$ = Me, R$^2$ = Me |
| 560 | J = J-2b, Q = S, R$^1$ = Et, R$^2$ = Et |
| 561 | J = J-2b, Q = S, R$^1$ = Me, R$^2$ = Cl |
| 562 | J = J-2b, Q = S, R$^1$ = Cl, R$^2$ = Me |
| 563 | J = J-2b, Q = NH, R$^1$ = Me, R$^2$ = H |
| 564 | J = J-2b, Q = NH, R$^1$ = Et, R$^2$ = H |
| 565 | J = J-2b, Q = NH, R$^1$ = n-Pr, R$^2$ = H |
| 566 | J = J-2b, Q = NH, R$^1$ = i-Pr, R$^2$ = H |
| 567 | J = J-2b, Q = NH, R$^1$ = CH$_2$OMe, R$^2$ = H |
| 568 | J = J-2b, Q = NH, R$^1$ = CH$_2$F, R$^2$ = H |
| 569 | J = J-2b, Q = NH, R$^1$ = NH$_2$, R$^2$ = H |
| 570 | J = J-2b, Q = NH, R$^1$ = CF$_3$, R$^2$ = H |
| 571 | J = J-2b, Q = NH, R$^1$ = OMe, R$^2$ = H |
| 572 | J = J-2b, Q = NH, R$^1$ = OEt, R$^2$ = H |
| 573 | J = J-2b, Q = NH, R$^1$ = OCHF$_2$, R$^2$ = H |
| 574 | J = J-2b, Q = NH, R$^1$ = OCH$_2$CF$_3$, R$^2$ = H |
| 575 | J = J-2b, Q = NH, R$^1$ = NHMe, R$^2$ = H |
| 576 | J = J-2b, Q = NH, R$^1$ = NHEt, R$^2$ = H |
| 577 | J = J-2b, Q = NH, R$^1$ = NMe$_2$, R$^2$ = H |
| 578 | J = J-2b, Q = NH, R$^1$ = NEt$_2$, R$^2$ = H |
| 579 | J = J-2b, Q = NH, R$^1$ = NMeEt, R$^2$ = H |
| 580 | J = J-2b, Q = NH, R$^1$ = Cl, R$^2$ = H |
| 581 | J = J-2b, Q = NH, R$^1$ = Br, R$^2$ = H |
| 582 | J = J-2b, Q = NH, R$^1$ = H, R$^2$ = Me |
| 583 | J = J-2b, Q = NH, R$^1$ = H, R$^2$ = Et |
| 584 | J = J-2b, Q = NH, R$^1$ = H, R$^2$ = n-Pr |
| 585 | J = J-2b, Q = NH, R$^1$ = H, R$^2$ = i-Pr |
| 586 | J = J-2b, Q = NH, R$^1$ = H, R$^2$ = CH$_2$OMe |
| 587 | J = J-2b, Q = NH, R$^1$ = H, R$^2$ = CH$_2$F |
| 588 | J = J-2b, Q = NH, R$^1$ = H, R$^2$ = CHF$_2$ |
| 589 | J = J-2b, Q = NH, R$^1$ = H, R$^2$ = CF$_3$ |
| 590 | J = J-2b, Q = NH, R$^1$ = H, R$^2$ = OMe |
| 591 | J = J-2b, Q = NH, R$^1$ = H, R$^2$ = OEt |
| 592 | J = J-2b, Q = NH, R$^1$ = H, R$^2$ = OCHF$_2$ |
| 593 | J = J-2b, Q = NH, R$^1$ = H, R$^2$ = OCH$_2$CF$_3$ |
| 594 | J = J-2b, Q = NH, R$^1$ = H, R$^2$ = NHMe |
| 595 | J = J-2b, Q = NH, R$^1$ = H, R$^2$ = NHEt |
| 596 | J = J-2b, Q = NH, R$^1$ = H, R$^2$ = NMe$_2$ |
| 597 | J = J-2b, Q = NH, R$^1$ = H, R$^2$ = NEt$_2$ |
| 598 | J = J-2b, Q = NH, R$^1$ = H, R$^2$ = NMeEt |
| 599 | J = J-2b, Q = NH, R$^1$ = H, R$^2$ = Cl |
| 600 | J = J-2b, Q = NH, R$^1$ = Me, R$^2$ = Me |
| 601 | J = J-2b, Q = NH, R$^1$ = Et, R$^2$ = Et |
| 602 | J = J-2b, Q = NH, R$^1$ = Me, R$^2$ = Cl |
| 603 | J = J-2b, Q = NH, R$^1$ = Cl, R$^2$ = Me |
| 604 | J = J-2b, Q = NH, R$^1$ = Cl, R$^2$ = Cl |
| 605 | J = J-2b, Q = NH, R$^1$, R$^2$ = —(CH$_2$)$_3$— |
| 606 | J = J-2b, Q = NH, R$^1$, R$^2$ = —(CH$_2$)$_4$— |
| 607 | J = J-2c, Q = O, R$^1$ = Me, R$^2$ = H |
| 608 | J = J-2c, Q = O, R$^1$ = Et, R$^2$ = H |
| 609 | J = J-2c, Q = O, R$^1$ = n-Pr, R$^2$ = H |
| 610 | J = J-2c, Q = O, R$^1$ = i-Pr, R$^2$ = H |
| 611 | J = J-2c, Q = O, R$^1$ = CH$_2$OMe, R$^2$ = H |
| 612 | J = J-2c, Q = O, R$^1$ = CH$_2$F, R$^2$ = H |
| 613 | J = J-2c, Q = O, R$^1$ = CHF$_2$, R$^2$ = H |
| 614 | J = J-2c, Q = O, R$^1$ = CF$_3$, R$^2$ = H |
| 615 | J = J-2c, Q = O, R$^1$ = OMe, R$^2$ = H |
| 616 | J = J-2c, Q = O, R$^1$ = OEt, R$^2$ = H |
| 617 | J = J-2c, Q = O, R$^1$ = OCHF$_2$, R$^2$ = H |
| 618 | J = J-2c, Q = O, R$^1$ = OCH$_2$CF$_3$, R$^2$ = H |
| 619 | J = J-2c, Q = O, R$^1$ = NHMe, R$^2$ = H |
| 620 | J = J-2c, Q = O, R$^1$ = NHEt, R$^2$ = H |
| 621 | J = J-2c, Q = O, R$^1$ = NMe$_2$, R$^2$ = H |
| 622 | J = J-2c, Q = O, R$^1$ = NEt$_2$, R$^2$ = H |
| 623 | J = J-2c, Q = O, R$^1$ = NMeEt, R$^2$ = H |
| 624 | J = J-2c, Q = O, R$^1$ = Cl, R$^2$ = H |
| 625 | J = J-2c, Q = O, R$^1$ = Br, R$^2$ = H |
| 626 | J = J-2c, Q = O, R$^1$ = H, R$^2$ = Me |
| 627 | J = J-2c, Q = O, R$^1$ = H, R$^2$ = Et |
| 628 | J = J-2c, Q = O, R$^1$ = H, R$^2$ = n-Pr |
| 629 | J = J-2c, Q = O, R$^1$ = H, R$^2$ = i-Pr |
| 630 | J = J-2c, Q = O, R$^1$ = H, R$^2$ = CH$_2$OMe |
| 631 | J = J-2c, Q = O, R$^1$ = H, R$^2$ = CH$_2$F |
| 632 | J = J-2c, Q = O, R$^1$ = H, R$^2$ = CHF$_2$ |
| 633 | J = J-2c, Q = O, R$^1$ = H, R$^2$ = CF$_3$ |
| 634 | J = J-2c, Q = O, R$^1$ = H, R$^2$ = OMe |
| 635 | J = J-2c, Q = O, R$^1$ = H, R$^2$ = OEt |
| 636 | J = J-2c, Q = O, R$^1$ = H, R$^2$ = OCHF$_2$ |
| 637 | J = J-2c, Q = O, R$^1$ = H, R$^2$ = OCH$_2$CF$_3$ |
| 638 | J = J-2c, Q = O, R$^1$ = H, R$^2$ = NHMe |
| 639 | J = J-2c, Q = O, R$^1$ = H, R$^2$ = NHEt |
| 640 | J = J-2c, Q = O, R$^1$ = H, R$^2$ = NMe$_2$ |
| 641 | J = J-2c, Q = O, R$^1$ = H, R$^2$ = NEt$_2$ |
| 642 | J = J-2c, Q = O, R$^1$ = H, R$^2$ = NMeEt |
| 643 | J = J-2c, Q = O, R$^1$ = H, R$^2$ = Cl |
| 644 | J = J-2c, Q = O, R$^1$ = H, R$^2$ = Br |
| 645 | J = J-2c, Q = O, R$^1$ = Me, R$^2$ = Me |
| 646 | J = J-2c, Q = O, R$^1$ = Et, R$^2$ = Et |
| 647 | J = J-2c, Q = O, R$^1$ = Me, R$^2$ = Cl |
| 648 | J = J-2c, Q = O, R$^1$ = Cl, R$^2$ = Me |
| 649 | J = J-2c, Q = O, R$^1$ = Cl, R$^2$ = Cl |
| 650 | J = J-2c, Q = O, R$^1$, R$^2$ = —(CH$_2$)$_3$— |
| 651 | J = J-2c, Q = O, R$^1$, R$^2$ = —(CH$_2$)$_4$— |
| 652 | J = J-2c, Q = CH$_2$, R$^1$ = Me, R$^2$ = H |
| 653 | J = J-2c, Q = CH$_2$, R$^1$ = Et, R$^2$ = H |
| 654 | J = J-2c, Q = CH$_2$, R$^1$ = n-Pr, R$^2$ = H |
| 655 | J = J-2c, Q = CH$_2$, R$^1$ = i-Pr, R$^2$ = H |
| 656 | J = J-2c, Q = CH$_2$, R$^1$ = CH$_2$OMe, R$^2$ = H |
| 657 | J = J-2c, Q = CH$_2$, R$^1$ = CH$_2$F, R$^2$ = H |
| 658 | J = J-2c, Q = CH$_2$, R$^1$ = CHF$_2$, R$^2$ = H |
| 659 | J = J-2c, Q = CH$_2$, R$^1$ = CF$_3$, R$^2$ = H |
| 660 | J = J-2c, Q = CH$_2$, R$^1$ = OMe, R$^2$ = H |
| 661 | J = J-2c, Q = CH$_2$, R$^1$ = OEt, R$^2$ = H |
| 662 | J = J-2c, Q = CH$_2$, R$^1$ = OCHF$_2$, R$^2$ = H |
| 663 | J = J-2c, Q = CH$_2$, R$^1$ = OCH$_2$CF$_3$, R$^2$ = H |
| 664 | J = J-2c, Q = CH$_2$, R$^1$ = NHMe, R$^2$ = H |
| 665 | J = J-2c, Q = CH$_2$, R$^1$ = NHEt, R$^2$ = H |
| 666 | J = J-2c, Q = CH$_2$, R$^1$ = NMe$_2$, R$^2$ = H |
| 667 | J = J-2c, Q = CH$_2$, R$^1$ = NEt$_2$, R$^2$ = H |
| 668 | J = J-2c, Q = CH$_2$, R$^1$ = NMeEt, R$^2$ = H |
| 669 | J = J-2c, Q = CH$_2$, R$^1$ = Cl, R$^2$ = H |
| 670 | J = J-2c, Q = CH$_2$, R$^1$ = Br, R$^2$ = H |
| 671 | J = J-2c, Q = CH$_2$, R$^1$ = H, R$^2$ = Me |
| 672 | J = J-2c, Q = CH$_2$, R$^1$ = H, R$^2$ = Et |
| 673 | J = J-2c, Q = CH$_2$, R$^1$ = H, R$^2$ = n-Pr |
| 674 | J = J-2c, Q = CH$_2$, R$^1$ = H, R$^2$ = i-Pr |
| 675 | J = J-2c, Q = CH$_2$, R$^1$ = H, R$^2$ = CH$_2$OMe |
| 676 | J = J-2c, Q = CH$_2$, R$^1$ = H, R$^2$ = CH$_2$F |
| 677 | J = J-2c, Q = CH$_2$, R$^1$ = H, R$^2$ = CHF$_2$ |
| 678 | J = J-2c, Q = CH$_2$, R$^1$ = H, R$^2$ = CF$_3$ |
| 679 | J = J-2c, Q = CH$_2$, R$^1$ = H, R$^2$ = OMe |
| 680 | J = J-2c, Q = CH$_2$, R$^1$ = H, R$^2$ = OEt |
| 681 | J = J-2c, Q = CH$_2$, R$^1$ = H, R$^2$ = OCHF$_2$ |
| 682 | J = J-2c, Q = CH$_2$, R$^1$ = H, R$^2$ = OCH$_2$CF$_3$ |
| 683 | J = J-2c, Q = CH$_2$, R$^1$ = H, R$^2$ = NHMe |
| 684 | J = J-2c, Q = CH$_2$, R$^1$ = H, R$^2$ = NHEt |
| 685 | J = J-2c, Q = CH$_2$, R$^1$ = H, R$^2$ = NMe$_2$ |
| 686 | J = J-2c, Q = CH$_2$, R$^1$ = H, R$^2$ = NEt$_2$ |
| 687 | J = J-2c, Q = CH$_2$, R$^1$ = H, R$^2$ = NMeEt |
| 688 | J = J-2c, Q = CH$_2$, R$^1$ = H, R$^2$ = Cl |
| 689 | J = J-2c, Q = CH$_2$, R$^1$ = Me, R$^2$ = Me |
| 690 | J = J-2c, Q = CH$_2$, R$^1$ = Et, R$^2$ = Et |
| 691 | J = J-2c, Q = CH$_2$, R$^1$ = Me, R$^2$ = Cl |
| 692 | J = J-2c, Q = CH$_2$, R$^1$ = Cl, R$^2$ = Me |
| 693 | J = J-2c, Q = CH$_2$, R$^1$ = Cl, R$^2$ = Cl |
| 694 | J = J-2c, Q = CH$_2$, R$^1$, R$^2$ = —(CH$_2$)$_3$— |
| 695 | J = J-2c, Q = CH$_2$, R$^1$, R$^2$ = —(CH$_2$)$_4$— |
| 696 | J = J-2c, Q = C(=O), R$^1$ = Me, R$^2$ = H |
| 697 | J = J-2c, Q = C(=O), R$^1$ = Et, R$^2$ = H |
| 698 | J = J-2c, Q = C(=O), R$^1$ = n-Pr, R$^2$ = H |
| 699 | J = J-2c, Q = C(=O), R$^1$ = i-Pr, R$^2$ = H |
| 700 | J = J-2c, Q = C(=O), R$^1$ = CH$_2$OMe, R$^2$ = H |
| 701 | J = J-2c, Q = C(=O), R$^1$ = CH$_2$F, R$^2$ = H |
| 702 | J = J-2c, Q = C(=O), R$^1$ = CHF$_2$, R$^2$ = H |
| 703 | J = J-2c, Q = C(=O), R$^1$ = CF$_3$, R$^2$ = H |
| 704 | J = J-2c, Q = C(=O), R$^1$ = OMe, R$^2$ = H |
| 705 | J = J-2c, Q = C(=O), R$^1$ = OEt, R$^2$ = H |
| 706 | J = J-2c, Q = C(=O), R$^1$ = OCHF$_2$, R$^2$ = H |
| 707 | J = J-2c, Q = C(=O), R$^1$ = OCH$_2$CF$_3$, R$^2$ = H |

TABLE 1450-continued

| Table | Row Heading |
|---|---|
| 708 | J = J-2c, Q = C(=O), R¹ = NHMe, R² = H |
| 709 | J = J-2c, Q = C(=O), R¹ = NHEt, R² = H |
| 710 | J = J-2c, Q = C(=O), R¹ = NMe₂, R² = H |
| 711 | J = J-2c, Q = C(=O), R¹ = NEt₂, R² = H |
| 712 | J = J-2c, Q = C(=O), R¹ = NMeEt, R² = H |
| 713 | J = J-2c, Q = C(=O), R¹ = Cl, R² = H |
| 714 | J = J-2c, Q = C(=O), R¹ = Br, R² = H |
| 715 | J = J-2c, Q = C(=O), R¹ = H, R² = Me |
| 716 | J = J-2c, Q = C(=O), R¹ = H, R² = Et |
| 717 | J = J-2c, Q = C(=O), R¹ = H, R² = n-Pr |
| 718 | J = J-2c, Q = C(=O), R¹ = H, R² = i-Pr |
| 719 | J = J-2c, Q = C(=O), R¹ = H, R² = CH₂OMe |
| 720 | J = J-2c, Q = C(=O), R¹ = H, R² = CH₂F |
| 721 | J = J-2c, Q = C(=O), R¹ = H, R² = CHF₂ |
| 722 | J = J-2c, Q = C(=O), R¹ = H, R² = CF₃ |
| 723 | J = J-2c, Q = C(=O), R¹ = H, R² = OMe |
| 724 | J = J-2c, Q = C(=O), R¹ = H, R² = OEt |
| 725 | J = J-2c, Q = C(=O), R¹ = H, R² = OCHF₂ |
| 726 | J = J-2c, Q = C(=O), R¹ = H, R² = OCH₂CF₃ |
| 727 | J = J-2c, Q = C(=O), R¹ = H, R² = NHMe |
| 728 | J = J-2c, Q = C(=O), R¹ = H, R² = NHEt |
| 729 | J = J-2c, Q = C(=O), R¹ = H, R² = NMe₂ |
| 730 | J = J-2c, Q = C(=O), R¹ = H, R² = NEt₂ |
| 731 | J = J-2c, Q = C(=O), R¹ = H, R² = NMeEt |
| 732 | J = j-2c, Q = C(=O), R¹ = H, R² = Cl |
| 733 | J = J-2c, Q = C(=O), R¹ = Me, R² = Me |
| 734 | J = J-2c, Q = C(=O), R¹ = Et, R² = Et |
| 735 | J = J-2c, Q = C(=O), R¹ = Me, R² = Cl |
| 736 | J = J-2c, Q = C(=O), R¹ = Cl, R² = Me |
| 737 | J = J-2c, Q = C(=O), R¹ = Cl, R² = Cl |
| 738 | J = J-2c, Q = C(=O), R¹, R² = —(CH₂)₃— |
| 739 | J = J-2c, Q = C(=O), R¹, R² = —(CH₂)₄— |
| 740 | J = J-2c, Q = C(OH)H, R¹ = Me, R² = H |
| 741 | J = J-2c, Q = C(OH)H, R¹ = Et, R² = H |
| 742 | J = J-2c, Q = C(OH)H, R¹ = n-Pr, R² = H |
| 743 | J = J-2c, Q = C(OH)H, R¹ = i-Pr, R² = H |
| 744 | J = J-2c, Q = C(OH)H, R¹ = CH₂OMe, R² = H |
| 745 | J = J-2c, Q = C(OH)H, R¹ = CH₂F, R² = H |
| 746 | J = J-2c, Q = C(OH)H, R¹ = CHF₂, R² = H |
| 747 | J = J-2c, Q = C(OH)H, R¹ = CF₃, R² = H |
| 748 | J = J-2c, Q = C(OH)H, R¹ = OMe, R² = H |
| 749 | J = J-2c, Q = C(OH)H, R¹ = OEt, R² = H |
| 750 | J = J-2c, Q = C(OH)H, R¹ = OCHF₂, R² = H |
| 751 | J = J-2c, Q = C(OH)H, R¹ = OCH₂CF₃, R² = H |
| 752 | J = J-2c, Q = C(OH)H, R¹ = NHMe, R² = H |
| 753 | J = J-2c, Q = C(OH)H, R¹ = NHEt, R² = H |
| 754 | J = J-2c, Q = C(OH)H, R¹ = NMe₂, R² = H |
| 755 | J = J-2c, Q = C(OH)H, R¹ = NEt₂, R² = H |
| 756 | J = J-2c, Q = C(OH)H, R¹ = NMeEt, R² = H |
| 757 | J = J-2c, Q = C(OH)H, R¹ = Cl, R² = H |
| 758 | J = J-2c, Q = C(OH)H, R¹ = Br, R² = H |
| 759 | J = J-2c, Q = C(OH)H, R¹ = H, R² = Me |
| 760 | J = J-2c, Q = C(OH)H, R¹ = H, R² = Et |
| 761 | J = J-2c, Q = C(OH)H, R¹ = H, R² = n-Pr |
| 762 | J = J-2c, Q = C(OH)H, R¹ = H, R² = i-Pr |
| 763 | J = J-2c, Q = C(OH)H, R¹ = H, R² = CH₂OMe |
| 764 | J = J-2c, Q = C(OH)H, R¹ = H, R² = CH₂F |
| 765 | J = J-2c, Q = C(OH)H, R¹ = H, R² = CHF₂ |
| 766 | J = J-2c, Q = C(OH)H, R¹ = H, R² = CF₃ |
| 767 | J = J-2c, Q = C(OH)H, R¹ = H, R² = OMe |
| 768 | J = J-2c, Q = C(OH)H, R¹ = H, R² = OEt |
| 769 | J = J-2c, Q = C(OH)H, R¹ = H, R² = OCHF₂ |
| 770 | J = J-2c, Q = C(OH)H, R¹ = H, R² = OCH₂CF₃ |
| 771 | J = J-2c, Q = C(OH)H, R¹ = H, R² = NHMe |
| 772 | J = J-2c, Q = C(OH)H, R¹ = H, R² = NHEt |
| 773 | J = J-2c, Q = C(OH)H, R¹ = H, R² = NMe₂ |
| 774 | J = J-2c, Q = C(OH)H, R¹ = H, R² = NEt₂ |
| 775 | J = J-2c, Q = C(OH)H, R¹ = H, R² = NMeEt |
| 776 | J = J-2c, Q = C(OH)H, R¹ = H, R² = Cl |
| 777 | J = J-2c, Q = C(OH)H, R¹ = Me, R² = Me |
| 778 | J = J-2c, Q = C(OH)H, R¹ = Et, R² = Et |
| 779 | J = J-2c, Q = C(OH)H, R¹ = Me, R² = Cl |
| 780 | J = J-2c, Q = C(OH)H, R¹ = Cl, R² = Me |
| 781 | J = J-2c, Q = CHF, R¹ = Me, R² = H |
| 782 | J = J-2c, Q = CHF, R¹ = Et, R² = H |
| 783 | J = J-2c, Q = CHF, R¹ = n-Pr, R² = H |
| 784 | J = J-2c, Q = CHF, R¹ = i-Pr, R² = H |
| 785 | J = J-2c, Q = CHF, R¹ = CH₂OMe, R² = H |
| 786 | J = J-2c, Q = CHF, R¹ = CH₂F, R² = H |
| 787 | J = J-2c, Q = CHF, R¹ = CHF₂, R² = H |
| 788 | J = J-2c, Q = CHF, R¹ = CF₃, R² = H |
| 789 | J = J-2c, Q = CHF, R¹ = OMe, R² = H |
| 790 | J = J-2c, Q = CHF, R¹ = OEt, R² = H |
| 791 | J = J-2c, Q = CHF, R¹ = OCHF₂, R² = H |
| 792 | J = J-2c, Q = CHF, R¹ = OCH₂CF₃, R² = H |
| 793 | J = J-2c, Q = CHF, R¹ = NHMe, R² = H |
| 794 | J = J-2c, Q = CHF, R¹ = NHEt, R² = H |
| 795 | J = J-2c, Q = CHF, R¹ = NMe₂, R² = H |
| 796 | J = J-2c, Q = CHF, R¹ = NEt₂, R² = H |
| 797 | J = J-2c, Q = CHF, R¹ = NMeEt, R² = H |
| 798 | J = J-2c, Q = CHF, R¹ = Cl, R² = H |
| 799 | J = J-2c, Q = CHF, R¹ = Br, R² = H |
| 800 | J = J-2c, Q = CHF, R¹ = H, R² = Me |
| 801 | J = J-2c, Q = CHF, R¹ = H, R² = Et |
| 802 | J = J-2c, Q = CHF, R¹ = H, R² = n-Pr |
| 803 | J = J-2c, Q = CHF, R¹ = H, R² = i-Pr |
| 804 | J = J-2c, Q = CHF, R¹ = H, R² = CH₂OMe |
| 805 | J = J-2c, Q = CHF, R¹ = H, R² = CH₂F |
| 806 | J = J-2c, Q = CHF, R¹ = H, R² = CHF₂ |
| 807 | J = J-2c, Q = CHF, R¹ = H, R² = CF₃ |
| 808 | J = J-2c, Q = CHF, R¹ = H, R² = OMe |
| 809 | J = J-2c, Q = CHF, R¹ = H, R² = OEt |
| 810 | J = J-2c, Q = CHF, R¹ = H, R² = OCHF₂ |
| 811 | J = J-2c, Q = CHF, R¹ = H, R² = OCH₂CF₃ |
| 812 | J = J-2c, Q = CHF, R¹ = H, R² = NHMe |
| 813 | J = J-2c, Q = CHF, R¹ = H, R² = NHEt |
| 814 | J = J-2c, Q = CHF, R¹ = H, R² = NMe₂ |
| 815 | J = J-2c, Q = CHF, R¹ = H, R² = NEt₂ |
| 816 | J = J-2c, Q = CHF, R¹ = H, R² = NMeEt |
| 817 | J = J-2c, Q = CHF, R¹ = H, R² = Cl |
| 818 | J = J-2c, Q = CHF, R¹ = Me, R² = Me |
| 819 | J = J-2c, Q = CHF, R¹ = Et, R² = Et |
| 820 | J = J-2c, Q = CHF, R¹ = Me, R² = Cl |
| 821 | J = J-2c, Q = CHF, R¹ = Cl, R² = Me |
| 822 | J = J-2c, Q = CHF, R¹ = Cl, R² = Cl |
| 823 | J = J-2c, Q = CHF, R¹, R² = —(CH₂)₃— |
| 824 | J = J-2c, Q = CHF, R¹, R² = —(CH₂)₄— |
| 825 | J = J-2c, Q = S, R¹ = Me, R² = H |
| 826 | J = J-2c, Q = S, R¹ = Et, R² = H |
| 827 | J = J-2c, Q = S, R¹ = n-Pr, R² = H |
| 828 | J = J-2c, Q = S, R¹ = i-Pr, R² = H |
| 829 | J = J-2c, Q = S, R¹ = CH₂OMe, R² = H |
| 830 | J = J-2c, Q = S, R¹ = CH₂F, R² = H |
| 831 | J = J-2c, Q = S, R¹ = CHF₂, R² = H |
| 832 | J = J-2c, Q = S, R¹ = CF₃, R² = H |
| 833 | J = J-2c, Q = S, R¹ = OMe, R² = H |
| 834 | J = J-2c, Q = S, R¹ = OEt, R² = H |
| 835 | J = J-2c, Q = S, R¹ = OCHF₂, R² = H |
| 836 | J = J-2c, Q = S, R¹ = OCH₂CF₃, R² = H |
| 837 | J = J-2c, Q = S, R¹ = NHMe, R² = H |
| 838 | J = J-2c, Q = S, R¹ = NHEt, R² = H |
| 839 | J = J-2c, Q = S, R¹ = NMe₂, R² = H |
| 840 | J = J-2c, Q = S, R¹ = NEt₂, R² = H |
| 841 | J = J-2c, Q = S, R¹ = NMeEt, R² = H |
| 842 | J = J-2c, Q = S, R¹ = Cl, R² = H |
| 843 | J = J-2c, Q = S, R¹ = Br, R² = H |
| 844 | J = J-2c, Q = S, R¹ = H, R² = Me |
| 845 | J = J-2c, Q = S, R¹ = H, R² = Et |
| 846 | J = J-2c, Q = S, R¹ = H, R² = n-Pr |
| 847 | J = J-2c, Q = S, R¹ = H, R² = i-Pr |
| 848 | J = J-2c, Q = S, R¹ = H, R² = CH₂OMe |
| 849 | J = J-2c, Q = S, R¹ = H, R² = CH₂F |
| 850 | J = J-2c, Q = S, R¹ = H, R² = CHF₂ |
| 851 | J = J-2c, Q = S, R¹ = H, R² = CF₃ |
| 852 | J = J-2c, Q = S, R¹ = H, R² = OMe |
| 853 | J = J-2c, Q = S, R¹ = H, R² = OEt |
| 854 | J = J-2c, Q = S, R¹ = H, R² = OCHF₂ |
| 855 | J = J-2c, Q = S, R¹ = H, R² = OCH₂CF₃ |
| 856 | J = J-2c, Q = S, R¹ = H, R² = NHMe |
| 857 | J = J-2c, Q = S, R¹ = H, R² = NHEt |
| 858 | J = J-2c, Q = S, R¹ = H, R² = NMe₂ |
| 859 | J = J-2c, Q = S, R¹ = H, R² = NEt₂ |
| 860 | J = J-2c, Q = S, R¹ = H, R² = NMeEt |
| 861 | J = J-2c, Q = S, R¹ = H, R² = Cl |
| 862 | J = J-2c, Q = S, R¹ = Me, R² = Me |
| 863 | J = J-2c, Q = S, R¹ = Et, R² = Et |

TABLE 1450-continued

| Table | Row Heading |
|---|---|
| 864 | J = J-2c, Q = S, $R^1$ = Me, $R^2$ = Cl |
| 865 | J = J-2c, Q = S, $R^1$ = Cl, $R^2$ = Me |
| 866 | J = J-2c, Q = NH, $R^1$ = Me, $R^2$ = H |
| 867 | J = J-2c, Q = NH, $R^1$ = Et, $R^2$ = H |
| 868 | J = J-2c, Q = NH, $R^1$ = n-Pr, $R^2$ = H |
| 869 | J = J-2c, Q = NH, $R^1$ = i-Pr, $R^2$ = H |
| 870 | J = J-2c, Q = NH, $R^1$ = $CH_2OMe$, $R^2$ = H |
| 871 | J = J-2c, Q = NH, $R^1$ = $CH_2F$, $R^2$ = H |
| 872 | J = J-2c, Q = NH, $R^1$ = $NH_2$, $R^2$ = H |
| 873 | J = J-2c, Q = NH, $R^1$ = $CF_3$, $R^2$ = H |
| 874 | J = J-2c, Q = NH, $R^1$ = OMe, $R^2$ = H |
| 875 | J = J-2c, Q = NH, $R^1$ = OEt, $R^2$ = H |
| 876 | J = J-2c, Q = NH, $R^1$ = $OCHF_2$, $R^2$ = H |
| 877 | J = J-2c, Q = NH, $R^1$ = $OCH_2CF_3$, $R^2$ = H |
| 878 | J = J-2c, Q = NH, $R^1$ = NHMe, $R^2$ = H |
| 879 | J = J-2c, Q = NH, $R^1$ = NHEt, $R^2$ = H |
| 880 | J = J-2c, Q = NH, $R^1$ = $NMe_2$, $R^2$ = H |
| 881 | J = J-2c, Q = NH, $R^1$ = $NEt_2$, $R^2$ = H |
| 882 | J = J-2c, Q = NH, $R^1$ = NMeEt, $R^2$ = H |
| 883 | J = J-2c, Q = NH, $R^1$ = Cl, $R^2$ = H |
| 884 | J = J-2c, Q = NH, $R^1$ = Br, $R^2$ = H |
| 885 | J = J-2c, Q = NH, $R^1$ = H, $R^2$ = Me |
| 886 | J = J-2c, Q = NH, $R^1$ = H, $R^2$ = Et |
| 887 | J = J-2c, Q = NH, $R^1$ = H, $R^2$ = n-Pr |
| 888 | J = J-2c, Q = NH, $R^1$ = H, $R^2$ = i-Pr |
| 889 | J = J-2c, Q = NH, $R^1$ = H, $R^2$ = $CH_2OMe$ |
| 890 | J = J-2c, Q = NH, $R^1$ = H, $R^2$ = $CH_2F$ |
| 891 | J = J-2c, Q = NH, $R^1$ = H, $R^2$ = $CHF_2$ |
| 892 | J = J-2c, Q = NH, $R^1$ = H, $R^2$ = $CF_3$ |
| 893 | J = J-2c, Q = NH, $R^1$ = H, $R^2$ = OMe |
| 894 | J = J-2c, Q = NH, $R^1$ = H, $R^2$ = OEt |
| 895 | J = J-2c, Q = NH, $R^1$ = H, $R^2$ = $OCHF_2$ |
| 896 | J = J-2c, Q = NH, $R^1$ = H, $R^2$ = $OCH_2CF_3$ |
| 897 | J = J-2c, Q = NH, $R^1$ = H, $R^2$ = NHMe |
| 898 | J = J-2c, Q = NH, $R^1$ = H, $R^2$ = NHEt |
| 899 | J = J-2c, Q = NH, $R^1$ = H, $R^2$ = $NMe_2$ |
| 900 | J = J-2c, Q = NH, $R^1$ = H, $R^2$ = $NEt_2$ |
| 901 | J = J-2c, Q = NH, $R^1$ = H, $R^2$ = NMeEt |
| 902 | J = J-2c, Q = NH, $R^1$ = H, $R^2$ = Cl |
| 903 | J = J-2c, Q = NH, $R^1$ = Me, $R^2$ = Me |
| 904 | J = J-2c, Q = NH, $R^1$ = Et, $R^2$ = Et |
| 905 | J = J-2c, Q = NH, $R^1$ = Me, $R^2$ = Cl |
| 906 | J = J-2c, Q = NH, $R^1$ = Cl, $R^2$ = Me |
| 907 | J = J-2c, Q = NH, $R^1$ = Cl, $R^2$ = Cl |
| 908 | J = J-2c, Q = NH, $R^1$, $R^2$ = —$(CH_2)_3$— |
| 909 | J = J-2c, Q = NH, $R^1$, $R^2$ = —$(CH_2)_4$— |
| 910 | J = J-1a, Q = O, $R^1$ = Me, $R^2$ = H |
| 911 | J = J-1a, Q = O, $R^1$ = Et, $R^2$ = H |
| 912 | J = J-1a, Q = O, $R^1$ = n-Pr, $R^2$ = H |
| 913 | J = J-1a, Q = O, $R^1$ = $CH_2OMe$, $R^2$ = H |
| 914 | J = J-1a, Q = O, $R^1$ = $CH_2F$, $R^2$ = H |
| 915 | J = J-1a, Q = O, $R^1$ = OMe, $R^2$ = H |
| 916 | J = J-1a, Q = O, $R^1$ = OEt, $R^2$ = H |
| 917 | J = J-1a, Q = O, $R^1$ = NHMe, $R^2$ = H |
| 918 | J = J-1a, Q = O, $R^1$ = NHEt, $R^2$ = H |
| 919 | J = J-1a, Q = O, $R^1$ = $NMe_2$, $R^2$ = H |
| 920 | J = J-1a, Q = O, $R^1$ = $NEt_2$, $R^2$ = H |
| 921 | J = J-1a, Q = O, $R^1$ = NMeEt, $R^2$ = H |
| 922 | J = J-1a, Q = O, $R^1$ = Cl, $R^2$ = H |
| 923 | J = J-1a, Q = O, $R^1$ = Br, $R^2$ = H |
| 924 | J = J-1a, Q = O, $R^1$ = H, $R^2$ = Me |
| 925 | J = J-1a, Q = O, $R^1$ = H, $R^2$ = Et |
| 926 | J = J-1a, Q = O, $R^1$ = H, $R^2$ = n-Pr |
| 927 | J = J-1a, Q = O, $R^1$ = H, $R^2$ = $CH_2OMe$ |
| 928 | J = J-1a, Q = O, $R^1$ = H, $R^2$ = OMe |
| 929 | J = J-1a, Q = O, $R^1$ = H, $R^2$ = OEt |
| 930 | J = J-1a, Q = O, $R^1$ = H, $R^2$ = NHMe |
| 931 | J = J-1a, Q = O, $R^1$ = H, $R^2$ = NHEt |
| 932 | J = J-1a, Q = O, $R^1$ = H, $R^2$ = $NMe_2$ |
| 933 | J = J-1a, Q = O, $R^1$ = H, $R^2$ = $NEt_2$ |
| 934 | J = J-1a, Q = O, $R^1$ = H, $R^2$ = NMeEt |
| 935 | J = J-1a, Q = O, $R^1$ = H, $R^2$ = Cl |
| 936 | J = J-1a, Q = O, $R^1$ = H, $R^2$ = Br |
| 937 | J = J-1a, Q = O, $R^1$ = Me, $R^2$ = Me |
| 938 | J = J-1a, Q = O, $R^1$, $R^2$ = —$(CH_2)_3$— |
| 939 | J = J-1a, Q = O, $R^1$, $R^2$ = —$(CH_2)_4$— |
| 940 | J = J-1a, Q = $CH_2$, $R^1$ = Me, $R^2$ = H |
| 941 | J = J-1a, Q = $CH_2$, $R^1$ = Et, $R^2$ = H |
| 942 | J = J-1a, Q = $CH_2$, $R^1$ = n-Pr, $R^2$ = H |
| 943 | J = J-1a, Q = $CH_2$, $R^1$ = $CH_2OMe$, $R^2$ = H |
| 944 | J = J-1a, Q = $CH_2$, $R^1$ = $CH_2F$, $R^2$ = H |
| 945 | J = J-1a, Q = $CH_2$, $R^1$ = OMe, $R^2$ = H |
| 946 | J = J-1a, Q = $CH_2$, $R^1$ = OEt, $R^2$ = H |
| 947 | J = J-1a, Q = $CH_2$, $R^1$ = NHMe, $R^2$ = H |
| 948 | J = J-1a, Q = $CH_2$, $R^1$ = NHEt, $R^2$ = H |
| 949 | J = J-1a, Q = $CH_2$, $R^1$ = $NMe_2$, $R^2$ = H |
| 950 | J = J-1a, Q = $CH_2$, $R^1$ = $NEt_2$, $R^2$ = H |
| 951 | J = J-1a, Q = $CH_2$, $R^1$ = NMeEt, $R^2$ = H |
| 952 | J = J-1a, Q = $CH_2$, $R^1$ = Cl, $R^2$ = H |
| 953 | J = J-1a, Q = $CH_2$, $R^1$ = Br, $R^2$ = H |
| 954 | J = J-1a, Q = $CH_2$, $R^1$ = H, $R^2$ = Me |
| 955 | J = J-1a, Q = $CH_2$, $R^1$ = H, $R^2$ = Et |
| 956 | J = J-1a, Q = $CH_2$, $R^1$ = H, $R^2$ = n-Pr |
| 957 | J = J-1a, Q = $CH_2$, $R^1$ = H, $R^2$ = $CH_2OMe$ |
| 958 | J = J-1a, Q = $CH_2$, $R^1$ = H, $R^2$ = OMe |
| 959 | J = J-1a, Q = $CH_2$, $R^1$ = H, $R^2$ = OEt |
| 960 | J = J-1a, Q = $CH_2$, $R^1$ = H, $R^2$ = NHMe |
| 961 | J = J-1a, Q = $CH_2$, $R^1$ = H, $R^2$ = NHEt |
| 962 | J = J-1a, Q = $CH_2$, $R^1$ = H, $R^2$ = $NMe_2$ |
| 963 | J = J-1a, Q = $CH_2$, $R^1$ = H, $R^2$ = $NEt_2$ |
| 964 | J = J-1a, Q = $CH_2$, $R^1$ = H, $R^2$ = NMeEt |
| 965 | J = J-1a, Q = $CH_2$, $R^1$ = H, $R^2$ = Cl |
| 966 | J = J-1a, Q = $CH_2$, $R^1$ = H, $R^2$ = Br |
| 967 | J = J-1a, Q = $CH_2$, $R^1$ = Me, $R^2$ = Me |
| 968 | J = J-1a, Q = $CH_2$, $R^1$, $R^2$ = —$(CH_2)_3$— |
| 969 | J = J-1a, Q = $CH_2$, $R^1$, $R^2$ = —$(CH_2)_4$— |
| 970 | J = J-1a, Q = C(=O), $R^1$ = Me, $R^2$ = H |
| 971 | J = J-1a, Q = C(=O), $R^1$ = Et, $R^2$ = H |
| 972 | J = J-1a, Q = C(=O), $R^1$ = n-Pr, $R^2$ = H |
| 973 | J = J-1a, Q = C(=O), $R^1$ = $CH_2OMe$, $R^2$ = H |
| 974 | J = J-1a, Q = C(=O), $R^1$ = $CH_2F$, $R^2$ = H |
| 975 | J = J-1a, Q = C(=O), $R^1$ = OMe, $R^2$ = H |
| 976 | J = J-1a, Q = C(=O), $R^1$ = OEt, $R^2$ = H |
| 977 | J = J-1a, Q = C(=O), $R^1$ = NHMe, $R^2$ = H |
| 978 | J = J-1a, Q = C(=O), $R^1$ = NHEt, $R^2$ = H |
| 979 | J = J-1a, Q = C(=O), $R^1$ = $NMe_2$, $R^2$ = H |
| 980 | J = J-1a, Q = C(=O), $R^1$ = $NEt_2$, $R^2$ = H |
| 981 | J = J-1a, Q = C(=O), $R^1$ = NMeEt, $R^2$ = H |
| 982 | J = J-1a, Q = C(=O), $R^1$ = Cl, $R^2$ = H |
| 983 | J = J-1a, Q = C(=O), $R^1$ = Br, $R^2$ = H |
| 984 | J = J-1a, Q = C(=O), $R^1$ = H, $R^2$ = Me |
| 985 | J = J-1a, Q = C(=O), $R^1$ = H, $R^2$ = Et |
| 986 | J = J-1a, Q = C(=O), $R^1$ = H, $R^2$ = n-Pr |
| 987 | J = J-1a, Q = C(=O), $R^1$ = H, $R^2$ = $CH_2OMe$ |
| 988 | J = J-1a, Q = C(=O), $R^1$ = H, $R^2$ = OMe |
| 989 | J = J-1a, Q = C(=O), $R^1$ = H, $R^2$ = OEt |
| 990 | J = J-1a, Q = C(=O), $R^1$ = H, $R^2$ = NHMe |
| 991 | J = J-1a, Q = C(=O), $R^1$ = H, $R^2$ = NHEt |
| 992 | J = J-1a, Q = C(=O), $R^1$ = H, $R^2$ = $NMe_2$ |
| 993 | J = J-1a, Q = C(=O), $R^1$ = H, $R^2$ = $NEt_2$ |
| 994 | J = J-1a, Q = C(=O), $R^1$ = H, $R^2$ = NMeEt |
| 995 | J = J-1a, Q = C(=O), $R^1$ = H, $R^2$ = Cl |
| 996 | J = J-1a, Q = C(=O), $R^1$ = H, $R^2$ = Br |
| 997 | J = J-1a, Q = C(=O), $R^1$ = Me, $R^2$ = Me |
| 998 | J = J-1a, Q = C(=O), $R^1$, $R^2$ = —$(CH_2)_3$— |
| 999 | J = J-1a, Q = C(=O), $R^1$, $R^2$ = —$(CH_2)_4$— |
| 1000 | J = J-1b, Q = O, $R^1$ = Me, $R^2$ = H |
| 1001 | J = J-1b, Q = O, $R^1$ = Et, $R^2$ = H |
| 1002 | J = J-1b, Q = O, $R^1$ = n-Pr, $R^2$ = H |
| 1003 | J = J-1b, Q = O, $R^1$ = $CH_2OMe$, $R^2$ = H |
| 1004 | J = J-1b, Q = O, $R^1$ = $CH_2F$, $R^2$ = H |
| 1005 | J = J-1b, Q = O, $R^1$ = OMe, $R^2$ = H |
| 1006 | J = J-1b, Q = O, $R^1$ = OEt, $R^2$ = H |
| 1007 | J = J-1b, Q = O, $R^1$ = NHMe, $R^2$ = H |
| 1008 | J = J-1b, Q = O, $R^1$ = NHEt, $R^2$ = H |
| 1009 | J = J-1b, Q = O, $R^1$ = $NMe_2$, $R^2$ = H |
| 1010 | J = J-1b, Q = O, $R^1$ = $NEt_2$, $R^2$ = H |
| 1011 | J = J-1b, Q = O, $R^1$ = NMeEt, $R^2$ = H |
| 1012 | J = J-1b, Q = O, $R^1$ = Cl, $R^2$ = H |
| 1013 | J = J-1b, Q = O, $R^1$ = Br, $R^2$ = H |
| 1014 | J = J-1b, Q = O, $R^1$ = H, $R^2$ = Me |
| 1015 | J = J-1b, Q = O, $R^1$ = H, $R^2$ = Et |
| 1016 | J = J-1b, Q = O, $R^1$ = H, $R^2$ = n-Pr |
| 1017 | J = J-1b, Q = O, $R^1$ = H, $R^2$ = $CH_2OMe$ |
| 1018 | J = J-1b, Q = O, $R^1$ = H, $R^2$ = OMe |
| 1019 | J = J-1b, Q = O, $R^1$ = H, $R^2$ = OEt |

TABLE 1450-continued

| Table | Row Heading |
|---|---|
| 1020 | J = J-1b, Q = O, R$^1$ = H, R$^2$ = NHMe |
| 1021 | J = J-1b, Q = O, R$^1$ = H, R$^2$ = NHEt |
| 1022 | J = J-1b, Q = O, R$^1$ = H, R$^2$ = NMe$_2$ |
| 1023 | J = J-1b, Q = O, R$^1$ = H, R$^2$ = NEt$_2$ |
| 1024 | J = J-1b, Q = O, R$^1$ = H, R$^2$ = NMeEt |
| 1025 | J = J-1b, Q = O, R$^1$ = H, R$^2$ = Cl |
| 1026 | J = J-1b, Q = O, R$^1$ = H, R$^2$ = Br |
| 1027 | J = J-1b, Q = O, R$^1$ = Me, R$^2$ = Me |
| 1028 | J = J-1b, Q = O, R$^1$, R$^2$ = —(CH$_2$)$_3$— |
| 1029 | J = J-1b, Q = O, R$^1$, R$^2$ = —(CH$_2$)$_4$— |
| 1030 | J = J-1b, Q = CH$_2$, R$^1$ = Me, R$^2$ = H |
| 1031 | J = J-1b, Q = CH$_2$, R$^1$ = Et, R$^2$ = H |
| 1032 | J = J-1b, Q = CH$_2$, R$^1$ = n-Pr, R$^2$ = H |
| 1033 | J = J-1b, Q = CH$_2$, R$^1$ = CH$_2$OMe, R$^2$ = H |
| 1034 | J = J-1b, Q = CH$_2$, R$^1$ = CH$_2$F, R$^2$ = H |
| 1035 | J = J-1b, Q = CH$_2$, R$^1$ = OMe, R$^2$ = H |
| 1036 | J = J-1b, Q = CH$_2$, R$^1$ = OEt, R$^2$ = H |
| 1037 | J = J-1b, Q = CH$_2$, R$^1$ = NHMe, R$^2$ = H |
| 1038 | J = J-1b, Q = CH$_2$, R$^1$ = NHEt, R$^2$ = H |
| 1039 | J = J-1b, Q = CH$_2$, R$^1$ = NMe$_2$, R$^2$ = H |
| 1040 | J = J-1b, Q = CH$_2$, R$^1$ = NEt$_2$, R$^2$ = H |
| 1041 | J = J-1b, Q = CH$_2$, R$^1$ = NMeEt, R$^2$ = H |
| 1042 | J = J-1b, Q = CH$_2$, R$^1$ = Cl, R$^2$ = H |
| 1043 | J = J-1b, Q = CH$_2$, R$^1$ = Br, R$^2$ = H |
| 1044 | J = J-1b, Q = CH$_2$, R$^1$ = H, R$^2$ = Me |
| 1045 | J = J-1b, Q = CH$_2$, R$^1$ = H, R$^2$ = Et |
| 1046 | J = J-1b, Q = CH$_2$, R$^1$ = H, R$^2$ = n-Pr |
| 1047 | J = J-1b, Q = CH$_2$, R$^1$ = H, R$^2$ = CH$_2$OMe |
| 1048 | J = J-1b, Q = CH$_2$, R$^1$ = H, R$^2$ = OMe |
| 1049 | J = J-1b, Q = CH$_2$, R$^1$ = H, R$^2$ = OEt |
| 1050 | J = J-1b, Q = CH$_2$, R$^1$ = H, R$^2$ = NHMe |
| 1051 | J = J-1b, Q = CH$_2$, R$^1$ = H, R$^2$ = NHEt |
| 1052 | J = J-1b, Q = CH$_2$, R$^1$ = H, R$^2$ = NMe$_2$ |
| 1053 | J = J-1b, Q = CH$_2$, R$^1$ = H, R$^2$ = NEt$_2$ |
| 1054 | J = J-1b, Q = CH$_2$, R$^1$ = H, R$^2$ = NMeEt |
| 1055 | J = J-1b, Q = CH$_2$, R$^1$ = H, R$^2$ = Cl |
| 1056 | J = J-1b, Q = CH$_2$, R$^1$ = H, R$^2$ = Br |
| 1057 | J = J-1b, Q = CH$_2$, R$^1$ = Me, R$^2$ = Me |
| 1058 | J = J-1b, Q = CH$_2$, R$^1$, R$^2$ = —(CH$_2$)$_3$— |
| 1059 | J = J-1b, Q = CH$_2$, R$^1$, R$^2$ = —(CH$_2$)$_4$— |
| 1060 | J = J-1b, Q = C(=O), R$^1$ = Me, R$^2$ = H |
| 1061 | J = J-1b, Q = C(=O), R$^1$ = Et, R$^2$ = H |
| 1062 | J = J-1b, Q = C(=O), R$^1$ = n-Pr, R$^2$ = H |
| 1063 | J = J-1b, Q = C(=O), R$^1$ = CH$_2$OMe, R$^2$ = H |
| 1064 | J = J-1b, Q = C(=O), R$^1$ = CH$_2$F, R$^2$ = H |
| 1065 | J = J-1b, Q = C(=O), R$^1$ = OMe, R$^2$ = H |
| 1066 | J = J-1b, Q = C(=O), R$^1$ = OEt, R$^2$ = H |
| 1067 | J = J-1b, Q = C(=O), R$^1$ = NHMe, R$^2$ = H |
| 1068 | J = J-1b, Q = C(=O), R$^1$ = NHEt, R$^2$ = H |
| 1069 | J = J-1b, Q = C(=O), R$^1$ = NMe$_2$, R$^2$ = H |
| 1070 | J = J-1b, Q = C(=O), R$^1$ = NEt$_2$, R$^2$ = H |
| 1071 | J = J-1b, Q = C(=O), R$^1$ = NMeEt, R$^2$ = H |
| 1072 | J = J-1b, Q = C(=O), R$^1$ = Cl, R$^2$ = H |
| 1073 | J = J-1b, Q = C(=O), R$^1$ = Br, R$^2$ = H |
| 1074 | J = J-1b, Q = C(=O), R$^1$ = H, R$^2$ = Me |
| 1075 | J = J-1b, Q = C(=O), R$^1$ = H, R$^2$ = Et |
| 1076 | J = J-1b, Q = C(=O), R$^1$ = H, R$^2$ = n-Pr |
| 1077 | J = J-1b, Q = C(=O), R$^1$ = H, R$^2$ = CH$_2$OMe |
| 1078 | J = J-1b, Q = C(=O), R$^1$ = H, R$^2$ = OMe |
| 1079 | J = J-1b, Q = C(=O), R$^1$ = H, R$^2$ = OEt |
| 1080 | J = J-1b, Q = C(=O), R$^1$ = H, R$^2$ = NHMe |
| 1081 | J = J-1b, Q = C(=O), R$^1$ = H, R$^2$ = NHEt |
| 1082 | J = J-1b, Q = C(=O), R$^1$ = H, R$^2$ = NMe$_2$ |
| 1083 | J = J-1b, Q = C(=O), R$^1$ = H, R$^2$ = NEt$_2$ |
| 1084 | J = J-1b, Q = C(=O), R$^1$ = H, R$^2$ = NMeEt |
| 1085 | j = J-1b, q = C(=O), R$^1$ = H, R$^2$ = Cl |
| 1086 | J = J-1b, Q = C(=O), R$^1$ = H, R$^2$ = Br |
| 1087 | J = J-1b, Q = C(=O), R$^1$ = Me, R$^2$ = Me |
| 1088 | J = J-1b, Q = C(=O), R$^1$, R$^2$ = —(CH$_2$)$_3$— |
| 1089 | J = J-1b, Q = C(=O), R$^1$, R$^2$ = —(CH$_2$)$_4$— |
| 1090 | J = J-10a, Q = O, R$^1$ = Me, R$^2$ = H |
| 1091 | J = J-10a, Q = O, R$^1$ = Et, R$^2$ = H |
| 1092 | J = J-10a, Q = O, R$^1$ = n-Pr, R$^2$ = H |
| 1093 | J = J-10a, Q = O, R$^1$ = CH$_2$OMe, R$^2$ = H |
| 1094 | J = J-10a, Q = O, R$^1$ = CH$_2$F, R$^2$ = H |
| 1095 | J = J-10a, Q = O, R$^1$ = OMe, R$^2$ = H |
| 1096 | J = J-10a, Q = O, R$^1$ = OEt, R$^2$ = H |
| 1097 | J = J-10a, Q = O, R$^1$ = NHMe, R$^2$ = H |
| 1098 | J = J-10a, Q = O, R$^1$ = NHEt, R$^2$ = H |
| 1099 | J = J-10a, Q = O, R$^1$ = NMe$_2$, R$^2$ = H |
| 1100 | J = J-10a, Q = O, R$^1$ = NEt$_2$, R$^2$ = H |
| 1101 | J = J-10a, Q = O, R$^1$ = NMeEt, R$^2$ = H |
| 1102 | J = J-10a, Q = O, R$^1$ = Cl, R$^2$ = H |
| 1103 | J = J-10a, Q = O, R$^1$ = Br, R$^2$ = H |
| 1104 | J = J-10a, Q = O, R$^1$ = H, R$^2$ = Me |
| 1105 | J = J-10a, Q = O, R$^1$ = H, R$^2$ = Et |
| 1106 | J = J-10a, Q = O, R$^1$ = H, R$^2$ = n-Pr |
| 1107 | J = J-10a, Q = O, R$^1$ = H, R$^2$ = CH$_2$OMe |
| 1108 | J = J-10a, Q = O, R$^1$ = H, R$^2$ = OMe |
| 1109 | J = J-10a, Q = O, R$^1$ = H, R$^2$ = OEt |
| 1110 | J = J-10a, Q = O, R$^1$ = H, R$^2$ = NHMe |
| 1111 | J = J-10a, Q = O, R$^1$ = H, R$^2$ = NHEt |
| 1112 | J = J-10a, Q = O, R$^1$ = H, R$^2$ = NMe$_2$ |
| 1113 | J = J-10a, Q = O, R$^1$ = H, R$^2$ = NEt$_2$ |
| 1114 | J = J-10a, Q = O, R$^1$ = H, R$^2$ = NMeEt |
| 1115 | J = J-10a, Q = O, R$^1$ = H, R$^2$ = Cl |
| 1116 | J = J-10a, Q = O, R$^1$ = H, R$^2$ = Br |
| 1117 | J = J-10a, Q = O, R$^1$ = Me, R$^2$ = Me |
| 1118 | J = J-10a, Q = O, R$^1$, R$^2$ = —(CH$_2$)$_3$— |
| 1119 | J = J-10a, Q = O, R$^1$, R$^2$ = —(CH$_2$)$_4$— |
| 1120 | J = J-10a, Q = CH$_2$, R$^1$ = Me, R$^2$ = H |
| 1121 | J = J-10a, Q = CH$_2$, R$^1$ = Et, R$^2$ = H |
| 1122 | J = J-10a, Q = CH$_2$, R$^1$ = n-Pr, R$^2$ = H |
| 1123 | J = J-10a, Q = CH$_2$, R$^1$ = CH$_2$OMe, R$^2$ = H |
| 1124 | J = J-10a, Q = CH$_2$, R$^1$ = CH$_2$F, R$^2$ = H |
| 1125 | J = J-10a, Q = CH$_2$, R$^1$ = OMe, R$^2$ = H |
| 1126 | J = J-10a, Q = CH$_2$, R$^1$ = OEt, R$^2$ = H |
| 1127 | J = J-10a, Q = CH$_2$, R$^1$ = NHMe, R$^2$ = H |
| 1128 | J = J-10a, Q = CH$_2$, R$^1$ = NHEt, R$^2$ = H |
| 1129 | J = J-10a, Q = CH$_2$, R$^1$ = NMe$_2$, R$^2$ = H |
| 1130 | J = J-10a, Q = CH$_2$, R$^1$ = NEt$_2$, R$^2$ = H |
| 1131 | J = J-10a, Q = CH$_2$, R$^1$ = NMeEt, R$^2$ = H |
| 1132 | J = J-10a, Q = CH$_2$, R$^1$ = Cl, R$^2$ = H |
| 1133 | J = J-10a, Q = CH$_2$, R$^1$ = Br, R$^2$ = H |
| 1134 | J = J-10a, Q = CH$_2$, R$^1$ = H, R$^2$ = Me |
| 1135 | J = J-10a, Q = CH$_2$, R$^1$ = H, R$^2$ = Et |
| 1136 | J = J-10a, Q = CH$_2$, R$^1$ = H, R$^2$ = n-Pr |
| 1137 | J = J-10a, Q = CH$_2$, R$^1$ = H, R$^2$ = CH$_2$OMe |
| 1138 | J = J-10a, Q = CH$_2$, R$^1$ = H, R$^2$ = OMe |
| 1139 | J = J-10a, Q = CH$_2$, R$^1$ = H, R$^2$ = OEt |
| 1140 | J = J-10a, Q = CH$_2$, R$^1$ = H, R$^2$ = NHMe |
| 1141 | J = J-10a, Q = CH$_2$, R$^1$ = H, R$^2$ = NHEt |
| 1142 | J = J-10a, Q = CH$_2$, R$^1$ = H, R$^2$ = NMe$_2$ |
| 1143 | J = J-10a, Q = CH$_2$, R$^1$ = H, R$^2$ = NEt$_2$ |
| 1144 | J = J-10a, Q = CH$_2$, R$^1$ = H, R$^2$ = NMeEt |
| 1145 | J = J-10a, Q = CH$_2$, R$^1$ = H, R$^2$ = Cl |
| 1146 | J = J-10a, Q = CH$_2$, R$^1$ = H, R$^2$ = Br |
| 1147 | J = J-10a, Q = CH$_2$, R$^1$ = Me, R$^2$ = Me |
| 1148 | J = J-10a, Q = CH$_2$, R$^1$, R$^2$ = —(CH$_2$)$_3$— |
| 1149 | J = J-10a, Q = CH$_2$, R$^1$, R$^2$ = —(CH$_2$)$_4$— |
| 1150 | J = J-10a, Q = C(=O), R$^1$ = Me, R$^2$ = H |
| 1151 | J = J-10a, Q = C(=O), R$^1$ = Et, R$^2$ = H |
| 1152 | J = J-10a, Q = C(=O), R$^1$ = n-Pr, R$^2$ = H |
| 1153 | J = J-10a, Q = C(=O), R$^1$ = CH$_2$OMe, R$^2$ = H |
| 1154 | J = J-10a, Q = C(=O), R$^1$ = CH$_2$F, R$^2$ = H |
| 1155 | J = J-10a, Q = C(=O), R$^1$ = OMe, R$^2$ = H |
| 1156 | J = J-10a, Q = C(=O), R$^1$ = OEt, R$^2$ = H |
| 1157 | J = J-10a, Q = C(=O), R$^1$ = NHMe, R$^2$ = H |
| 1158 | J = J-10a, Q = C(=O), R$^1$ = NHEt, R$^2$ = H |
| 1159 | J = J-10a, Q = C(=O), R$^1$ = NMe$_2$, R$^2$ = H |
| 1160 | J = J-10a, Q = C(=O), R$^1$ = NEt$_2$, R$^2$ = H |
| 1161 | J = J-10a, Q = C(=O), R$^1$ = NMeEt, R$^2$ = H |
| 1162 | J = J-10a, Q = C(=O), R$^1$ = Cl, R$^2$ = H |
| 1163 | J = J-10a, Q = C(=O), R$^1$ = Br, R$^2$ = H |
| 1164 | J = J-10a, Q = C(=O), R$^1$ = H, R$^2$ = Me |
| 1165 | J = J-10a, Q = C(=O), R$^1$ = H, R$^2$ = Et |
| 1166 | J = J-10a, Q = C(=O), R$^1$ = H, R$^2$ = n-Pr |
| 1167 | J = J-10a, Q = C(=O), R$^1$ = H, R$^2$ = CH$_2$OMe |
| 1168 | J = J-10a, Q = C(=O), R$^1$ = H, R$^2$ = OMe |
| 1169 | J = J-10a, Q = C(=O), R$^1$ = H, R$^2$ = OEt |
| 1170 | J = J-10a, Q = C(=O), R$^1$ = H, R$^2$ = NHMe |
| 1171 | J = J-10a, Q = C(=O), R$^1$ = H, R$^2$ = NHEt |
| 1172 | J = J-10a, Q = C(=O), R$^1$ = H, R$^2$ = NMe$_2$ |
| 1173 | J = J-10a, Q = C(=O), R$^1$ = H, R$^2$ = NEt$_2$ |
| 1174 | J = J-10a, Q = C(=O), R$^1$ = H, R$^2$ = NMeEt |
| 1175 | J = J-10a, Q = C(=O), R$^1$ = H, R$^2$ = Cl |

TABLE 1450-continued

| Table | Row Heading |
|---|---|
| 1176 | J = J-10a, Q = C(=O), $R^1$ = H, $R^2$ = Br |
| 1177 | J = J-10a, Q = C(=O), $R^1$ = Me, $R^2$ = Me |
| 1178 | J = J-10a, Q = C(=O), $R^1$, $R^2$ = —(CH$_2$)$_3$— |
| 1179 | J = J-10a, Q = C(=O), $R^1$, $R^2$ = —(CH$_2$)$_4$— |
| 1180 | J = J-29a, Q = O, $R^1$ = Me, $R^2$ = H |
| 1181 | J = J-29a, Q = O, $R^1$ = Et, $R^2$ = H |
| 1182 | J = J-29a, Q = O, $R^1$ = n-Pr, $R^2$ = H |
| 1183 | J = J-29a, Q = O, $R^1$ = CH$_2$OMe, $R^2$ = H |
| 1184 | J = J-29a, Q = O, $R^1$ = CH$_2$F, $R^2$ = H |
| 1185 | J = J-29a, Q = O, $R^1$ = OMe, $R^2$ = H |
| 1186 | J = J-29a, Q = O, $R^1$ = OEt, $R^2$ = H |
| 1187 | J = J-29a, Q = O, $R^1$ = NHMe, $R^2$ = H |
| 1188 | J = J-29a, Q = O, $R^1$ = NHEt, $R^2$ = H |
| 1189 | J = J-29a, Q = O, $R^1$ = NMe$_2$, $R^2$ = H |
| 1190 | J = J-29a, Q = O, $R^1$ = NEt$_2$, $R^2$ = H |
| 1191 | J = J-29a, Q = O, $R^1$ = NMeEt, $R^2$ = H |
| 1192 | J = J-29a, Q = O, $R^1$ = Cl, $R^2$ = H |
| 1193 | J = J-29a, Q = O, $R^1$ = Br, $R^2$ = H |
| 1194 | J = J-29a, Q = O, $R^1$ = H, $R^2$ = Me |
| 1195 | J = J-29a, Q = O, $R^1$ = H, $R^2$ = Et |
| 1196 | J = J-29a, Q = O, $R^1$ = H, $R^2$ = n-Pr |
| 1197 | J = J-29a, Q = O, $R^1$ = H, $R^2$ = CH$_2$OMe |
| 1198 | J = J-29a, Q = O, $R^1$ = H, $R^2$ = OMe |
| 1199 | J = J-29a, Q = O, $R^1$ = H, $R^2$ = OEt |
| 1200 | J = J-29a, Q = O, $R^1$ = H, $R^2$ = NHMe |
| 1201 | J = J-29a, Q = O, $R^1$ = H, $R^2$ = NHEt |
| 1202 | J = J-29a, Q = O, $R^1$ = H, $R^2$ = NMe$_2$ |
| 1203 | J = J-29a, Q = O, $R^1$ = H, $R^2$ = NEt$_2$ |
| 1204 | J = J-29a, Q = O, $R^1$ = H, $R^2$ = NMeEt |
| 1205 | J = J-29a, Q = O, $R^1$ = H, $R^2$ = Cl |
| 1206 | J = J-29a, Q = O, $R^1$ = H, $R^2$ = Br |
| 1207 | J = J-29a, Q = O, $R^1$ = Me, $R^2$ = Me |
| 1208 | J = J-29a, Q = O, $R^1$, $R^2$ = —(CH$_2$)$_3$— |
| 1209 | J = J-29a, Q = O, $R^1$, $R^2$ = —(CH$_2$)$_4$— |
| 1210 | J = J-29a, Q = CH$_2$, $R^1$ = Me, $R^2$ = H |
| 1211 | J = J-29a, Q = CH$_2$, $R^1$ = Et, $R^2$ = H |
| 1212 | J = J-29a, Q = CH$_2$, $R^1$ = n-Pr, $R^2$ = H |
| 1213 | J = J-29a, Q = CH$_2$, $R^1$ = CH$_2$OMe, $R^2$ = H |
| 1214 | J = J-29a, Q = CH$_2$, $R^1$ = CH$_2$F, $R^2$ = H |
| 1215 | J = J-29a, Q = CH$_2$, $R^1$ = OMe, $R^2$ = H |
| 1216 | J = J-29a, Q = CH$_2$, $R^1$ = OEt, $R^2$ = H |
| 1217 | J = J-29a, Q = CH$_2$, $R^1$ = NHMe, $R^2$ = H |
| 1218 | J = J-29a, Q = CH$_2$, $R^1$ = NHEt, $R^2$ = H |
| 1219 | J = J-29a, Q = CH$_2$, $R^1$ = NMe$_2$, $R^2$ = H |
| 1220 | J = J-29a, Q = CH$_2$, $R^1$ = NEt$_2$, $R^2$ = H |
| 1221 | J = J-29a, Q = CH$_2$, $R^1$ = NMeEt, $R^2$ = H |
| 1222 | J = J-29a, Q = CH$_2$, $R^1$ = Cl, $R^2$ = H |
| 1223 | J = J-29a, Q = CH$_2$, $R^1$ = Br, $R^2$ = H |
| 1224 | J = J-29a, Q = CH$_2$, $R^1$ = H, $R^2$ = Me |
| 1225 | J = J-29a, Q = CH$_2$, $R^1$ = H, $R^2$ = Et |
| 1226 | J = J-29a, Q = CH$_2$, $R^1$ = H, $R^2$ = n-Pr |
| 1227 | J = J-29a, Q = CH$_2$, $R^1$ = H, $R^2$ = CH$_2$OMe |
| 1228 | J = J-29a, Q = CH$_2$, $R^1$ = H, $R^2$ = OMe |
| 1229 | J = J-29a, Q = CH$_2$, $R^1$ = H, $R^2$ = OEt |
| 1230 | J = J-29a, Q = CH$_2$, $R^1$ = H, $R^2$ = NHMe |
| 1231 | J = J-29a, Q = CH$_2$, $R^1$ = H, $R^2$ = NHEt |
| 1232 | J = J-29a, Q = CH$_2$, $R^1$ = H, $R^2$ = NMe$_2$ |
| 1233 | J = J-29a, Q = CH$_2$, $R^1$ = H, $R^2$ = NEt$_2$ |
| 1234 | J = J-29a, Q = CH$_2$, $R^1$ = H, $R^2$ = NMeEt |
| 1235 | J = J-29a, Q = CH$_2$, $R^1$ = H, $R^2$ = Cl |
| 1236 | J = J-29a, Q = CH$_2$, $R^1$ = H, $R^2$ = Br |
| 1237 | J = J-29a, Q = CH$_2$, $R^1$ = Me, $R^2$ = Me |
| 1238 | J = J-29a, Q = CH$_2$, $R^1$, $R^2$ = —(CH$_2$)$_3$— |
| 1239 | J = J-29a, Q = CH$_2$, $R^1$, $R^2$ = —(CH$_2$)$_4$— |
| 1240 | J = J-29a, Q = C(=O), $R^1$ = Me, $R^2$ = H |
| 1241 | J = J-29a, Q = C(=O), $R^1$ = Et, $R^2$ = H |
| 1242 | J = J-29a, Q = C(=O), $R^1$ = n-Pr, $R^2$ = H |
| 1243 | J = J-29a, Q = C(=O), $R^1$ = CH$_2$OMe, $R^2$ = H |
| 1244 | J = J-29a, Q = C(=O), $R^1$ = CH$_2$F, $R^2$ = H |
| 1245 | J = J-29a, Q = C(=O), $R^1$ = OMe, $R^2$ = H |
| 1246 | J = J-29a, Q = C(=O), $R^1$ = OEt, $R^2$ = H |
| 1247 | J = J-29a, Q = C(=O), $R^1$ = NHMe, $R^2$ = H |
| 1248 | J = J-29a, Q = C(=O), $R^1$ = NHEt, $R^2$ = H |
| 1249 | J = J-29a, Q = C(=O), $R^1$ = NMe$_2$, $R^2$ = H |
| 1250 | J = J-29a, Q = C(=O), $R^1$ = NEt$_2$, $R^2$ = H |
| 1251 | J = J-29a, Q = C(=O), $R^1$ = NMeEt, $R^2$ = H |
| 1252 | J = J-29a, Q = C(=O), $R^1$ = Cl, $R^2$ = H |
| 1253 | J = J-29a, Q = C(=O), $R^1$ = Br, $R^2$ = H |
| 1254 | J = J-29a, Q = C(=O), $R^1$ = H, $R^2$ = Me |
| 1255 | J = J-29a, Q = C(=O), $R^1$ = H, $R^2$ = Et |
| 1256 | J = J-29a, Q = C(=O), $R^1$ = H, $R^2$ = n-Pr |
| 1257 | J = J-29a, Q = C(=O), $R^1$ = H, $R^2$ = CH$_2$OMe |
| 1258 | J = J-29a, Q = C(=O), $R^1$ = H, $R^2$ = OMe |
| 1259 | J = J-29a, Q = C(=O), $R^1$ = H, $R^2$ = OEt |
| 1260 | J = J-29a, Q = C(=O), $R^1$ = H, $R^2$ = NHMe |
| 1261 | J = J-29a, Q = C(=O), $R^1$ = H, $R^2$ = NHEt |
| 1262 | J = J-29a, Q = C(=O), $R^1$ = H, $R^2$ = NMe$_2$ |
| 1263 | J = J-29a, Q = C(=O), $R^1$ = H, $R^2$ = NEt$_2$ |
| 1264 | J = J-29a, Q = C(=O), $R^1$ = H, $R^2$ = NMeEt |
| 1265 | J = J-29a, Q = C(=O), $R^1$ = H, $R^2$ = Cl |
| 1266 | J = J-29a, Q = C(=O), $R^1$ = H, $R^2$ = Br |
| 1267 | J = J-29a, Q = C(=O), $R^1$ = Me, $R^2$ = Me |
| 1268 | J = J-29a, Q = C(=O), $R^1$, $R^2$ = —(CH$_2$)$_3$— |
| 1269 | J = J-29a, Q = C(=O), $R^1$, $R^2$ = —(CH$_2$)$_4$— |
| 1270 | J = J-33A, Q = O, $R^1$ = Me, $R^2$ = H |
| 1271 | J = J-33A, Q = O, $R^1$ = Et, $R^2$ = H |
| 1272 | J = J-33A, Q = O, $R^1$ = n-Pr, $R^2$ = H |
| 1273 | J = J-33A, Q = O, $R^1$ = CH$_2$OMe, $R^2$ = H |
| 1274 | J = J-33A, Q = O, $R^1$ = CH$_2$F, $R^2$ = H |
| 1275 | J = J-33A, Q = O, $R^1$ = OMe, $R^2$ = H |
| 1276 | J = J-33A, Q = O, $R^1$ = OEt, $R^2$ = H |
| 1277 | J = J-33A, Q = O, $R^1$ = NHMe, $R^2$ = H |
| 1278 | J = J-33A, Q = O, $R^1$ = NHEt, $R^2$ = H |
| 1279 | J = J-33A, Q = O, $R^1$ = NMe$_2$, $R^2$ = H |
| 1280 | J = J-33A, Q = O, $R^1$ = NEt$_2$, $R^2$ = H |
| 1281 | J = J-33A, Q = O, $R^1$ = NMeEt, $R^2$ = H |
| 1282 | J = J-33A, Q = O, $R^1$ = Cl, $R^2$ = H |
| 1283 | J = J-33A, Q = O, $R^1$ = Br, $R^2$ = H |
| 1284 | J = J-33A, Q = O, $R^1$ = H, $R^2$ = Me |
| 1285 | J = J-33A, Q = O, $R^1$ = H, $R^2$ = Et |
| 1286 | J = J-33A, Q = O, $R^1$ = H, $R^2$ = n-Pr |
| 1287 | J = J-33A, Q = O, $R^1$ = H, $R^2$ = CH$_2$OMe |
| 1288 | J = J-33A, Q = O, $R^1$ = H, $R^2$ = OMe |
| 1289 | J = J-33A, Q = O, $R^1$ = H, $R^2$ = OEt |
| 1290 | J = J-33A, Q = O, $R^1$ = H, $R^2$ = NHMe |
| 1291 | J = J-33A, Q = O, $R^1$ = H, $R^2$ = NHEt |
| 1292 | J = J-33A, Q = O, $R^1$ = H, $R^2$ = NMe$_2$ |
| 1293 | J = J-33A, Q = O, $R^1$ = H, $R^2$ = NEt$_2$ |
| 1294 | J = J-33A, Q = O, $R^1$ = H, $R^2$ = NMeEt |
| 1295 | J = J-33A, Q = O, $R^1$ = H, $R^2$ = Cl |
| 1296 | J = J-33A, Q = O, $R^1$ = H, $R^2$ = Br |
| 1297 | J = J-33A, Q = O, $R^1$ = Me, $R^2$ = Me |
| 1298 | J = J-33A, Q = O, $R^1$, $R^2$ = —(CH$_2$)$_3$— |
| 1299 | J = J-33A, Q = O, $R^1$, $R^2$ = —(CH$_2$)$_4$— |
| 1300 | J = J-33A, Q = CH$_2$, $R^1$ = Me, $R^2$ = H |
| 1301 | J = J-33A, Q = CH$_2$, $R^1$ = Et, $R^2$ = H |
| 1302 | J = J-33A, Q = CH$_2$, $R^1$ = n-Pr, $R^2$ = H |
| 1303 | J = J-33A, Q = CH$_2$, $R^1$ = CH$_2$OMe, $R^2$ = H |
| 1304 | J = J-33A, Q = CH$_2$, $R^1$ = CH$_2$F, $R^2$ = H |
| 1305 | J = J-33A, Q = CH$_2$, $R^1$ = OMe, $R^2$ = H |
| 1306 | J = J-33A, Q = CH$_2$, $R^1$ = OEt, $R^2$ = H |
| 1307 | J = J-33A, Q = CH$_2$, $R^1$ = NHMe, $R^2$ = H |
| 1308 | J = J-33A, Q = CH$_2$, $R^1$ = NHEt, $R^2$ = H |
| 1309 | J = J-33A, Q = CH$_2$, $R^1$ = NMe$_2$, $R^2$ = H |
| 1310 | J = J-33A, Q = CH$_2$, $R^1$ = NEt$_2$, $R^2$ = H |
| 1311 | J = J-33A, Q = CH$_2$, $R^1$ = NMeEt, $R^2$ = H |
| 1312 | J = J-33A, Q = CH$_2$, $R^1$ = Cl, $R^2$ = H |
| 1313 | J = J-33A, Q = CH$_2$, $R^1$ = Br, $R^2$ = H |
| 1314 | J = J-33A, Q = CH$_2$, $R^1$ = H, $R^2$ = Me |
| 1315 | J = J-33A, Q = CH$_2$, $R^1$ = H, $R^2$ = Et |
| 1316 | J = J-33A, Q = CH$_2$, $R^1$ = H, $R^2$ = n-Pr |
| 1317 | J = J-33A, Q = CH$_2$, $R^1$ = H, $R^2$ = CH$_2$OMe |
| 1318 | J = J-33A, Q = CH$_2$, $R^1$ = H, $R^2$ = OMe |
| 1319 | J = J-33A, Q = CH$_2$, $R^1$ = H, $R^2$ = OEt |
| 1320 | J = J-33A, Q = CH$_2$, $R^1$ = H, $R^2$ = NHMe |
| 1321 | J = J-33A, Q = CH$_2$, $R^1$ = H, $R^2$ = NHEt |
| 1322 | J = J-33A, Q = CH$_2$, $R^1$ = H, $R^2$ = NMe$_2$ |
| 1323 | J = J-33A, Q = CH$_2$, $R^1$ = H, $R^2$ = NEt$_2$ |
| 1324 | J = J-33A, Q = CH$_2$, $R^1$ = H, $R^2$ = NMeEt |
| 1325 | J = J-33A, Q = CH$_2$, $R^1$ = H, $R^2$ = Cl |
| 1326 | J = J-33A, Q = CH$_2$, $R^1$ = H, $R^2$ = Br |
| 1327 | J = J-33A, Q = CH$_2$, $R^1$ = Me, $R^2$ = Me |
| 1328 | J = J-33A, Q = CH$_2$, $R^1$, $R^2$ = —(CH$_2$)$_3$— |
| 1329 | J = J-33A, Q = CH$_2$, $R^1$, $R^2$ = —(CH$_2$)$_4$— |
| 1330 | J = J-33A, Q = C(=O), $R^1$ = Me, $R^2$ = H |
| 1331 | J = J-33A, Q = C(=O), $R^1$ = Et, $R^2$ = H |

TABLE 1450-continued

| Table | Row Heading |
|---|---|
| 1332 | J = J-33A, Q = C(=O), R$^1$ = n-Pr, R$^2$ = H |
| 1333 | J = J-33A, Q = C(=O), R$^1$ = CH$_2$OMe, R$^2$ = H |
| 1334 | J = J-33A, Q = C(=O), R$^1$ = CH$_2$F, R$^2$ = H |
| 1335 | J = J-33A, Q = C(=O), R$^1$ = OMe, R$^2$ = H |
| 1336 | J = J-33A, Q = C(=O), R$^1$ = OEt, R$^2$ = H |
| 1337 | J = J-33A, Q = C(=O), R$^1$ = NHMe, R$^2$ = H |
| 1338 | J = J-33A, Q = C(=O), R$^1$ = NHEt, R$^2$ = H |
| 1339 | J = J-33A, Q = C(=O), R$^1$ = NMe$_2$, R$^2$ = H |
| 1340 | J = J-33A, Q = C(=O), R$^1$ = NEt$_2$, R$^2$ = H |
| 1341 | J = J-33A, Q = C(=O), R$^1$ = NMeEt, R$^2$ = H |
| 1342 | J = J-33A, Q = C(=O), R$^1$ = Cl, R$^2$ = H |
| 1343 | J = J-33A, Q = C(=O), R$^1$ = Br, R$^2$ = H |
| 1344 | J = J-33A, Q = C(=O), R$^1$ = H, R$^2$ = Me |
| 1345 | J = J-33A, Q = C(=O), R$^1$ = H, R$^2$ = Et |
| 1346 | J = J-33A, Q = C(=O), R$^1$ = H, R$^2$ = n-Pr |
| 1347 | J = J-33A, Q = C(=O), R$^1$ = H, R$^2$ = CH$_2$OMe |
| 1348 | J = J-33A, Q = C(=O), R$^1$ = H, R$^2$ = OMe |
| 1349 | J = J-33A, Q = C(=O), R$^1$ = H, R$^2$ = OEt |
| 1350 | J = J-33A, Q = C(=O), R$^1$ = H, R$^2$ = NHMe |
| 1351 | J = J-33A, Q = C(=O), R$^1$ = H, R$^2$ = NHEt |
| 1352 | J = J-33A, Q = C(=O), R$^1$ = H, R$^2$ = NMe$_2$ |
| 1353 | J = J-33A, Q = C(=O), R$^1$ = H, R$^2$ = NEt$_2$ |
| 1354 | J = J-33A, Q = C(=O), R$^1$ = H, R$^2$ = NMeEt |
| 1355 | J = J-33A, Q = C(=O), R$^1$ = H, R$^2$ = Cl |
| 1356 | J = J-33A, Q = C(=O), R$^1$ = H, R$^2$ = Br |
| 1357 | J = J-33A, Q = C(=O), R$^1$ = Me, R$^2$ = Me |
| 1358 | J = J-33A, Q = C(=O), R$^1$, R$^2$ = —(CH$_2$)$_3$— |
| 1359 | J = J-33A, Q = C(=O), R$^1$, R$^2$ = —(CH$_2$)$_4$— |
| 1360 | J = J-18b, Q = O, R$^1$ = Me, R$^2$ = H |
| 1361 | J = J-18b, Q = O, R$^1$ = Et, R$^2$ = H |
| 1362 | J = J-18b, Q = O, R$^1$ = n-Pr, R$^2$ = H |
| 1363 | J = J-18b, Q = O, R$^1$ = CH$_2$Me, R$^2$ = H |
| 1364 | J = J-18b, Q = O, R$^1$ = CH$_2$F, R$^2$ = H |
| 1365 | J = J-18b, Q = O, R$^1$ = OMe, R$^2$ = H |
| 1366 | J = J-18b, Q = O, R$^1$ = OEt, R$^2$ = H |
| 1367 | J = J-18b, Q = O, R$^1$ = NHMe, R$^2$ = H |
| 1368 | J = J-18b, Q = O, R$^1$ = NHEt, R$^2$ = H |
| 1369 | J = J-18b, Q = O, R$^1$ = NMe$_2$, R$^2$ = H |
| 1370 | J = J-18b, Q = O, R$^1$ = NEt$_2$, R$^2$ = H |
| 1371 | J = J-18b, Q = O, R$^1$ = NMeEt, R$^2$ = H |
| 1372 | J = J-18b, Q = O, R$^1$ = Cl, R$^2$ = H |
| 1373 | J = J-18b, Q = O, R$^1$ = Br, R$^2$ = H |
| 1374 | J = J-18b, Q = O, R$^1$ = H, R$^2$ = Me |
| 1375 | J = J-18b, Q = O, R$^1$ = H, R$^2$ = Et |
| 1376 | J = J-18b, Q = O, R$^1$ = H, R$^2$ = n-Pr |
| 1377 | J = J-18b, Q = O, R$^1$ = H, R$^2$ = CH$_2$OMe |
| 1378 | J = J-18b, Q = O, R$^1$ = H, R$^2$ = OMe |
| 1379 | J = J-18b, Q = O, R$^1$ = H, R$^2$ = OEt |
| 1380 | J = J-18b, Q = O, R$^1$ = H, R$^2$ = NHMe |
| 1381 | J = J-18b, Q = O, R$^1$ = H, R$^2$ = NHEt |
| 1382 | J = J-18b, Q = O, R$^1$ = H, R$^2$ = NMe$_2$ |
| 1383 | J = J-18b, Q = O, R$^1$ = H, R$^2$ = NEt$_2$ |
| 1384 | J = J-18b, Q = O, R$^1$ = H, R$^2$ = NMeEt |
| 1385 | J = J-18b, Q = O, R$^1$ = H, R$^2$ = Cl |
| 1386 | J = J-18b, Q = O, R$^1$ = H, R$^2$ = Br |
| 1387 | J = J-18b, Q = O, R$^1$ = Me, R$^2$ = Me |
| 1388 | J = J-18b, Q = O, R$^1$, R$^2$ = —(CH$_2$)$_3$— |
| 1389 | J = J-18b, Q = O, R$^1$, R$^2$ = —(CH$_2$)$_4$— |
| 1390 | J = J-18b, Q = CH$_2$, R$^1$ = Me, R$^2$ = H |
| 1391 | J = J-18b, Q = CH$_2$, R$^1$ = Et, R$^2$ = H |
| 1392 | J = J-18b, Q = CH$_2$, R$^1$ = n-Pr, R$^2$ = H |
| 1393 | J = J-18b, Q = CH$_2$, R$^1$ = CH$_2$OMe, R$^2$ = H |
| 1394 | J = J-18b, Q = CH$_2$, R$^1$ = CH$_2$F, R$^2$ = H |
| 1395 | J = J-18b, Q = CH$_2$, R$^1$ = OMe, R$^2$ = H |
| 1396 | J = J-18b, Q = CH$_2$, R$^1$ = OEt, R$^2$ = H |
| 1397 | J = J-18b, Q = CH$_2$, R$^1$ = NHMe, R$^2$ = H |
| 1398 | J = J-18b, Q = CH$_2$, R$^1$ = NHEt, R$^2$ = H |
| 1399 | J = J-18b, Q = CH$_2$, R$^1$ = NMe$_2$, R$^2$ = H |
| 1400 | J = J-18b, Q = CH$_2$, R$^1$ = NEt$_2$, R$^2$ = H |
| 1401 | J = J-18b, Q = CH$_2$, R$^1$ = NMeEt, R$^2$ = H |
| 1402 | J = J-18b, Q = CH$_2$, R$^1$ = Cl, R$^2$ = H |
| 1403 | J = J-18b, Q = CH$_2$, R$^1$ = Br, R$^2$ = H |
| 1404 | J = J-18b, Q = CH$_2$, R$^1$ = H, R$^2$ = Me |
| 1405 | J = J-18b, Q = CH$_2$, R$^1$ = H, R$^2$ = Et |
| 1406 | J = J-18b, Q = CH$_2$, R$^1$ = H, R$^2$ = n-Pr |
| 1407 | J = J-18b, Q = CH$_2$, R$^1$ = H, R$^2$ = CH$_2$OMe |
| 1408 | J = J-18b, Q = CH$_2$, R$^1$ = H, R$^2$ = OMe |
| 1409 | J = J-18b, Q = CH$_2$, R$^1$ = H, R$^2$ = OEt |

TABLE 1450-continued

| Table | Row Heading |
|---|---|
| 1410 | J = J-18b, Q = CH$_2$, R$^1$ = H, R$^2$ = NHMe |
| 1411 | J = J-18b, Q = CH$_2$, R$^1$ = H, R$^2$ = NHEt |
| 1412 | J = J-18b, Q = CH$_2$, R$^1$ = H, R$^2$ = NMe$_2$ |
| 1413 | J = J-18b, Q = CH$_2$, R$^1$ = H, R$^2$ = NEt$_2$ |
| 1414 | J = J-18b, Q = CH$_2$, R$^1$ = H, R$^2$ = NMeEt |
| 1415 | J = J-18b, Q = CH$_2$, R$^1$ = H, R$^2$ = Cl |
| 1416 | J = J-18b, Q = CH$_2$, R$^1$ = H, R$^2$ = Br |
| 1417 | J = J-18b, Q = CH$_2$, R$^1$ = Me, R$^2$ = Me |
| 1418 | J = J-18b, Q = CH$_2$, R$^1$, R$^2$ = —(CH$_2$)$_3$— |
| 1419 | J = J-18b, Q = CH$_2$, R$^1$, R$^2$ = —(CH$_2$)$_4$— |
| 1420 | J = J-18b, Q = C(=O), R$^1$ = Me, R$^2$ = H |
| 1421 | J = J-18b, Q = C(=O), R$^1$ = Et, R$^2$ = H |
| 1422 | J = J-18b, Q = C(=O), R$^1$ = n-Pr, R$^2$ = H |
| 1423 | J = J-18b, Q = C(=O), R$^1$ = CH$_2$OMe, R$^2$ = H |
| 1424 | J = J-18b, Q = C(=O), R$^1$ = CH$_2$F, R$^2$ = H |
| 1425 | J = J-18b, Q = C(=O), R$^1$ = OMe, R$^2$ = H |
| 1426 | J = J-18b, Q = C(=O), R$^1$ = OEt, R$^2$ = H |
| 1427 | J = J-18b, Q = C(=O), R$^1$ = NHMe, R$^2$ = H |
| 1428 | J = J-18b, Q = C(=O), R$^1$ = NHEt, R$^2$ = H |
| 1429 | J = J-18b, Q = C(=O), R$^1$ = NMe$_2$, R$^2$ = H |
| 1430 | J = J-18b, Q = C(=O), R$^1$ = NEt$_2$, R$^2$ = H |
| 1431 | J = J-18b, Q = C(=O), R$^1$ = NMeEt, R$^2$ = H |
| 1432 | J = J-18b, Q = C(=O), R$^1$ = Cl, R$^2$ = H |
| 1433 | J = J-18b, Q = C(=O), R$^1$ = Br, R$^2$ = H |
| 1434 | J = J-18b, Q = C(=O), R$^1$ = H, R$^2$ = Me |
| 1435 | J = J-18b, Q = C(=O), R$^1$ = H, R$^2$ = Et |
| 1436 | J = J-18b, Q = C(=O), R$^1$ = H, R$^2$ = n-Pr |
| 1437 | J = J-18b, Q = C(=O), R$^1$ = H, R$^2$ = CH$_2$OMe |
| 1438 | J = J-18b, Q = C(=O), R$^1$ = H, R$^2$ = OMe |
| 1439 | J = J-18b, Q = C(=O), R$^1$ = H, R$^2$ = OEt |
| 1440 | J = J-18b, Q = C(=O), R$^1$ = H, R$^2$ = NHMe |
| 1441 | J = J-18b, Q = C(=O), R$^1$ = H, R$^2$ = NHEt |
| 1442 | J = J-18b, Q = C(=O), R$^1$ = H, R$^2$ = NMe$_2$ |
| 1443 | J = J-18b, Q = C(=O), R$^1$ = H, R$^2$ = NEt$_2$ |
| 1444 | J = J-18b, Q = C(=O), R$^1$ = H, R$^2$ = NMeEt |
| 1445 | J = J-18b, Q = C(=O), R$^1$ = H, R$^2$ = Cl |
| 1446 | J = J-18b, Q = C(=O), R$^1$ = H, R$^2$ = Br |
| 1447 | J = J-18b, Q = C(=O), R$^1$ = Me, R$^2$ = Me |
| 1448 | J = J-18b, Q = C(=O), R$^1$, R$^2$ = —(CH$_2$)$_3$— |
| 1449 | J = J-18b, Q = C(=O), R$^1$, R$^2$ = —(CH$_2$)$_4$— |

Table 1450 is constructed in the same manner as Table 1, except the header row (i.e. J=J-1, Q=O, R$^1$=Me, R$^2$=H) is replaced with "Q=CH$_2$, J=J-10, R$^1$=Me, R$^2$ is H".

Tables 1451-1504 are constructed similarly to Table 2 using the A values listed in Table 1 above.

| Table | Row Heading |
|---|---|
| 1451 | J = J-18a, R$^1$ = Et, R$^2$ = H |
| 1452 | J = J-18a, R$^1$ = n-Pr, R$^2$ = H |
| 1453 | J = J-18a, R$^1$ = CH$_2$OMe, R$^2$ = H |
| 1454 | J = J-18a, R$^1$ = OMe, R$^2$ = H |
| 1455 | J = J-18a, R$^1$ = OEt, R$^2$ = H |
| 1456 | J = J-18a, R$^1$ = H, R$^2$ = Et |
| 1457 | J = J-18a, R$^1$ = H, R$^2$ = n-Pr |
| 1458 | J = J-18a, R$^1$ = H, R$^2$ = CH$_2$OMe |
| 1459 | J = J-18a, R$^1$ = H, R$^2$ = OMe |
| 1460 | J = J-18a, R$^1$ = H, R$^2$ = OEt |
| 1461 | J = J-20a, R$^1$ = Me, R$^2$ = H |
| 1462 | J = J-20a, R$^1$ = Et, R$^2$ = H |
| 1463 | J = J-20a, R$^1$ = n-Pr, R$^2$ = H |
| 1464 | J = J-20a, R$^1$ = CH$_2$OMe, R$^2$ = H |
| 1465 | J = J-20a, R$^1$ = OMe, R$^2$ = H |
| 1466 | J = J-20a, R$^1$ = OEt, R$^2$ = H |
| 1467 | J = J-20a, R$^1$ = H, R$^2$ = Et |
| 1468 | J = J-20a, R$^1$ = H, R$^2$ = n-Pr |
| 1469 | J = J-20a, R$^1$ = H, R$^2$ = CH$_2$OMe |
| 1470 | J = J-20a, R$^1$ = H, R$^2$ = OMe |
| 1471 | J = J-20a, R$^1$ = H, R$^2$ = OEt |
| 1472 | J = J-17a, R$^1$ = Me, R$^2$ = H |
| 1473 | J = J-17a, R$^1$ = Et, R$^2$ = H |
| 1474 | J = J-17a, R$^1$ = n-Pr, R$^2$ = H |
| 1475 | J = J-17a, R$^1$ = CR$_2$OMe, R$^2$ = H |

-continued

| Table | Row Heading |
|---|---|
| 1476 | J = J-17a, $R^1$ = OMe, $R^2$ = H |
| 1477 | J = J-17a, $R^1$ = OEt, $R^2$ = H |
| 1478 | J = J-17a, $R^1$ = H, $R^2$ = Et |
| 1479 | J = J-17a, $R^1$ = H, $R^2$ = n-Pr |
| 1480 | J = J-17a, $R^1$ = H, $R^2$ = $CH_2$OMe |
| 1481 | J = J-17a, $R^1$ = H, $R^2$ = OMe |
| 1482 | J = J-17a, $R^1$ = H, $R^2$ = OEt |
| 1483 | J = J-17b, $R^1$ = Me, $R^2$ = H |
| 1484 | J = J-17b, $R^1$ = Et, $R^2$ = H |
| 1485 | J = J-17b, $R^1$ = n-Pr, $R^2$ = H |
| 1486 | J = J-17b, $R^1$ = $CH_2$OMe, $R^2$ = H |
| 1487 | J = J-17b, $R^1$ = OMe, $R^2$ = H |
| 1488 | J = J-17b, $R^1$ = OEt, $R^2$ = H |
| 1489 | J = J-17b, $R^1$ = H, $R^2$ = Et |
| 1490 | J = J-17b, $R^1$ = H, $R^2$ = n-Pr |
| 1491 | J = J-17b, $R^1$ = H, $R^2$ = $CH_2$OMe |
| 1492 | J = J-17b, $R^1$ = H, $R^2$ = OMe |
| 1493 | J = J-17b, $R^1$ = H, $R^2$ = OEt |
| 1494 | J = J-22a, $R^1$ = Me, $R^2$ = H |
| 1495 | J = J-22a, $R^1$ = Et, $R^2$ = H |
| 1496 | J = J-22a, $R^1$ = n-Pr, $R^2$ = H |
| 1497 | J = J-22a, $R^1$ = $CH_2$OMe, $R^2$ = H |
| 1498 | J = J-22a, $R^1$ = OMe, $R^2$ = H |
| 1499 | J = J-22a, $R^1$ = OEt, $R^2$ = H |
| 1500 | J = J-22a, $R^1$ = H, $R^2$ = Et |
| 1501 | J = J-22a, $R^1$ = H, $R^2$ = n-Pr |
| 1502 | J = J-22a, $R^1$ = H, $R^2$ = $CH_2$OMe |
| 1503 | J = J-22a, $R^1$ = H, $R^2$ = OMe |
| 1504 | J = J-22a, $R^1$ = H, $R^2$ = OEt |

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-Propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 µm can be wet milled using media mills to obtain particles with average diameters below 3 µm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 µm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714.

Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food—Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook,* 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following non-limiting Examples are illustrative of the invention. Percentages are by weight except where otherwise indicated.

Example A

| High Strength Concentrate | |
|---|---|
| Compound 1 | 98.5% |
| silica aerogel | 0.5% |
| synthetic amorphous fine silica | 1.0% |

Example B

| Wettable Powder | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 1 | 10.0% |
| attapulgite granules (low volatile matter, 0.71/0.30 mm; U.S.S. No. 25-50 sieves) | 90.0% |

Example D

| Extruded Pellet | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 1 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Suspension Concentrate | |
|---|---|
| Compound 1 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example H

| Emulsion in Water | |
|---|---|
| Compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

| Oil Dispersion | |
|---|---|
| Compound 1 | 25% |
| polyoxyethylene sorbitol hexaoleate | 15% |
| organically modified bentonite clay | 2.5% |
| fatty acid methyl ester | 57.5% |

The present disclosure also includes Examples A through I above except the "Compound 1" is replaced with "Compound 2", "Compound 3", "Compound 4", "Compound 5", "Compound 6", "Compound 7", "Compound 8", "Compound 9", "Compound 10", "Compound 11", "Compound 12", "Compound 13", "Compound 14", "Compound 15", "Compound 16", "Compound 17", "Compound 18", "Compound 19", "Compound 20", "Compound 21", "Compound 22", "Compound 23", "Compound 24" or "Compound 25".

Test results indicate that the compounds of the present invention are highly active preemergent and/or postemergent herbicides and/or plant growth regulants. The compounds of the inention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), *sorghum*, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

In one common embodiment, a compound of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the invention can be directly applied to a plant or a part thereof, particularly of the undesired vegetation, and/or to the growth medium in contact with the plant.

Plant varieties and cultivars of the desired vegetation in the locus treated with a compound of the invention can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars in the locus which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Exhibit C. Additional information for the genetic modifications listed in Exhibit C can be obtained from publicly available databases maintained, for example, by the U.S. Department of Agriculture.

The following abbreviations, T1 through T37, are used in Exhibit C for traits. A "-" means the entry is not available, "tol." means tolerance, "mod." means modified, "herb." means herbicide, and "res." means resistance.

| Trait | Description |
|---|---|
| T1 | Glyphosate tol. |
| T2 | High lauric acid oil |
| T3 | Glufosinate tol. |
| T4 | Phytate breakdown |
| T5 | Oxynil tol. |
| T6 | Disease res. |
| T7 | Insect res. |
| T9 | Mod. flower color |
| T11 | ALS herb. tol. |
| T12 | Dicamba tol. |
| T13 | Anti-allergy |
| T14 | Salt tol. |
| T15 | Cold tol. |
| T16 | Imidazolinone herb. tol. |

| Trait | Description |
|---|---|
| T17 | Mod. alpha-amylase |
| T18 | Pollination control |
| T19 | 2,4-D tol. |
| T20 | Increased lysine |
| T21 | Drought tol. |
| T22 | Delayed ripening/senescence |
| T23 | Mod. product quality |
| T24 | High cellulose |
| T25 | Mod. starch/carbohydrate |
| T26 | Insect & disease res. |
| T27 | High tryptophan |
| T28 | Erect leaves semidwarf |
| T29 | Semidwarf |
| T30 | Low iron tol. |
| T31 | Mod. oil/fatty acid |
| T32 | HPPD tol. |
| T33 | High oil |
| T34 | Aryloxyalkanoate tol. |
| T35 | Mesotrione tol. |
| T36 | Reduced nicotine |
| T37 | Mod. product |

Exhibit C

| Crop | Event Name | Event Code | Trait(s) | Gene(s) |
|---|---|---|---|---|
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-883Ø2-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | ac1 (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |
| Cotton | COT102 | SYN-IR102-7 | T7 | vip3A(a) |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ae |
| Cotton | GHB614 | BCS-GH002-5 | T1 | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T1 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |

Exhibit C

| Crop | Event Name | Event Code | Trait(s) | Gene(s) |
|---|---|---|---|---|
| Cotton | Nqwe Chi 6 Bt | — | T7 | — |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |
| Maize | Bt10 | — | T3, T7 | cry1Ab; pat |
| Maize | Bt176 (176) | SYN-EV176-9 | T3, T7 | cry1Ab; bar |
| Maize | BVLA430101 | — | T4 | phyA2 |
| Maize | CBH-351 | ACS-ZM004-3 | T3, T7 | cry9C; bar |
| Maize | DAS40278-9 | DAS40278-9 | T19 | aad-1 |
| Maize | DBT418 | DKB-89614-9 | T3, T7 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | F1117 | — | T1 | mepsps |
| Maize | GAT-ZM1 | — | T3 | pat |
| Maize | LY038 | REN-00038-3 | T20 | cordapA |
| Maize | MIR162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |

Exhibit C

| Crop | Event Name | Event Code | Trait(s) | Gene(s) |
|---|---|---|---|---|
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13pNasNa800725atAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDS3 |
| Rice | gHvNAAT1 | — | T30 | HvNAAT-A; HvNAAT-B |
| Rice | gHvNAS1-1 | — | T30 | HvNAS1 |
| Rice | NIA-OS006-4 | — | T6 | WRKY45 |
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCr11 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DAS68416-4 | DAS68416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |
| Soybean | DAS21606 | DAS-21606 | T34, T3 | Modified aad-12; pat |
| Soybean | DAS44406 | DAS-44406-6 | T1, T3, T34 | Modified aad-12; 2mepsps; pat |
| Soybean | SYHT04R | SYN-0004R-8 | T35 | Modified avhppd |
| Soybean | 9582.814.19.1 | — | T3, T7 | cry1Ac, cry1F, PAT |
| Squash | CZW3 | SEM-ØCZW3-2 | T6 | cmv cp, zymv cp, wmv cp |
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |

Exhibit C

| Crop | Event Name | Event Code | Trait(s) | Gene(s) |
| --- | --- | --- | --- | --- |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |
| Wheat | MON71800 | MON-71800-3 | T1 | cp4 epsps (aroA:CP4) |

*Argentine (*Brassica napus*),
**Polish (*B. rapa*),
Eggplant

Although most typically, compounds of the invention are used to control undesired vegetation, contact of desired vegetation in the treated locus with compounds of the invention may result in super-additive or synergistic effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, topramezone, tralkoxydim, tri-allate, triafamone, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3(2H)-pyridazinone), 5-[[(2,6-difluorophenyl)methoxy]methyl]-4,5-dihydro-5-methyl-3-(3-methyl-2-thienyl)isoxazole (previously methioxolin), 3-[7-fluoro-3,4-dihydro-3-oxo-4-(2-propyn-1-yl)-2H-1,4-benzoxazin-6-yl]dihydro-1,5-dimethyl-6-thioxo-1,3,5-triazine-2,4(1H,3H)-dione, 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl) benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual, 13th Edition*, C. D. S. Tomlin, Ed., British Crop Protection Council, Farnham, Surrey, U. K., 2003 and *The BioPesticide Manual, 2nd Edition*, L. G. Copping, Ed., British Crop Protection Council, Farnham, Surrey, U. K., 2001.

For embodiments where one or more of these various mixing partners are used, active ingredients are often applied at an application rate between one-half and the full application rate specified on product labels for use of the active ingredient alone. The amounts are listed in references such as *The Pesticide Manual* and *The BioPesticide Manual*. The weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzene sulfonamide, N-(aminocarbonyl)-2-fluorobenzenesulfonamide, 1-bromo-4-[(chloromethyl)

sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide. Table A1 lists specific combinations of a Component (a) with Component (b) illustrative of the mixtures, compositions and methods of the present invention. Compound 1 in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 1 in Index Table A) with 2,4-D is typically applied in a weight ratio between 1:192-6:1. The remaining lines of Table A1 are to be construed similarly.

TABLE A1

| Component (a) (Compound #) | Component (b) | Typical Weight Ratio | More Typical Weight Ratio | Most Typical Weight Ratio |
|---|---|---|---|---|
| 1 | 2,4-D | 1:192-6:1 | 1:64-2:1 | 1:24-1:3 |
| 1 | Acetochlor | 1:768-2:1 | 1:256-1:2 | 1:96-1:11 |
| 1 | Acifluorfen | 1:96-12:1 | 1:32-4:1 | 1:12-1:2 |
| 1 | Aclonifen | 1:857-2:1 | 1:285-1:3 | 1:107-1:12 |
| 1 | Alachlor | 1:768-2:1 | 1:256-1:2 | 1:96-1:11 |
| 1 | Ametryn | 1:384-3:1 | 1:128-1:1 | 1:48-1:6 |
| 1 | Amicarbazone | 1:192-6:1 | 1:64-2:1 | 1:24-1:3 |
| 1 | Amidosulfuron | 1:6-168:1 | 1:2-56:1 | 1:1-11:1 |
| 1 | Aminocyclopyrachlor | 1:48-24:1 | 1:16-8:1 | 1:6-2:1 |
| 1 | Aminopyralid | 1:20-56:1 | 1:6-19:1 | 1:2-4:1 |
| 1 | Amitrole | 1:768-2:1 | 1:256-1:2 | 1:96-1:11 |
| 1 | Anilofos | 1:96-12:1 | 1:32-4:1 | 1:12-1:2 |
| 1 | Asulam | 1:960-2:1 | 1:320-1:3 | 1:120-1:14 |
| 1 | Atrazine | 1:192-6:1 | 1:64-2:1 | 1:24-1:3 |
| 1 | Azimsulfuron | 1:6-168:1 | 1:2-56:1 | 1:1-11:1 |
| 1 | Beflubutamid | 1:342-4:1 | 1:114-2:1 | 1:42-1:5 |
| 1 | Benfuresate | 1:617-2:1 | 1:205-1:2 | 1:77-1:9 |
| 1 | Bensulfuron-methyl | 1:25-45:1 | 1:8-15:1 | 1:3-3:1 |
| 1 | Bentazone | 1:192-6:1 | 1:64-2:1 | 1:24-1:3 |
| 1 | Benzobicyclon | 1:85-14:1 | 1:28-5:1 | 1:10-1:2 |
| 1 | Benzofenap | 1:257-5:1 | 1:85-2:1 | 1:32-1:4 |
| 1 | Bicyclopyrone | 1:42-27:1 | 1:14-9:1 | 1:5-2:1 |
| 1 | Bifenox | 1:257-5:1 | 1:85-2:1 | 1:32-1:4 |
| 1 | Bispyribac-sodium | 1:10-112:1 | 1:3-38:1 | 1:1-7:1 |
| 1 | Bromacil | 1:384-3:1 | 1:128-1:1 | 1:48-1:6 |
| 1 | Bromobutide | 1:384-3:1 | 1:128-1:1 | 1:48-1:6 |
| 1 | Bromoxynil | 1:96-12:1 | 1:32-4:1 | 1:12-1:2 |
| 1 | Butachlor | 1:768-2:1 | 1:256-1:2 | 1:96-1:11 |
| 1 | Butafenacil | 1:42-27:1 | 1:14-9:1 | 1:5-2:1 |
| 1 | Butylate | 1:1542-1:2 | 1:514-1:5 | 1:192-1:22 |
| 1 | Carfenstrole | 1:192-6:1 | 1:64-2:1 | 1:24-1:3 |
| 1 | Carfentrazone-ethyl | 1:128-9:1 | 1:42-3:1 | 1:16-1:2 |
| 1 | Chlorimuron-ethyl | 1:8-135:1 | 1:2-45:1 | 1:1-9:1 |
| 1 | Chlorotoluron | 1:768-2:1 | 1:256-1:2 | 1:96-1:11 |
| 1 | Chlorsulfuron | 1:6-168:1 | 1:2-56:1 | 1:1-11:1 |
| 1 | Cincosulfuron | 1:17-68:1 | 1:5-23:1 | 1:2-5:1 |
| 1 | Cinidon-ethyl | 1:384-3:1 | 1:128-1:1 | 1:48-1:6 |
| 1 | Cinmethylin | 1:34-34:1 | 1:11-12:1 | 1:4-3:1 |
| 1 | Clacyfos | 1:34-34:1 | 1:11-12:1 | 1:4-3:1 |
| 1 | Clethodim | 1:48-24:1 | 1:16-8:1 | 1:6-2:1 |
| 1 | Clodinafop-propargyl | 1:20-56:1 | 1:6-19:1 | 1:2-4:1 |
| 1 | Clomazone | 1:384-3:1 | 1:128-1:1 | 1:48-1:6 |
| 1 | Clomeprop | 1:171-7:1 | 1:57-3:1 | 1:21-1:3 |
| 1 | Clopyralid | 1:192-6:1 | 1:64-2:1 | 1:24-1:3 |
| 1 | Cloransulam-methyl | 1:12-96:1 | 1:4-32:1 | 1:1-6:1 |

TABLE A1-continued

| Component (a) (Compound #) | Component (b) | Typical Weight Ratio | More Typical Weight Ratio | Most Typical Weight Ratio |
|---|---|---|---|---|
| 1 | Cumyluron | 1:384-3:1 | 1:128-1:1 | 1:48-1:6 |
| 1 | Cyanazine | 1:384-3:1 | 1:128-1:1 | 1:48-1:6 |
| 1 | Cyclopyrimorate | 1:17-68:1 | 1:5-23:1 | 1:2-5:1 |
| 1 | Cyclosulfamuron | 1:17-68:1 | 1:5-23:1 | 1:2-5:1 |
| 1 | Cycloxydim | 1:96-12:1 | 1:32-4:1 | 1:12-1:2 |
| 1 | Cyhalofop | 1:25-45:1 | 1:8-15:1 | 1:3-3:1 |
| 1 | Daimuron | 1:192-6:1 | 1:64-2:1 | 1:24-1:3 |
| 1 | Desmedipham | 1:322-4:1 | 1:107-2:1 | 1:40-1:5 |
| 1 | Dicamba | 1:192-6:1 | 1:64-2:1 | 1:24-1:3 |
| 1 | Dichlobenil | 1:1371-1:2 | 1:457-1:4 | 1:171-1:20 |
| 1 | Dichlorprop | 1:925-2:1 | 1:308-1:3 | 1:115-1:13 |
| 1 | Diclofop-methyl | 1:384-3:1 | 1:128-1:1 | 1:48-1:6 |
| 1 | Diclosulam | 1:10-112:1 | 1:3-38:1 | 1:1-7:1 |
| 1 | Difenzoquat | 1:288-4:1 | 1:96-2:1 | 1:36-1:4 |
| 1 | Diflufenican | 1:857-2:1 | 1:285-1:3 | 1:107-1:12 |
| 1 | Diflufenzopyr | 1:12-96:1 | 1:4-32:1 | 1:1-6:1 |
| 1 | Dimethachlor | 1:768-2:1 | 1:256-1:2 | 1:96-1:11 |
| 1 | Dimethametryn | 1:192-6:1 | 1:64-2:1 | 1:24-1:3 |
| 1 | Dimethenamid-P | 1:384-3:1 | 1:128-1:1 | 1:48-1:6 |
| 1 | Dithiopyr | 1:192-6:1 | 1:64-2:1 | 1:24-1:3 |
| 1 | Diuron | 1:384-3:1 | 1:128-1:1 | 1:48-1:6 |
| 1 | EPTC | 1:768-2:1 | 1:256-1:2 | 1:96-1:11 |
| 1 | Esprocarb | 1:1371-1:2 | 1:457-1:4 | 1:171-1:20 |
| 1 | Ethalfluralin | 1:384-3:1 | 1:128-1:1 | 1:48-1:6 |
| 1 | Ethametsulfuron-methyl | 1:17-68:1 | 1:5-23:1 | 1:2-5:1 |
| 1 | Ethoxyfen | 1:8-135:1 | 1:2-45:1 | 1:1-9:1 |
| 1 | Ethoxysulfuron | 1:20-56:1 | 1:6-19:1 | 1:2-4:1 |
| 1 | Etobenzanid | 1:257-5:1 | 1:85-2:1 | 1:32-1:4 |
| 1 | Fenoxaprop-ethyl | 1:120-10:1 | 1:40-4:1 | 1:15-1:2 |
| 1 | Fenoxasulfone | 1:85-14:1 | 1:28-5:1 | 1:10-1:2 |
| 1 | Fenquinotrione | 1:17-68:1 | 1:5-23:1 | 1:2-5:1 |
| 1 | Fentrazamide | 1:17-68:1 | 1:5-23:1 | 1:2-5:1 |
| 1 | Flazasulfuron | 1:17-68:1 | 1:5-23:1 | 1:2-5:1 |
| 1 | Florasulam | 1:2-420:1 | 1:1-140:1 | 2:1-27:1 |
| 1 | Fluazifop-butyl | 1:192-6:1 | 1:64-2:1 | 1:24-1:3 |
| 1 | Flucarbazone | 1:8-135:1 | 1:2-45:1 | 1:1-9:1 |
| 1 | Flucetosulfuron | 1:8-135:1 | 1:2-45:1 | 1:1-9:1 |
| 1 | Flufenacet | 1:257-5:1 | 1:85-2:1 | 1:32-1:4 |
| 1 | Flumetsulam | 1:24-48:1 | 1:8-16:1 | 1:3-3:1 |
| 1 | Flumiclorac-pentyl | 1:10-112:1 | 1:3-38:1 | 1:1-7:1 |
| 1 | Flumioxazin | 1:25-45:1 | 1:8-15:1 | 1:3-3:1 |
| 1 | Fluometuron | 1:384-3:1 | 1:128-1:1 | 1:48-1:6 |
| 1 | Flupyrsulfuron-methyl | 1:3-336:1 | 1:1-112:1 | 2:1-21:1 |
| 1 | Fluridone | 1:384-3:1 | 1:128-1:1 | 1:48-1:6 |
| 1 | Fluroxypyr | 1:96-12:1 | 1:32-4:1 | 1:12-1:2 |
| 1 | Flurtamone | 1:857-2:1 | 1:285-1:3 | 1:107-1:12 |
| 1 | Fluthiacet-methyl | 1:48-42:1 | 1:16-14:1 | 1:3-3:1 |
| 1 | Fomesafen | 1:96-12:1 | 1:32-4:1 | 1:12-1:2 |
| 1 | Foramsulfuron | 1:13-84:1 | 1:4-28:1 | 1:1-6:1 |
| 1 | Glufosinate | 1:288-4:1 | 1:96-2:1 | 1:36-1:4 |
| 1 | Glyphosate | 1:288-4:1 | 1:96-2:1 | 1:36-1:4 |
| 1 | Halosulfuron-methyl | 1:17-68:1 | 1:5-23:1 | 1:2-5:1 |
| 1 | Halauxifen | 1:20-56:1 | 1:6-19:1 | 1:2-4:1 |
| 1 | Halauxifen methyl | 1:20-56:1 | 1:6-19:1 | 1:2-4:1 |
| 1 | Haloxyfop-methyl | 1:34-34:1 | 1:11-12:1 | 1:4-3:1 |
| 1 | Hexazinone | 1:192-6:1 | 1:64-2:1 | 1:24-1:3 |
| 1 | Imazamox | 1:13-84:1 | 1:4-28:1 | 1:1-6:1 |
| 1 | Imazapic | 1:20-56:1 | 1:6-19:1 | 1:2-4:1 |
| 1 | Imazapyr | 1:85-14:1 | 1:28-5:1 | 1:10-1:2 |
| 1 | Imazaquin | 1:34-34:1 | 1:11-12:1 | 1:4-3:1 |
| 1 | Imazethabenz-methyl | 1:171-7:1 | 1:57-3:1 | 1:21-1:3 |
| 1 | Imazethapyr | 1:24-48:1 | 1:8-16:1 | 1:3-3:1 |
| 1 | Imazosulfuron | 1:27-42:1 | 1:9-14:1 | 1:3-3:1 |
| 1 | Indanofan | 1:342-4:1 | 1:114-2:1 | 1:42-1:5 |
| 1 | Indaziflam | 1:25-45:1 | 1:8-15:1 | 1:3-3:1 |
| 1 | Iodosulfuron-methyl | 1:3-336:1 | 1:1-112:1 | 2:1-21:1 |
| 1 | Ioxynil | 1:192-6:1 | 1:64-2:1 | 1:24-1:3 |
| 1 | Ipfencarbazone | 1:85-14:1 | 1:28-5:1 | 1:10-1:2 |
| 1 | Isoproturon | 1:384-3:1 | 1:128-1:1 | 1:48-1:6 |
| 1 | Isoxaben | 1:288-4:1 | 1:96-2:1 | 1:36-1:4 |
| 1 | Isoxaflutole | 1:60-20:1 | 1:20-7:1 | 1:7-2:1 |
| 1 | Lactofen | 1:42-27:1 | 1:14-9:1 | 1:5-2:1 |
| 1 | Lenacil | 1:384-3:1 | 1:128-1:1 | 1:48-1:6 |
| 1 | Linuron | 1:384-3:1 | 1:128-1:1 | 1:48-1:6 |
| 1 | MCPA | 1:192-6:1 | 1:64-2:1 | 1:24-1:3 |
| 1 | MCPB | 1:288-4:1 | 1:96-2:1 | 1:36-1:4 |
| 1 | Mecoprop | 1:768-2:1 | 1:256-1:2 | 1:96-1:11 |

TABLE A1-continued

| Component (a) (Compound #) | Component (b) | Typical Weight Ratio | More Typical Weight Ratio | Most Typical Weight Ratio |
|---|---|---|---|---|
| 1 | Mefenacet | 1:384-3:1 | 1:128-1:1 | 1:48-1:6 |
| 1 | Mefluidide | 1:192-6:1 | 1:64-2:1 | 1:24-1:3 |
| 1 | Mesosulfuron-methyl | 1:5-224:1 | 1:1-75:1 | 1:1-14:1 |
| 1 | Mesotrione | 1:42-27:1 | 1:14-9:1 | 1:5-2:1 |
| 1 | Metamifop | 1:42-27:1 | 1:14-9:1 | 1:5-2:1 |
| 1 | Metazachlor | 1:384-3:1 | 1:128-1:1 | 1:48-1:6 |
| 1 | Metazosulfuron | 1:25-45:1 | 1:8-15:1 | 1:3-3:1 |
| 1 | Methabenzthiazuron | 1:768-2:1 | 1:256-1:2 | 1:96-1:11 |
| 1 | Metolachlor | 1:768-2:1 | 1:256-1:2 | 1:96-1:11 |
| 1 | Metosulam | 1:8-135:1 | 1:2-45:1 | 1:1-9:1 |
| 1 | Metribuzin | 1:192-6:1 | 1:64-2:1 | 1:24-1:3 |
| 1 | Metsulfuron-methyl | 1:2-560:1 | 1:1-187:1 | 3:1-35:1 |
| 1 | Molinate | 1:1028-2:1 | 1:342-1:3 | 1:128-1:15 |
| 1 | Napropamide | 1:384-3:1 | 1:128-1:1 | 1:48-1:6 |
| 1 | Napropamide-M | 1:192-6:1 | 1:64-2:1 | 1:24-1:3 |
| 1 | Naptalam | 1:192-6:1 | 1:64-2:1 | 1:24-1:3 |
| 1 | Nicosulfuron | 1:12-96:1 | 1:4-32:1 | 1:1-6:1 |
| 1 | Norflurazon | 1:1152-1:1 | 1:384-1:3 | 1:144-1:16 |
| 1 | Orbencarb | 1:1371-1:2 | 1:457-1:4 | 1:171-1:20 |
| 1 | Orthosulfamuron | 1:20-56:1 | 1:6-19:1 | 1:2-4:1 |
| 1 | Oryzalin | 1:514-3:1 | 1:171-1:2 | 1:64-1:8 |
| 1 | Oxadiargyl | 1:384-3:1 | 1:128-1:1 | 1:48-1:6 |
| 1 | Oxadiazon | 1:548-3:1 | 1:182-1:2 | 1:68-1:8 |
| 1 | Oxasulfuron | 1:27-42:1 | 1:9-14:1 | 1:3-3:1 |
| 1 | Oxaziclomefone | 1:42-27:1 | 1:14-9:1 | 1:5-2:1 |
| 1 | Oxyfluorfen | 1:384-3:1 | 1:128-1:1 | 1:48-1:6 |
| 1 | Paraquat | 1:192-6:1 | 1:64-2:1 | 1:24-1:3 |
| 1 | Pendimethalin | 1:384-3:1 | 1:128-1:1 | 1:48-1:6 |
| 1 | Penoxsulam | 1:10-112:1 | 1:3-38:1 | 1:1-7:1 |
| 1 | Penthoxamid | 1:384-3:1 | 1:128-1:1 | 1:48-1:6 |
| 1 | Pentoxazone | 1:102-12:1 | 1:34-4:1 | 1:12-1:2 |
| 1 | Phenmedipham | 1:102-12:1 | 1:34-4:1 | 1:12-1:2 |
| 1 | Picloram | 1:96-12:1 | 1:32-4:1 | 1:12-1:2 |
| 1 | Picolinafen | 1:34-34:1 | 1:11-12:1 | 1:4-3:1 |
| 1 | Pinoxaden | 1:25-45:1 | 1:8-15:1 | 1:3-3:1 |
| 1 | Pretilachlor | 1:192-6:1 | 1:64-2:1 | 1:24-1:3 |
| 1 | Primisulfuron-methyl | 1:8-135:1 | 1:2-45:1 | 1:1-9:1 |
| 1 | Prodiamine | 1:384-3:1 | 1:128-1:1 | 1:48-1:6 |
| 1 | Profoxydim | 1:42-27:1 | 1:14-9:1 | 1:5-2:1 |
| 1 | Prometryn | 1:384-3:1 | 1:128-1:1 | 1:48-1:6 |
| 1 | Propachlor | 1:1152-1:1 | 1:384-1:3 | 1:144-1:16 |
| 1 | Propanil | 1:384-3:1 | 1:128-1:1 | 1:48-1:6 |
| 1 | Propaquizafop | 1:48-24:1 | 1:16-8:1 | 1:6-2:1 |
| 1 | Propoxycarbazone | 1:17-68:1 | 1:5-23:1 | 1:2-5:1 |
| 1 | Propyrisulfuron | 1:17-68:1 | 1:5-23:1 | 1:2-5:1 |
| 1 | Propyzamide | 1:384-3:1 | 1:128-1:1 | 1:48-1:6 |
| 1 | Prosulfocarb | 1:1200-1:2 | 1:400-1:4 | 1:150-1:17 |
| 1 | Prosulfuron | 1:6-168:1 | 1:2-56:1 | 1:1-11:1 |
| 1 | Pyraclonil | 1:42-27:1 | 1:14-9:1 | 1:5-2:1 |
| 1 | Pyraflufen-ethyl | 1:5-224:1 | 1:1-75:1 | 1:1-14:1 |
| 1 | Pyrasulfotole | 1:13-84:1 | 1:4-28:1 | 1:1-6:1 |
| 1 | Pyrazolynate | 1:857-2:1 | 1:285-1:3 | 1:107-1:12 |
| 1 | Pyrazosulfuron-ethyl | 1:10-112:1 | 1:3-38:1 | 1:1-7:1 |
| 1 | Pyrazoxyfen | 1:5-224:1 | 1:1-75:1 | 1:1-14:1 |
| 1 | Pyribenzoxim | 1:10-112:1 | 1:3-38:1 | 1:1-7:1 |
| 1 | Pyributicarb | 1:384-3:1 | 1:128-1:1 | 1:48-1:6 |
| 1 | Pyridate | 1:288-4:1 | 1:96-2:1 | 1:36-1:4 |
| 1 | Pyriftalid | 1:10-112:1 | 1:3-38:1 | 1:1-7:1 |
| 1 | Pyriminobac-methyl | 1:20-56:1 | 1:6-19:1 | 1:2-4:1 |
| 1 | Pyrimisulfan | 1:17-68:1 | 1:5-23:1 | 1:2-5:1 |
| 1 | Pyrithiobac | 1:24-48:1 | 1:8-16:1 | 1:3-3:1 |
| 1 | Pyroxasulfone | 1:85-14:1 | 1:28-5:1 | 1:10-1:2 |
| 1 | Pyroxsulam | 1:5-224:1 | 1:1-75:1 | 1:1-14:1 |
| 1 | Quinclorac | 1:192-6:1 | 1:64-2:1 | 1:24-1:3 |
| 1 | Quizalofop-ethyl | 1:42-27:1 | 1:14-9:1 | 1:5-2:1 |
| 1 | Rimsulfuron | 1:13-84:1 | 1:4-28:1 | 1:1-6:1 |

TABLE A1-continued

| Component (a) (Compound #) | Component (b) | Typical Weight Ratio | More Typical Weight Ratio | Most Typical Weight Ratio |
|---|---|---|---|---|
| 1 | Saflufenacil | 1:25-45:1 | 1:8-15:1 | 1:3-3:1 |
| 1 | Sethoxydim | 1:96-12:1 | 1:32-4:1 | 1:12-1:2 |
| 1 | Simazine | 1:384-3:1 | 1:128-1:1 | 1:48-1:6 |
| 1 | Sulcotrione | 1:120-10:1 | 1:40-4:1 | 1:15-1:2 |
| 1 | Sulfentrazone | 1:147-8:1 | 1:49-3:1 | 1:18-1:3 |
| 1 | Sulfometuron-methyl | 1:34-34:1 | 1:11-12:1 | 1:4-3:1 |
| 1 | Sulfosulfuron | 1:8-135:1 | 1:2-45:1 | 1:1-9:1 |
| 1 | Tebuthiuron | 1:384-3:1 | 1:128-1:1 | 1:48-1:6 |
| 1 | Tefuryltrione | 1:42-27:1 | 1:14-9:1 | 1:5-2:1 |
| 1 | Tembotrione | 1:31-37:1 | 1:10-13:1 | 1:3-3:1 |
| 1 | Tepraloxydim | 1:25-45:1 | 1:8-15:1 | 1:3-3:1 |
| 1 | Terbacil | 1:288-4:1 | 1:96-2:1 | 1:36-1:4 |
| 1 | Terbuthylazine | 1:857-2:1 | 1:285-1:3 | 1:107-1:12 |
| 1 | Terbutryn | 1:192-6:1 | 1:64-2:1 | 1:24-1:3 |
| 1 | Thenylchlor | 1:85-14:1 | 1:28-5:1 | 1:10-1:2 |
| 1 | Thiazopyr | 1:384-3:1 | 1:128-1:1 | 1:48-1:6 |
| 1 | Thiencarbazone | 1:3-336:1 | 1:1-112:1 | 2:1-21:1 |
| 1 | Thifensulfuron-methyl | 1:5-224:1 | 1:1-75:1 | 1:1-14:1 |
| 1 | Tiafenacil | 1:17-68:1 | 1:5-23:1 | 1:2-5:1 |
| 1 | Thiobencarb | 1:768-2:1 | 1:256-1:2 | 1:96-1:11 |
| 1 | Topramzone | 1:6-168:1 | 1:2-56:1 | 1:1-11:1 |
| 1 | Tralkoxydim | 1:68-17:1 | 1:22-6:1 | 1:8-2:1 |
| 1 | Triallate | 1:768-2:1 | 1:256-1:2 | 1:96-1:11 |
| 1 | Triasulfuron | 1:5-224:1 | 1:1-75:1 | 1:1-14:1 |
| 1 | Triaziflam | 1:171-7:1 | 1:57-3:1 | 1:21-1:3 |
| 1 | Tribenuron-methyl | 1:3-336:1 | 1:1-112:1 | 2:1-21:1 |
| 1 | Triclopyr | 1:192-6:1 | 1:64-2:1 | 1:24-1:3 |
| 1 | Trifloxysulfuron | 1:2-420:1 | 1:1-140:1 | 2:1-27:1 |
| 1 | Trifluralin | 1:288-4:1 | 1:96-2:1 | 1:36-1:4 |
| 1 | Triflusulfuron-methyl | 1:17-68:1 | 1:5-23:1 | 1:2-5:1 |
| 1 | Tritosulfuron | 1:13-84:1 | 1:4-28:1 | 1:1-6:1 |

Table A2 is constructed the same as Table A1 above except that entries below the "Component (a)" column heading are replaced with the respective Component (a) Column Entry shown below. Compound 1 in the Component (a) column is identified in Index Table A. Thus, for example, in Table A2 the entries below the "Component (a)" column heading all recite "Compound 1" (i.e. Compound 1 identified in Index Table A), and the first line below the column headings in Table A2 specifically discloses a mixture of Compound 2 with 2,4-D. Tables A3 through A25 are constructed similarly.

| Table Number | Component (a) Column Entries |
|---|---|
| A2 | Compound 2 |
| A3 | Compound 6 |
| A4 | Compound 14 |
| A5 | Compound 16 |
| A6 | Compound 17 |
| A7 | Compound 23 |
| A8 | Compound 25 |
| A9 | Compound 3 |
| A10 | Compound 4 |
| A11 | Compound 5 |
| A12 | Compound 7 |
| A13 | Compound 8 |
| A14 | Compound 9 |
| A15 | Compound 10 |
| A16 | Compound 11 |
| A17 | Compound 12 |
| A18 | Compound 13 |
| A19 | Compound 15 |
| A20 | Compound 18 |
| A21 | Compound 19 |
| A22 | Compound 20 |

-continued

| Table Number | Component (a) Column Entries |
|---|---|
| A23 | Compound 21 |
| A24 | Compound 22 |
| A25 | Compound 24 |

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide selected from the group consisting of aminocyclopyrachlor, chlorimuron-ethyl, nicosulfuron, mesotrione, thifensulfuron-methyl, flupyrsulfuron-methyl, tribenuron, pyroxasulfone, pinoxaden, tembotrione, pyroxsulam, metolachlor and S-metolachlor.

The following Tests demonstrate the control efficacy of the compounds of this invention against specific weeds. The weed control afforded by the compounds is not limited, however, to these species. See Index Tables A for compound descriptions. The following abbreviations are used in the Index Table which follows: Ph is phenyl and OMe is methoxy. The abbreviation "Ex." stands for "Example" and is followed by a number indicating in which example the compound is prepared. The abbreviation "Cmpd. No." means Compound Number. Mass spectra are reported as the molecular weight of the highest isotopic abundance using atmospheric pressure chemical ionization (AP$^+$) unless otherwise noted.

INDEX TABLE A

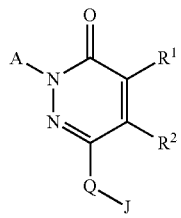

| Cmpd. No. | R¹ | R² | Q | J | A | MS |
|---|---|---|---|---|---|---|
| 1 (Ex. 3) | H | CH₃ | CH₂ | 2-CF₃-4-pyridyl | 4-F-phenyl | ** |
| 2 | H | CH₃ | CH₂ | 2-CF₃-4-pyridyl | 4-CF₃-phenyl | 412.4ᵃ |
| 3 (Ex. 4) | H | CH₃ | CH₂ | 3-CF₃-1H-pyrazol-1-yl | 4-F-phenyl | ** |
| 4 | H | CH₃ | O | 2-CF₃-4-pyridyl | 3-CF₃-phenyl | * |
| 5 (Ex. 5) | H | CH₃ | O | 2-CF₃-4-pyridyl | 4-CF₃-phenyl | ** |
| 6 (Ex. 5) | CH₃ | H | O | 2-CF₃-4-pyridyl | 4-CF₃-phenyl | ** |
| 7 | —CH₂CH₂CH₂CH₂— | | O | 2-CF₃-4-pyridyl | 4-Cl-phenyl | * |
| 8 | H | CH₃ | CH₂ | 3-CF₃-phenyl | 4-F-phenyl | 363 |
| 9 | CH₃ | H | O | 4-CF₃-2-pyridyl | 4-F-phenyl | * |
| 10 | H | CH₃ | O | 4-CF₃-2-pyridyl | 4-F-phenyl | * |
| 11 | CH₃ | H | O | 6-CF₃-2-pyridyl | 4-F-phenyl | * |
| 12 | H | CH₃ | O | 6-CF₃-2-pyridyl | 4-F-phenyl | * |
| 13 | CH₃ | H | O | 2-CF₃-4-pyridyl | 4-F-phenyl | * |
| 14 | H | CH₃ | O | 2-CF₃-4-pyridyl | 4-F-phenyl | * |
| 15 | H | CH₃ | O | 2-CF₃-4-pyridyl | Phenyl | * |
| 16 | H | OCH₃ | CH₂ | 2-CF₃-4-pyridyl | 4-CF₃-phenyl | 430.5 |
| 17 | H | OCH₃ | CH₂ | 2-CF₃-4-pyridyl | 4-F-phenyl | 378.5ᵃ |
| 18 | H | OCH₂CH₃ | CH₂ | 2-CF₃-4-pyridyl | 4-CF₃-phenyl | 444.5 |
| 19 | H | OCH₂CH₂CH₃ | CH₂ | 2-CF₃-4-pyridyl | 4-CF₃-phenyl | 458.6 |
| 20 | H | N(CH₃)₂ | CH₂ | 2-CF₃-4-pyridyl | 4-F-phenyl | 393.4 |
| 21 | H | N(CH₃)₂ | CH₂ | 2-CF₃-4-pyridyl | 4-CF₃-phenyl | 443.5 |
| 22 (Ex. 1) | H | OCH₂CH₃ | C=O | 2-CF₃-4-pyridyl | 4-F-phenyl | ** |
| 23 (Ex. 2) | H | OCH₂CH₃ | CH(OH) | 2-CF₃-4-pyridyl | 4-F-phenyl | ** |
| 24 | H | CH₂CH₂CH₃ | CH₂ | 2-CF₃-4-pyridyl | 4-F-phenyl | 392.1 |
| 25 | H | OCH₂CH₃ | CH₂ | 2-CF₃-4-pyridyl | 4-F-phenyl | 394.5 |

\* See Index Table B for ¹H NMR data.
\*\* See Synthesis Example for ¹H NMR data.
ᵃES⁻.

INDEX TABLE B

| Cmpd. No. | ¹H NMR Data (CDCl₃ solution unless indicated otherwise)ᵃ |
|---|---|
| 4 | δ 8.74 (m, 1H), 7.86 (m, 1H), 7.82 (m, 1H), 7.63 (m, 1H), 7.58 (m, 2H), 7.36 (m, 1H), 7.01 (m, 1H), 2.34 (s, 3H). |
| 7 | δ 8.80 (m, 1H), 7.57 (m, 1H), 7.53 (m, 2H), 7.37 (m, 2H), 7.38 (m, 1H), 7.33 (m, 1H). |
| 9 | δ 8.37 (m, 1H), 7.63 (m, 2H), 7.33 (m, 1H), 7.29 (m, 1H), 7.11 (m, 3H), 2.31 (s, 3H). |
| 10 | δ 8.37 (m, 1H), 7.59 (m, 2H), 7.33 (m, 2H), 7.11 (m, 2H), 6.96 (m, 1H), 2.18 (s, 3H). |
| 11 | δ 7.92 (m, 1H), 7.61 (m, 2H), 7.49 (m, 1H), 7.26 (m, 1H), 7.15 (m, 1H), 7.10 (m, 2H), 2.32 (s, 3H). |
| 12 | δ 7.95 (m, 1H), 7.58 (m, 2H), 7.50 (m, 1H), 7.27 (m, 1H), 7.08 (m, 2H), 6.96 (m, 1H), 2.21 (s, 3H). |
| 13 | δ 8.70 (m, 1H), 7.56 (m, 3H), 7.35 (m, 1H), 7.13 (m, 3H), 2.35 (s, 3H). |
| 14 | δ 8.71 (m, 1H), 7.60 (s, 1H), 7.53 (m, 2H), 7.33 (m, 1H), 7.09 (m, 2H), 6.99 (m, 1H), 2.32 (s, 3H). |
| 15 | δ 8.71 (m, 1H), 7.60 (s, 1H), 7.55 (m, 2H), 7.42 (m, 2H), 7.40 (m, 2H), 6.99 (m, 1H), 2.32 (s, 3H). |

ᵃ¹H NMR data are in ppm downfield from tetramethylsilane. Couplings are designated by (s)-singlet and (m)-multiplet.

Biological Examples of the Invention

Test A

Seeds of plant species selected from barnyardgrass (*Echinochloa crus-galli*), crabgrass, Large (large crabgrass, *Digitaria sanguinalis*), foxtail, giant (giant foxtail, *Setaria faberii*), morningglory (*Ipomoea* spp.), pigweed (*Amaranthus retroflexus*), velvetleaf (*Abutilon theophrasti*), wheat (*Triticum aestivum*), and corn (*Zea mays*) were planted into a blend of loam soil and sand and treated preemergence with a directed soil spray using test chemicals formulated in a non-phytotoxic solvent mixture which included a surfactant. At the same time these species were also treated with postemergence applications of test chemicals formulated in the same manner.

Plants ranged in height from 2 to 10 cm and were in the one- to two-leaf stage for the postemergence treatment. Treated plants and untreated controls were maintained in a greenhouse for approximately 10 d, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| Compounds | | | | | | | | | | | | | | |
|---|---|---|---|---|---|---|---|---|---|---|---|---|---|---|
| 500 g ai/ha Postemergence | 1 | 2 | 3 | 4 | 5 | 6 | 7 | 8 | 9 | 10 | 11 | 12 | 13 | 14 |
| Barnyardgrass | 100 | 90 | 10 | 20 | 70 | 90 | 10 | 50 | 0 | 0 | 0 | 70 | 60 | 90 |
| Corn | 90 | 90 | 20 | 30 | 30 | 50 | 10 | 40 | 0 | 10 | 0 | 50 | 50 | 70 |
| Crabgrass, Large | 100 | 100 | 30 | 60 | 80 | 90 | 10 | 90 | 0 | 20 | 20 | 70 | 90 | 90 |
| Foxtail, Giant | 100 | 100 | 30 | 70 | 90 | 100 | 10 | 90 | 0 | 10 | 20 | 80 | 90 | 90 |
| Morningglory | — | — | 70 | 70 | 100 | 100 | 20 | 80 | 0 | 30 | 30 | 90 | 60 | 100 |
| Pigweed | 100 | 100 | 70 | 100 | 100 | 100 | 100 | 100 | 0 | 60 | 70 | 90 | 100 | 100 |
| Velvetleaf | 100 | 100 | 80 | 100 | 100 | 100 | 40 | 80 | 0 | 10 | 0 | 60 | 70 | 90 |
| Wheat | 90 | 80 | 0 | 20 | 40 | 50 | 10 | 20 | 0 | 0 | 0 | 20 | 20 | 70 |

| 500 g ai/ha Postemergence | 15 | 16 | 17 | 18 | 19 | 20 | 21 | 22 | 23 | 24 | 25 |
|---|---|---|---|---|---|---|---|---|---|---|---|
| Barnyardgrass | 90 | 90 | 90 | 40 | 20 | 90 | 50 | 100 | 100 | 90 | 90 |
| Corn | 80 | 80 | 80 | 40 | 10 | 60 | 40 | 90 | 90 | 60 | 80 |
| Crabgrass, Large | 90 | 100 | 90 | 80 | 20 | 90 | 60 | 100 | 100 | 90 | 90 |
| Foxtail, Giant | 90 | 90 | 90 | 50 | 20 | 80 | 50 | 100 | 90 | 80 | 90 |
| Morningglory | 100 | 100 | 100 | 70 | 30 | 100 | 60 | 100 | 60 | 90 | 90 |
| Pigweed | 100 | 100 | 100 | 100 | 80 | 100 | 90 | 100 | 100 | 100 | 100 |
| Velvetleaf | 90 | 100 | 100 | 80 | 50 | 70 | 80 | 50 | 70 | 80 | 100 |
| Wheat | 60 | 70 | 70 | 20 | 10 | 50 | 30 | 90 | 90 | 70 | 70 |

| 125 g ai/ha Postemergence | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Barnyardgrass | 100 | 80 | 0 | 10 | 20 | 50 | 0 | 20 | 0 | 0 | 0 | 40 | 10 | 80 |
| Corn | 90 | 70 | 0 | 10 | 20 | 40 | 10 | 20 | 0 | 0 | 0 | 10 | 20 | 50 |
| Crabgrass, Large | 90 | 80 | 10 | 30 | 50 | 80 | 10 | 40 | 0 | 10 | 10 | 20 | 50 | 90 |
| Foxtail, Giant | 90 | 80 | 10 | 30 | 60 | 80 | 10 | 50 | 0 | 0 | 10 | 20 | 50 | 90 |
| Morningglory | — | — | 60 | 40 | 60 | 80 | 10 | 80 | 0 | 30 | 20 | 50 | 50 | 90 |
| Pigweed | 100 | 90 | 60 | 100 | 100 | 100 | 90 | 90 | 0 | 30 | 60 | 60 | 90 | 100 |
| Velvetleaf | 40 | 50 | 30 | 90 | 70 | 100 | 20 | 20 | 0 | 0 | 0 | 40 | 60 | 80 |
| Wheat | 60 | 40 | 0 | 10 | 30 | 40 | 0 | 10 | 0 | 0 | 0 | 0 | 0 | 40 |

| 125 g ai/ha Postemergence | 15 | 16 | 17 | 18 | 19 | 20 | 21 | 22 | 23 | 24 | 25 |
|---|---|---|---|---|---|---|---|---|---|---|---|
| Barnyardgrass | 70 | 80 | 80 | 30 | 10 | 50 | 40 | 20 | 20 | 70 | 80 |
| Corn | 40 | 20 | 60 | 20 | 10 | 30 | 20 | 50 | 50 | 50 | 70 |
| Crabgrass, Large | 80 | 90 | 90 | 60 | 10 | 50 | 20 | 60 | 60 | 70 | 80 |
| Foxtail, Giant | 70 | 90 | 90 | 20 | 10 | 40 | 30 | 60 | 50 | 70 | 70 |
| Morningglory | 100 | 90 | 100 | 30 | 10 | 50 | 30 | 40 | 20 | 50 | 40 |
| Pigweed | 100 | 100 | 100 | 90 | 80 | 90 | 90 | 100 | 100 | 100 | 100 |
| Velvetleaf | 70 | 80 | 100 | 30 | 10 | 60 | 60 | 20 | 20 | 80 | 60 |
| Wheat | 20 | 60 | 60 | 10 | 0 | 0 | 20 | 60 | 80 | 50 | 60 |

| 500 g ai/ha Preemergence | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Barnyardgrass | 100 | 100 | 20 | 40 | 90 | 80 | 40 | 80 | — | — | — | — | 60 | 100 |
| Corn | 90 | 50 | 0 | 10 | 10 | 20 | 0 | 0 | 0 | 0 | 0 | 30 | 10 | 50 |
| Crabgrass, Large | 100 | 100 | 90 | 100 | 100 | 100 | 40 | 100 | 0 | 10 | 10 | 100 | 100 | 90 |
| Foxtail, Giant | 100 | 100 | 40 | 100 | 100 | 100 | 30 | 90 | 0 | 20 | 0 | 100 | 100 | 90 |
| Morningglory | — | — | 0 | 40 | 80 | 90 | 0 | 0 | 0 | 0 | 0 | 50 | 80 | 100 |
| Pigweed | 100 | 100 | 80 | 100 | 100 | 100 | 50 | 100 | 0 | 30 | 0 | 100 | 90 | 100 |
| Velvetleaf | 90 | 50 | 20 | 20 | 100 | 80 | 0 | 0 | 0 | 0 | 0 | 70 | 50 | 100 |
| Wheat | 90 | 40 | 0 | 10 | 10 | 30 | 0 | 0 | 0 | 0 | 0 | 0 | 10 | 60 |

| 500 g ai/ha Preemergence | 15 | 16 | 17 | 18 | 19 | 20 | 21 | 22 | 23 | 24 | 25 |
|---|---|---|---|---|---|---|---|---|---|---|---|
| Barnyardgrass | 100 | 100 | 100 | 90 | 10 | 90 | 30 | 80 | 100 | 100 | 100 |
| Corn | 20 | 70 | 50 | 10 | 0 | 10 | 0 | 20 | 20 | 50 | 50 |
| Crabgrass, Large | 100 | 100 | 100 | 100 | 90 | 100 | 100 | 100 | 100 | 100 | 100 |
| Foxtail, Giant | 100 | 100 | 100 | 100 | 70 | 100 | 70 | 100 | 100 | 100 | 100 |
| Morningglory | 100 | 80 | — | 30 | 10 | 60 | 10 | 100 | 100 | 80 | 90 |
| Pigweed | 100 | 100 | 100 | 100 | 70 | 100 | 100 | 100 | 100 | 100 | 100 |
| Velvetleaf | 70 | 80 | 100 | 40 | 10 | 50 | 20 | 100 | 100 | 80 | 100 |
| Wheat | 20 | 70 | 50 | 20 | 0 | 30 | 10 | 40 | 90 | 50 | 60 |

| 125 g ai/ha Preemergence | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Barnyardgrass | 100 | 80 | 0 | 10 | 40 | 40 | 0 | 20 | — | — | — | — | 0 | 70 |
| Corn | 0 | 30 | 0 | 0 | 0 | 10 | 0 | 0 | 0 | 0 | 0 | 0 | 0 | 0 |
| Crabgrass, Large | 100 | 100 | 30 | 90 | 100 | 100 | 0 | 90 | 0 | 0 | 0 | 100 | 100 | 90 |

TABLE A-continued

| Compounds | | | | | | | | | | | | | | |
|---|---|---|---|---|---|---|---|---|---|---|---|---|---|---|
| Foxtail, Giant | 100 | 100 | 0 | 70 | 90 | 100 | 0 | 80 | 0 | 0 | 0 | 80 | 80 | 90 |
| Morningglory | — | — | 0 | 20 | 60 | 80 | 0 | 0 | 0 | 0 | 0 | 0 | 20 | 80 |
| Pigweed | 100 | 100 | 20 | 100 | 100 | 100 | 20 | 90 | 0 | 0 | 0 | 90 | 80 | 100 |
| Velvetleaf | 0 | 20 | 0 | 10 | 20 | 70 | 0 | 0 | 0 | 0 | 0 | 30 | 10 | 30 |
| Wheat | 0 | 0 | 0 | 0 | 0 | 10 | 0 | 0 | 0 | 0 | 0 | 0 | 0 | 10 |

| 125 g ai/ha Preemergence | 15 | 16 | 17 | 18 | 19 | 20 | 21 | 22 | 23 | 24 | 25 |
|---|---|---|---|---|---|---|---|---|---|---|---|
| Barnyardgrass | 50 | 90 | 80 | 60 | 0 | 20 | 10 | 20 | 20 | 70 | 90 |
| Corn | 10 | 40 | 40 | 10 | 0 | 0 | 0 | 0 | 0 | 30 | 50 |
| Crabgrass, Large | 100 | 100 | 100 | 100 | 70 | 100 | 80 | 100 | 100 | 100 | 100 |
| Foxtail, Giant | 100 | 100 | 100 | 100 | 40 | 80 | 30 | 90 | 100 | 100 | 100 |
| Morningglory | 90 | 80 | — | 30 | 0 | 10 | 0 | 30 | 100 | 30 | 30 |
| Pigweed | 100 | 100 | 100 | 100 | 60 | 100 | 100 | 100 | 100 | 100 | 100 |
| Velvetleaf | 30 | 30 | 100 | 40 | 0 | 20 | 0 | 40 | 80 | 30 | 40 |
| Wheat | 0 | 20 | 20 | 0 | 0 | 0 | 0 | 10 | 0 | 30 | 30 |

Test B

Plant species in the flooded paddy test selected from rice (*Oryza sativa*), small-flower sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 d, after which time all species were compared to controls and visually evaluated. Plant response ratings, summarized in Table B, are based on a scale of 0 to 100 where 0 is no effect and 100 is complete control. A dash (-) response means no test result.

TABLE B

| Compounds | | | | | | | | | | | |
|---|---|---|---|---|---|---|---|---|---|---|---|
| 250 g ai/ha Flood | 3 | 8 | 9 | 10 | 11 | 12 | 13 | 14 | 15 | 22 | 23 |
| Barnyardgrass | 0 | 20 | 0 | 0 | 0 | 20 | 0 | 40 | 0 | 10 | 10 |
| Ducksalad | 0 | 0 | 0 | 0 | 0 | 0 | 30 | 75 | 70 | 70 | 80 |
| Rice | 0 | 25 | 0 | 0 | 0 | 20 | 0 | 30 | 0 | 10 | 10 |
| Sedge, Umbrella | 0 | 75 | 0 | 0 | 0 | 0 | 65 | 75 | 70 | 80 | 70 |

| 125 g ai/ha Flood | 1 | 2 | 4 | 5 | 6 | 7 | 16 | 17 | 18 | 19 | 20 | 21 | 24 | 25 |
|---|---|---|---|---|---|---|---|---|---|---|---|---|---|---|
| Barnyardgrass | 10 | 0 | 20 | 55 | 0 | 0 | 45 | 90 | 0 | 0 | 0 | 0 | 0 | 0 |
| Ducksalad | 60 | 10 | 65 | 75 | 0 | 0 | 20 | 90 | 0 | 0 | 0 | 30 | 0 | 0 |
| Rice | 20 | 0 | 40 | 55 | 0 | 0 | 35 | 70 | 0 | 0 | 0 | 20 | 0 | 0 |
| Sedge, Umbrella | 80 | 80 | 70 | 80 | 0 | 0 | 80 | 90 | 75 | 0 | 0 | 90 | 90 | 75 |

Test C

Seeds of plant species selected from blackgrass (*Alopecurus myosuroides*), bromegrass, downy (downy bromegrass, *Bromus tectorum*), foxtail, green (green foxtail, *Setaria viridis*), ryegrass, Italian (Italian ryegrass, *Lolium multiflorum*), wheat (winter wheat, *Triticum aestivum*), oat, wild (wild oat, *Avena fatua*), galium (catchweed bedstraw, *Galium aparine*), bermudagrass (*Cynodon dactylon*), surinam grass (*Brachiaria decumbens*), cocklebur (common cocklebur, *Xanthium strumarium*), corn (*Zea mays*), crabgrass, large (large crabgrass, *Digitaria sanguinalis*), cupgrass, woolly (woolly cupgrass, *Eriochloa villosa*), foxtail, giant (giant foxtail, *Setaria faberii*), goosegrass (*Eleusine indica*), johnsongrass (*Sorghum halepense*), kochia (*Kochia scoparia*), lambsquarters (*Chenopodium album*), morningglory (*Ipomoea coccinea*), nightshade (eastern black nightshade, *Solanum ptycanthum*), nutsedge, yellow (yellow nutsedge, *Cyperus esculentus*), pigweed (*Amaranthus retroflexus*), ragweed (common ragweed, *Ambrosia elatior*), soybean (*Glycine max*), sunflower (common oilseed sunflower, *Helianthus annuus*), Russian thistle (*Salsola kali*), barnyardgrass (*Echinochloa crus-galli*), oilseed rape (*Brassica napus*), waterhemp (common waterhemp, *Amaranthus rudis*), and velvetleaf (*Abutilon theophrasti*) were planted into a blend of loam soil and sand and treated preemergence with test chemicals formulated in a non-phytotoxic solvent mixture which included a surfactant.

At the same time, plants selected from these crop and weed species and also barley (winter barley, *Hordeum vulgare*), canarygrass (*Phalaris minor*), windgrass (*Apera spica-venti*), deadnettle (henbit deadnettle, *Lamium amplexicaule*), and chickweed (common chickweed, *Stellaria media*) were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of test chemicals formulated in the same manner. Plants ranged in height from 2 to 18 cm (1- to 4-leaf stage) for postemergence treatments. Treated plants and controls were maintained in a greenhouse for 13 to 15 d, after which time all species were compared to controls and visually evaluated. Plant response ratings, summarized in Table C, are based on a scale of 0 to 100 where 0 is no effect and 100 is complete control. A dash (-) response means no test result.

TABLE C

| 250 g ai/ha | Compounds | | | | | |
|---|---|---|---|---|---|---|
| Postemergence | 1 | 2 | 6 | 14 | 16 | 17 |
| Barley | — | — | — | 25 | — | — |
| Barnyardgrass | 10 | 25 | 65 | — | 35 | 35 |
| Bermudagrass | — | — | — | 15 | — | — |
| Blackgrass | 5 | 15 | 50 | 45 | 10 | 5 |
| Bromegrass, Downy | — | — | — | 30 | — | — |
| Canarygrass | — | — | — | 15 | — | — |
| Chickweed | 90 | 90 | 98 | 55 | 98 | 95 |
| Cocklebur | — | — | — | 85 | — | — |
| Corn | 10 | 20 | 35 | 40 | 55 | 15 |
| Crabgrass, Large | 20 | 35 | 35 | 30 | 35 | 40 |
| Cupgrass, Woolly | — | — | — | 20 | — | — |
| Deadnettle | — | — | — | 85 | — | — |
| Foxtail, Giant | 20 | 25 | 85 | 15 | 55 | 45 |
| Foxtail, Green | — | — | — | 98 | — | — |
| Galium | 70 | 85 | 90 | 75 | 90 | 85 |
| Goosegrass | — | — | — | 15 | — | — |
| Johnsongrass | 5 | 10 | 40 | 30 | 35 | 65 |
| Kochia | 85 | 90 | 95 | 80 | 90 | 90 |
| Lambsquarters | 75 | 80 | 95 | 45 | 95 | 90 |
| Morningglory | 70 | 15 | — | 98 | 98 | 70 |
| Nutsedge, Yellow | 5 | 10 | 15 | 10 | 20 | 10 |
| Oat, Wild | 5 | 5 | 50 | 30 | 60 | 45 |
| Oilseed Rape | 30 | 50 | 95 | — | — | — |
| Pigweed | 85 | 60 | 95 | 85 | 95 | 70 |
| Ragweed | 60 | — | 80 | 70 | 60 | 85 |
| Ryegrass, Italian | 5 | 5 | 35 | 25 | 35 | 5 |
| Soybean | 70 | 40 | 65 | 95 | 65 | 90 |
| Surinam Grass | — | — | — | 45 | — | — |
| Velvetleaf | 30 | 35 | 95 | — | 75 | 45 |
| Waterhemp | 65 | 80 | 98 | — | 98 | 85 |
| Wheat | 5 | 5 | 25 | 5 | 10 | 10 |
| Windgrass | — | — | — | 30 | — | — |

| 125 g ai/ha | Compounds | | | | | |
|---|---|---|---|---|---|---|
| Postemergence | 1 | 2 | 6 | 14 | 16 | 17 |
| Barley | — | — | — | 10 | — | — |
| Barnyardgrass | 10 | 10 | 35 | — | 25 | 10 |
| Bermudagrass | — | — | — | 10 | — | — |
| Blackgrass | 5 | 10 | 35 | 5 | 5 | 5 |
| Bromegrass, Downy | — | — | — | 5 | — | — |
| Canarygrass | — | — | — | 10 | — | — |
| Chickweed | 60 | 90 | 95 | 35 | 90 | 85 |
| Cocklebur | — | — | — | 40 | — | — |
| Corn | 5 | 20 | 25 | 40 | 40 | 15 |
| Crabgrass, Large | 10 | 15 | 30 | 15 | 30 | 15 |
| Cupgrass, Woolly | — | — | — | 15 | — | — |
| Deadnettle | — | — | — | 85 | — | — |
| Foxtail, Giant | 15 | 25 | 65 | 10 | 30 | 20 |
| Foxtail, Green | — | — | — | 40 | — | — |
| Galium | 70 | 80 | 90 | 55 | 90 | 75 |
| Goosegrass | — | — | — | 15 | — | — |
| Johnsongrass | 5 | 10 | 20 | 25 | 20 | 5 |
| Kochia | 85 | 90 | 90 | 55 | 90 | 90 |
| Lambsquarters | 65 | 75 | 95 | 45 | 95 | 90 |
| Morningglory | 70 | 15 | — | 80 | 98 | 65 |
| Nutsedge, Yellow | 5 | 5 | 5 | 5 | 5 | 10 |
| Oat, Wild | 5 | 5 | 25 | 30 | 40 | 40 |
| Oilseed Rape | 10 | 45 | 95 | — | 80 | 25 |
| Pigweed | 65 | 60 | 95 | 80 | 95 | 60 |
| Ragweed | 50 | 60 | 80 | 60 | 60 | 80 |
| Ryegrass, Italian | 5 | 5 | 15 | 10 | 15 | 5 |
| Soybean | 50 | 40 | 50 | 95 | 55 | 90 |
| Surinam Grass | — | — | — | 30 | — | — |
| Velvetleaf | 20 | 30 | 55 | 50 | 60 | 30 |
| Waterhemp | 65 | 75 | 98 | — | 95 | 85 |
| Wheat | 5 | 5 | 15 | 5 | 10 | 5 |
| Windgrass | — | — | — | 25 | — | — |

TABLE C-continued

| 62 g ai/ha | Compounds | | | | | |
|---|---|---|---|---|---|---|
| Postemergence | 1 | 2 | 6 | 14 | 16 | 17 |
| Barley | — | — | — | 5 | — | — |
| Barnyardgrass | 10 | 10 | 10 | — | 10 | 5 |
| Bermudagrass | — | — | — | 10 | — | — |
| Blackgrass | 5 | 5 | 35 | 5 | 5 | 5 |
| Bromegrass, Downy | — | — | — | 5 | — | — |
| Canarygrass | — | — | — | 5 | — | — |
| Chickweed | 45 | 70 | 95 | 35 | 90 | 85 |
| Cocklebur | — | — | — | 40 | — | — |
| Corn | 5 | 20 | 25 | 35 | 40 | 15 |
| Crabgrass, Large | 5 | 5 | 20 | 10 | 25 | 10 |
| Cupgrass, Woolly | — | — | — | 15 | — | — |
| Deadnettle | — | — | — | 85 | — | — |
| Foxtail, Giant | 10 | 10 | 35 | 10 | 15 | 10 |
| Foxtail, Green | — | — | — | 10 | — | — |
| Galium | 65 | 80 | 90 | 55 | 80 | 70 |
| Goosegrass | — | — | — | 10 | — | — |
| Johnsongrass | 5 | 5 | 10 | 15 | 10 | 5 |
| Kochia | 80 | 85 | 90 | 35 | 90 | 90 |
| Lambsquarters | — | 70 | 90 | 40 | 95 | 75 |
| Morningglory | — | — | — | 75 | 70 | 65 |
| Nutsedge, Yellow | 5 | 5 | 5 | 5 | 5 | 5 |
| Oat, Wild | 5 | 5 | 25 | 30 | 30 | 15 |
| Oilseed Rape | 5 | 30 | 85 | — | 60 | 20 |
| Pigweed | 55 | 55 | 95 | 65 | 90 | 60 |
| Ragweed | 50 | 60 | 55 | 50 | 25 | 70 |
| Ryegrass, Italian | 5 | 5 | 10 | 5 | 5 | 5 |
| Soybean | 40 | 30 | 50 | 90 | 50 | 90 |
| Surinam Grass | — | — | — | 10 | — | — |
| Velvetleaf | 20 | 30 | 45 | 30 | 50 | 20 |
| Waterhemp | 50 | 75 | 98 | — | 90 | — |
| Wheat | 5 | 5 | 10 | 5 | 5 | 5 |
| Windgrass | — | — | — | 20 | — | — |

| 31 g ai/ha | Compounds | | | | | |
|---|---|---|---|---|---|---|
| Postemergence | 1 | 2 | 6 | 14 | 16 | 17 |
| Barley | — | — | — | 5 | — | — |
| Barnyardgrass | 10 | 5 | 10 | — | 10 | 5 |
| Bermudagrass | — | — | — | 5 | — | — |
| Blackgrass | 5 | 5 | 30 | 5 | 5 | 5 |
| Bromegrass, Downy | — | — | — | 5 | — | — |
| Canarygrass | — | — | — | 5 | — | — |
| Chickweed | 40 | 60 | 80 | 35 | 80 | 70 |
| Cocklebur | — | — | — | 35 | — | — |
| Corn | 5 | — | 15 | 20 | 20 | 10 |
| Crabgrass, Large | 5 | 5 | 10 | 10 | 10 | 10 |
| Cupgrass, Woolly | — | — | — | 5 | — | — |
| Deadnettle | — | — | — | 85 | — | — |
| Foxtail, Giant | 10 | 10 | 25 | 5 | 15 | 10 |
| Foxtail, Green | — | — | — | 10 | — | — |
| Galium | 40 | 50 | 90 | 50 | 80 | 60 |
| Goosegrass | — | — | — | 5 | — | — |
| Johnsongrass | 5 | 5 | 5 | 10 | 10 | 5 |
| Kochia | 80 | 80 | 90 | 25 | 90 | 80 |
| Lambsquarters | 60 | 55 | 75 | 40 | 70 | 75 |
| Morningglory | 60 | 10 | — | 75 | 50 | 65 |
| Nutsedge, Yellow | 0 | 5 | 5 | 5 | 5 | 5 |
| Oat, Wild | 5 | 5 | 20 | 20 | 15 | 10 |
| Oilseed Rape | 5 | 5 | 85 | — | 60 | 5 |
| Pigweed | 35 | — | 85 | 60 | 55 | — |
| Ragweed | 30 | 25 | 50 | 50 | 15 | 40 |
| Ryegrass, Italian | 5 | 5 | 5 | 5 | 5 | 5 |
| Soybean | 35 | 20 | 35 | 90 | — | 80 |
| Surinam Grass | — | — | — | 5 | — | — |
| Velvetleaf | 10 | 25 | 45 | 10 | 25 | 20 |
| Waterhemp | 50 | 75 | 95 | — | 80 | 60 |
| Wheat | 0 | 5 | 10 | 5 | 5 | 5 |
| Windgrass | — | — | — | 20 | — | — |

| 250 g ai/ha | Compounds | | | | | |
|---|---|---|---|---|---|---|
| Preemergence | 1 | 2 | 14 | 16 | 17 | 25 |
| Barnyardgrass | 100 | 98 | — | 100 | 100 | 98 |
| Bermudagrass | — | — | 98 | — | — | — |

TABLE C-continued

| | | | | | | |
|---|---|---|---|---|---|---|
| Blackgrass | 90 | 90 | 15 | 90 | 95 | 90 |
| Bromegrass, Downy | — | — | 30 | — | — | — |
| Corn | 95 | 75 | 75 | 75 | 100 | 45 |
| Crabgrass, Large | 100 | 100 | 100 | 100 | 100 | 100 |
| Cupgrass, Woolly | — | — | 98 | — | — | — |
| Foxtail, Giant | 100 | 100 | 100 | 100 | 100 | 100 |
| Foxtail, Green | — | — | 95 | — | — | — |
| Galium | 100 | 100 | 100 | 100 | 100 | 100 |
| Goosegrass | — | — | 100 | — | — | — |
| Johnsongrass | 100 | 90 | 85 | 98 | 100 | 98 |
| Kochia | — | — | 90 | — | — | — |
| Lambsquarters | 100 | 100 | 98 | 100 | 98 | 100 |
| Morningglory | 100 | 100 | 75 | 100 | 100 | 98 |
| Nightshade | — | — | 100 | — | — | — |
| Nutsedge, Yellow | 55 | — | 25 | 55 | 75 | 45 |
| Oat, Wild | — | — | 65 | — | — | — |
| Oilseed Rape | 100 | 100 | — | 100 | 100 | 95 |
| Pigweed | 100 | 100 | 100 | 100 | 100 | 100 |
| Ragweed | 100 | 60 | 55 | 100 | 98 | 95 |
| Russian Thistle | — | — | 90 | — | — | — |
| Ryegrass, Italian | 98 | 85 | 50 | 90 | 75 | 90 |
| Soybean | 98 | 60 | 75 | 75 | 98 | 65 |
| Sunflower | — | — | 10 | — | — | — |
| Surinam Grass | — | — | 75 | — | — | — |
| Velvetleaf | 100 | 85 | 100 | 100 | 100 | 95 |
| Waterhemp | 100 | 100 | — | 100 | 100 | 100 |
| Wheat | 70 | 30 | 25 | 50 | 65 | 70 |

| 125 g ai/ha | Compounds | | | | | |
|---|---|---|---|---|---|---|
| Preemergence | 1 | 2 | 14 | 16 | 17 | 25 |
| Barnyardgrass | 100 | 90 | — | 95 | 100 | 95 |
| Bermudagrass | — | — | 98 | — | — | — |
| Blackgrass | 90 | 90 | 15 | 60 | 90 | 90 |
| Bromegrass, Downy | — | — | 5 | — | — | — |
| Corn | 90 | 75 | 50 | 75 | 85 | 35 |
| Crabgrass, Large | 100 | 100 | 100 | 100 | 100 | 100 |
| Cupgrass, Woolly | — | — | 98 | — | — | — |
| Foxtail, Giant | 100 | 100 | 100 | 100 | 100 | 100 |
| Foxtail, Green | — | — | 95 | — | — | — |
| Galium | 100 | 98 | 100 | 100 | 100 | 100 |
| Goosegrass | — | — | 100 | — | — | — |
| Johnsongrass | 85 | 80 | 35 | 85 | 98 | 90 |
| Kochia | — | — | 90 | — | — | — |
| Lambsquarters | 100 | 100 | 95 | 100 | 95 | 100 |
| Morningglory | 100 | 85 | 65 | 100 | 100 | 100 |
| Nightshade | — | — | 98 | — | — | — |
| Nutsedge, Yellow | 50 | 35 | 25 | 30 | 55 | 15 |
| Oat, Wild | — | — | 65 | — | — | — |
| Oilseed Rape | 100 | 100 | — | 100 | 100 | 95 |
| Pigweed | 100 | 100 | 100 | 100 | 100 | 98 |
| Ragweed | 70 | 60 | 30 | 65 | 80 | 65 |
| Russian Thistle | — | — | 90 | — | — | — |
| Ryegrass, Italian | 85 | 65 | 30 | 85 | 70 | 90 |
| Soybean | 95 | 55 | 55 | 65 | 95 | 35 |
| Sunflower | — | — | 5 | — | — | — |
| Surinam Grass | — | — | 75 | — | — | — |
| Velvetleaf | 40 | 85 | 20 | 100 | 100 | 70 |
| Waterhemp | 100 | 100 | — | 100 | 100 | 100 |
| Wheat | 15 | 10 | 15 | 45 | 50 | 50 |

| 62 g ai/ha | Compounds | | | | | | |
|---|---|---|---|---|---|---|---|
| Preemergence | 1 | 2 | 14 | 16 | 17 | 23 | 25 |
| Barnyardgrass | 85 | 70 | — | 80 | 90 | 25 | 85 |
| Bermudagrass | — | — | 98 | — | — | — | — |
| Blackgrass | 30 | 45 | 10 | 50 | 80 | 5 | 85 |
| Bromegrass, Downy | — | — | 5 | — | — | — | — |
| Corn | 50 | 55 | 35 | 60 | 65 | 15 | 30 |
| Crabgrass, Large | 100 | 80 | 100 | 98 | 100 | 100 | 100 |
| Cupgrass, Woolly | — | — | 95 | — | — | — | — |
| Foxtail, Giant | 100 | 98 | 98 | 98 | 100 | 90 | 100 |
| Foxtail, Green | — | — | 95 | — | — | — | — |
| Galium | 100 | 85 | 98 | 98 | 100 | 95 | 90 |
| Goosegrass | — | — | 80 | — | — | — | — |
| Johnsongrass | 60 | 70 | 35 | 75 | 95 | 10 | 75 |
| Kochia | — | — | 75 | — | — | — | — |
| Lambsquarters | 100 | 100 | 95 | 100 | 95 | — | 100 |
| Morningglory | 90 | 65 | 60 | 95 | 85 | 98 | 95 |
| Nightshade | — | — | 98 | — | — | — | — |
| Nutsedge, Yellow | 30 | 25 | 5 | 10 | 30 | 0 | 5 |
| Oat, Wild | — | — | 0 | — | — | — | — |
| Oilseed Rape | 80 | 100 | — | 100 | 100 | 85 | 95 |
| Pigweed | 100 | 100 | 100 | 100 | 100 | 100 | 100 |
| Ragweed | 35 | 60 | 15 | 65 | 65 | 55 | 85 |
| Russian Thistle | — | — | 90 | — | — | — | — |
| Ryegrass, Italian | 10 | 15 | 5 | 30 | 10 | 5 | 40 |
| Soybean | 60 | 25 | 40 | 25 | 55 | 25 | 20 |
| Sunflower | — | — | 5 | — | — | — | — |
| Surinam Grass | — | — | 20 | — | — | — | — |
| Velvetleaf | 35 | 40 | 10 | 80 | 75 | 100 | 100 |
| Waterhemp | 100 | 100 | — | 100 | 100 | 100 | 100 |
| Wheat | 5 | 0 | 0 | 25 | 5 | 10 | 40 |

| 31 g ai/ha | Compounds | | | | | | |
|---|---|---|---|---|---|---|---|
| Preemergence | 1 | 2 | 14 | 16 | 17 | 23 | 25 |
| Barnyardgrass | 35 | 65 | — | 75 | 80 | 25 | 35 |
| Bermudagrass | — | — | 98 | — | — | — | — |
| Blackgrass | 30 | 10 | — | 40 | 50 | 50 | 40 |
| Bromegrass, Downy | — | — | 5 | — | — | — | — |
| Cocklebur | — | — | 0 | — | — | — | — |
| Corn | 15 | 35 | 0 | 45 | 45 | 5 | 10 |
| Crabgrass, Large | 100 | 75 | 80 | 98 | 100 | 65 | 100 |
| Cupgrass, Woolly | — | — | 65 | — | — | — | — |
| Foxtail, Giant | 100 | 45 | 80 | 98 | 100 | 75 | 100 |
| Foxtail, Green | — | — | 95 | — | — | — | — |
| Galium | 95 | — | 60 | 70 | 100 | 90 | 85 |
| Goosegrass | — | — | 45 | — | — | — | — |
| Johnsongrass | 35 | 65 | 5 | 60 | 70 | 5 | 65 |
| Kochia | — | — | 45 | — | — | — | — |
| Lambsquarters | 100 | 100 | 55 | 100 | 95 | — | 100 |
| Morningglory | 50 | 55 | 35 | 45 | 85 | 55 | 95 |
| Nightshade | — | — | 98 | — | — | — | — |
| Nutsedge, Yellow | 10 | 10 | 0 | 5 | 20 | 0 | 10 |
| Oat, Wild | — | — | 0 | — | — | — | — |
| Oilseed Rape | 30 | 100 | — | 65 | 50 | 80 | 50 |
| Pigweed | 100 | 100 | 100 | 100 | 100 | 100 | 100 |
| Ragweed | 25 | 15 | 5 | 20 | 35 | 60 | 60 |
| Russian Thistle | — | — | 85 | — | — | — | — |
| Ryegrass, Italian | 5 | 5 | 0 | 5 | 5 | 0 | 20 |
| Soybean | 30 | 25 | 10 | 10 | 10 | 20 | 20 |
| Sunflower | — | — | 5 | — | — | — | — |
| Surinam Grass | — | — | 5 | — | — | — | — |
| Velvetleaf | 5 | 35 | 0 | 65 | 55 | 65 | 60 |
| Waterhemp | 100 | 100 | — | 100 | 100 | 100 | 100 |
| Wheat | 0 | 0 | 0 | 10 | 0 | 0 | 10 |

| 16 g ai/ha Preemergence | Compound 23 | 8 g ai/ha Preemergence | Compound 23 |
|---|---|---|---|
| Barnyardgrass | 0 | Barnyardgrass | 0 |
| Blackgrass | 0 | Blackgrass | 0 |
| Corn | 5 | Corn | 0 |
| Crabgrass, Large | 50 | Crabgrass, Large | 5 |
| Foxtail, Giant | 55 | Foxtail, Giant | 5 |
| Galium | 85 | Galium | 85 |
| Johnsongrass | 5 | Johnsongrass | 0 |
| Morningglory | 20 | Morningglory | 10 |
| Nutsedge, Yellow | 0 | Nutsedge, Yellow | 0 |
| Oilseed Rape | 5 | Oilseed Rape | 5 |
| Pigweed | 100 | Pigweed | 98 |
| Ragweed | 60 | Ragweed | 0 |
| Ryegrass, Italian | 0 | Ryegrass, Italian | 0 |
| Soybean | 0 | Soybean | 0 |
| Velvetleaf | 15 | Velvetleaf | 0 |
| Waterhemp | 100 | Waterhemp | 85 |
| Wheat | 0 | Wheat | 0 |

Test D

Seeds of plant species selected from bluegrass (annual bluegrass, *Poa annua*), blackgrass (*Alopecurus myosuroides*), canarygrass (*Phalaris minor*), chickweed (common chickweed, *Stellaria media*), galium (catchweed bedstraw, *Galium aparine*), downy bromegrass (*Bromus tectorum*), field poppy (*Papaver rhoeas*), field violet (*Viola arvensis*), foxtail, green (green foxtail, *Setaria viridis*), deadnettle (henbit deadnettle, *Lamium amplexicaule*), ryegrass, Italian (Italian ryegrass, *Lolium multiflorum*), kochia (*Kochia scoparia*), lambsquarters (*Chenopodium album*), oilseed rape (*Brassica napus*), pigweed (*Amaranthus retroflexus*), chamomile (scentless chamomile, *Matricaria inodora*), Russian thistle (*Salsola kali*), speedwell (bird's-eye speedwell, *Veronica persica*), barley, spring (spring barley, *Hordeum vulgare*), wheat, spring (spring wheat, *Triticum aestivum*), buckwheat, wild (wild buckwheat, *Polygonum convolvulus*), mustard, wild (wild mustard, *Sinapis arvensis*), oat, wild (wild oat, *Avena fatua*), radish, wild (wild radish, *Raphanus raphanistrum*), windgrass (*Apera spica-venti*), barley, winter (winter barley, *Hordeum vulgare*), and wheat, winter (winter wheat, *Triticum aestivum*) were planted into a silt loam soil and treated preemergence with test chemicals formulated in a non-phytotoxic solvent mixture which included a surfactant.

At the same time, these species were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of the test chemicals formulated in the same manner. Plants ranged in height from 2 to 18 cm (1- to 4-leaf stage). Treated plants and controls were maintained in a controlled growth environment for 14 to 21 d after which time all species were compared to controls and visually evaluated. Plant response ratings, summarized in Table D, are based on a scale of 0 to 100 where 0 is no effect and 100 is complete control. A dash (-) response means no test result.

TABLE D

| 500 g ai/ha | Compounds | | | 250 g ai/ha | Compounds | | | |
|---|---|---|---|---|---|---|---|---|
| Postemergence | 1 | 2 | 17 | Postemergence | 1 | 2 | 14 | 17 |
| Barley, Spring | 10 | 25 | 35 | Barley, Spring | 10 | 15 | 20 | 15 |
| Barley, Winter | 15 | 25 | 35 | Barley, Winter | 10 | 20 | 25 | 30 |
| Blackgrass | 20 | 50 | 50 | Blackgrass | 20 | 30 | 10 | 20 |
| Bluegrass | 10 | 30 | 20 | Bluegrass | 10 | 20 | 30 | 10 |
| Bromegrass, Downy | 25 | 45 | 30 | Bromegrass, Downy | 15 | 40 | 20 | 25 |
| Buckwheat, Wild | 60 | 80 | 100 | Buckwheat, Wild | 40 | 70 | 70 | 75 |
| Canarygrass | 20 | 25 | 35 | Canarygrass | 20 | 20 | 25 | 30 |
| Chamomile | 50 | 60 | 60 | Chamomile | 60 | 40 | 25 | 60 |
| Chickweed | 60 | 100 | 100 | Chickweed | 50 | 75 | 90 | 100 |
| Deadnettle | 75 | 90 | 100 | Deadnettle | 50 | 75 | 80 | 98 |
| Field Poppy | 85 | 100 | 100 | Field Poppy | 80 | 80 | 80 | 90 |
| Field Violet | 90 | 100 | 100 | Field Violet | 80 | 100 | 100 | 100 |
| Foxtail, Green | 70 | 75 | 80 | Foxtail, Green | 20 | 45 | 15 | 30 |
| Galium | 90 | 85 | 100 | Galium | 70 | 75 | 75 | 98 |
| Kochia | 70 | 85 | 90 | Kochia | 50 | 85 | 90 | 80 |
| Lambsquarters | 45 | 90 | 100 | Lambsquarters | 40 | 80 | 90 | 95 |
| Mustard, Wild | 80 | 100 | 100 | Mustard, Wild | 80 | 100 | 95 | 100 |
| Oat, Wild | 10 | 30 | 50 | Oat, Wild | 10 | 15 | 30 | 20 |
| Oilseed Rape | 80 | 100 | 100 | Oilseed Rape | 75 | 98 | 55 | 85 |
| Pigweed | 50 | 30 | 95 | Pigweed | 40 | 30 | 75 | 70 |
| Radish, Wild | 90 | 100 | 100 | Radish, Wild | 50 | 100 | 80 | 100 |
| Russian Thistle | — | 100 | 100 | Russian Thistle | 50 | 80 | 35 | 100 |
| Ryegrass, Italian | 10 | 25 | 35 | Ryegrass, Italian | 10 | 20 | 15 | 15 |
| Speedwell | 100 | 100 | 100 | Speedwell | 40 | 100 | 100 | 100 |
| Wheat, Spring | 10 | 20 | 30 | Wheat, Spring | 10 | 15 | 15 | 20 |
| Wheat, Winter | 10 | 20 | 20 | Wheat, Winter | 5 | 15 | 15 | 10 |
| Windgrass | 20 | 35 | 25 | Windgrass | 20 | 25 | 60 | 10 |

| 125 g ai/ha | Compounds | | | | 62 g ai/ha | Compounds | | | |
|---|---|---|---|---|---|---|---|---|---|
| Postemergence | 1 | 2 | 14 | 17 | Postemergence | 1 | 2 | 14 | 17 |
| Barley, Spring | 5 | 10 | 20 | 15 | Barley, Spring | 0 | 10 | 15 | 10 |
| Barley, Winter | 0 | 15 | 20 | 25 | Barley, Winter | 0 | 15 | 20 | 15 |
| Blackgrass | 10 | 20 | 10 | 10 | Blackgrass | 10 | 15 | 10 | 10 |
| Bluegrass | 10 | 20 | 15 | 5 | Bluegrass | 5 | 15 | 20 | 5 |
| Bromegrass, Downy | 10 | 30 | 20 | 15 | Bromegrass, Downy | 0 | 30 | 10 | 10 |
| Buckwheat, Wild | 30 | 50 | 70 | 40 | Buckwheat, Wild | 20 | 30 | 75 | 10 |
| Canarygrass | 15 | 20 | 20 | 20 | Canarygrass | 10 | 20 | 15 | 20 |
| Chamomile | 30 | 30 | 20 | 40 | Chamomile | 30 | 30 | 10 | 40 |
| Chickweed | 50 | 70 | 70 | 60 | Chickweed | 30 | 40 | 45 | 40 |
| Deadnettle | 35 | 70 | 65 | 65 | Deadnettle | 25 | 40 | 60 | 50 |
| Field Poppy | 60 | 100 | 50 | 75 | Field Poppy | 60 | 75 | 75 | 75 |
| Field Violet | 75 | 100 | 100 | 80 | Field Violet | 50 | 90 | 65 | 70 |
| Foxtail, Green | 0 | 40 | 15 | 15 | Foxtail, Green | 0 | 5 | 20 | 10 |
| Galium | 45 | 50 | 65 | 90 | Galium | 30 | 40 | 60 | 70 |
| Kochia | 30 | 80 | 85 | 70 | Kochia | 20 | 70 | 65 | 60 |
| Lambsquarters | 40 | 40 | 80 | 80 | Lambsquarters | 20 | 20 | 70 | 50 |
| Mustard, Wild | 30 | 80 | 75 | 80 | Mustard, Wild | 20 | 70 | 65 | 50 |

TABLE D-continued

| | | | | | | | | | |
|---|---|---|---|---|---|---|---|---|---|
| Oat, Wild | 10 | 10 | 20 | 10 | Oat, Wild | 10 | 10 | 15 | 10 |
| Oilseed Rape | 50 | 80 | 45 | 75 | Oilseed Rape | 40 | 75 | 15 | 55 |
| Pigweed | 30 | 20 | 75 | 30 | Pigweed | 30 | 20 | 70 | 30 |
| Radish, Wild | 35 | 90 | 75 | 60 | Radish, Wild | 25 | 20 | 70 | 35 |
| Russian Thistle | — | — | 20 | 100 | Russian Thistle | 20 | 25 | 15 | 30 |
| Ryegrass, Italian | 5 | 15 | 15 | 10 | Ryegrass, Italian | 0 | 10 | 10 | 10 |
| Speedwell | 100 | 100 | 100 | 100 | Speedwell | 80 | 100 | 100 | 100 |
| Wheat, Spring | 5 | 10 | 15 | 20 | Wheat, Spring | 5 | 10 | 15 | 15 |
| Wheat, Winter | 5 | 15 | 15 | 10 | Wheat, Winter | 0 | 10 | 15 | 5 |
| Windgrass | 20 | 20 | 10 | 5 | Windgrass | 20 | 15 | 10 | 5 |

| 31 g ai/ha | Compounds | | | | 16 g ai/ha | Compound |
|---|---|---|---|---|---|---|
| Postemergence | 1 | 2 | 14 | 17 | Postemergence | 14 |
| Barley, Spring | 0 | 10 | 10 | 5 | Barley, Spring | 5 |
| Barley, Winter | 0 | 10 | 15 | 15 | Barley, Winter | 10 |
| Blackgrass | 0 | 5 | 10 | 10 | Blackgrass | 5 |
| Bluegrass | 5 | 10 | 20 | 5 | Bluegrass | 15 |
| Bromegrass, Downy | 0 | 10 | 10 | 10 | Bromegrass, Downy | 10 |
| Buckwheat, Wild | 20 | 20 | 55 | 10 | Buckwheat, Wild | 55 |
| Canarygrass | 5 | 20 | 15 | 10 | Canarygrass | 15 |
| Chamomile | 30 | 30 | 10 | 20 | Chamomile | 5 |
| Chickweed | 30 | 30 | 60 | 10 | Chickweed | 50 |
| Deadnettle | 10 | 40 | 60 | 50 | Deadnettle | 50 |
| Field Poppy | 30 | 25 | 20 | 50 | Field Poppy | 75 |
| Field Violet | 20 | 50 | 70 | 60 | Field Violet | 60 |
| Foxtail, Green | 0 | 0 | 10 | 10 | Foxtail, Green | 30 |
| Galium | 30 | 40 | 60 | 50 | Galium | 60 |
| Kochia | 15 | 40 | 60 | 25 | Kochia | 60 |
| Lambsquarters | 20 | 20 | 60 | 10 | Lambsquarters | 55 |
| Mustard, Wild | 20 | 10 | 60 | 20 | Mustard, Wild | 65 |
| Oat, Wild | 10 | 10 | 10 | 10 | Oat, Wild | 10 |
| Oilseed Rape | 35 | 60 | 50 | 50 | Oilseed Rape | 25 |
| Pigweed | 20 | 20 | 60 | 20 | Pigweed | 60 |
| Radish, Wild | 10 | 20 | 80 | 30 | Radish, Wild | 40 |
| Russian Thistle | — | — | 10 | 30 | Russian Thistle | 20 |
| Ryegrass, Italian | 0 | 0 | 5 | 10 | Ryegrass, Italian | 5 |
| Speedwell | 30 | 100 | 100 | 10 | Speedwell | 100 |
| Wheat, Spring | 0 | 10 | 10 | 10 | Wheat, Spring | 5 |
| Wheat, Winter | 0 | 10 | 10 | 0 | Wheat, Winter | 5 |
| Windgrass | 20 | 10 | 5 | 0 | Windgrass | 5 |

| 500 g ai/ha | Compounds | | | 250 g ai/ha | Compounds | | | |
|---|---|---|---|---|---|---|---|---|
| Preemergence | 1 | 2 | 17 | Preemergence | 1 | 2 | 14 | 17 |
| Barley, Spring | 70 | 50 | 90 | Barley, Spring | 30 | 25 | 5 | 70 |
| Barley, Winter | 60 | 50 | 80 | Barley, Winter | 40 | 30 | 5 | 75 |
| Blackgrass | 75 | 80 | 90 | Blackgrass | 40 | 60 | 70 | 60 |
| Bluegrass | 45 | 100 | 85 | Bluegrass | 15 | 30 | 35 | 60 |
| Bromegrass, Downy | 25 | 25 | 50 | Bromegrass, Downy | 25 | 20 | 0 | 30 |
| Buckwheat, Wild | 70 | 100 | 100 | Buckwheat, Wild | 70 | 100 | 100 | 100 |
| Canarygrass | 30 | 85 | 50 | Canarygrass | 15 | 40 | 80 | 30 |
| Chamomile | 100 | 90 | 100 | Chamomile | 90 | 50 | 80 | 100 |
| Chickweed | 100 | 100 | 100 | Chickweed | 100 | 100 | 95 | 100 |
| Deadnettle | 100 | 100 | 100 | Deadnettle | 100 | 100 | 100 | 100 |
| Field Poppy | 100 | 100 | 100 | Field Poppy | 100 | 100 | 100 | 100 |
| Field Violet | 100 | 100 | 100 | Field Violet | 98 | 100 | 100 | 100 |
| Foxtail, Green | 100 | 100 | 100 | Foxtail, Green | 100 | 100 | 100 | 100 |
| Galium | 100 | 100 | 100 | Galium | 70 | 100 | — | 100 |
| Kochia | 100 | 100 | 100 | Kochia | 100 | 100 | 100 | 100 |
| Lambsquarters | 100 | 90 | 90 | Lambsquarters | 90 | 90 | 95 | 90 |
| Mustard, Wild | 95 | 100 | 100 | Mustard, Wild | 95 | 100 | 100 | 100 |
| Oat, Wild | 80 | 80 | 85 | Oat, Wild | 35 | 80 | 20 | 75 |
| Oilseed Rape | 98 | 95 | 90 | Oilseed Rape | 75 | 95 | 70 | 90 |
| Pigweed | 100 | 100 | 100 | Pigweed | 100 | 85 | 100 | 100 |
| Radish, Wild | 100 | 100 | 100 | Radish, Wild | 100 | 100 | 100 | 100 |
| Russian Thistle | 100 | 100 | 100 | Russian Thistle | 100 | 100 | 95 | 100 |
| Ryegrass, Italian | 60 | 35 | 80 | Ryegrass, Italian | 20 | 30 | 25 | 50 |
| Speedwell | 100 | 100 | 100 | Speedwell | 100 | 100 | 100 | 100 |
| Wheat, Spring | 75 | 50 | 90 | Wheat, Spring | 15 | 30 | 15 | 70 |

TABLE D-continued

| | | | | | | | | |
|---|---|---|---|---|---|---|---|---|
| Wheat, Winter | 70 | 45 | 90 | Wheat, Winter | 50 | 40 | 10 | 30 |
| Windgrass | 100 | 100 | 100 | Windgrass | 100 | 95 | 65 | 100 |

| 125 g ai/ha | Compounds | | | | 62 g ai/ha | Compounds | | | |
|---|---|---|---|---|---|---|---|---|---|
| Preemergence | 1 | 2 | 14 | 17 | Preemergence | 1 | 2 | 14 | 17 |
| Barley, Spring | 5 | 0 | 15 | 20 | Barley, Spring | 5 | 0 | 5 | 20 |
| Barley, Winter | 5 | 30 | 5 | 40 | Barley, Winter | 5 | 0 | 5 | 20 |
| Blackgrass | 20 | 60 | 20 | 30 | Blackgrass | 0 | 20 | 10 | 10 |
| Bluegrass | 0 | 10 | 10 | 25 | Bluegrass | 0 | 0 | 0 | 0 |
| Bromegrass, Downy | 20 | 0 | 0 | 15 | Bromegrass, Downy | 0 | 0 | 0 | 10 |
| Buckwheat, Wild | 70 | 25 | 25 | 30 | Buckwheat, Wild | 40 | 20 | 25 | 10 |
| Canarygrass | 5 | 40 | 35 | 10 | Canarygrass | 0 | 25 | 20 | 0 |
| Chamomile | 70 | 25 | 85 | 95 | Chamomile | — | 0 | 25 | 80 |
| Chickweed | 100 | 100 | 100 | 100 | Chickweed | 100 | 100 | — | 100 |
| Deadnettle | 100 | 100 | 65 | 100 | Deadnettle | 40 | 100 | 40 | 100 |
| Field Poppy | 95 | 100 | 100 | 100 | Field Poppy | 95 | 100 | 100 | 100 |
| Field Violet | 90 | 90 | 95 | 90 | Field Violet | 80 | 80 | 100 | 85 |
| Foxtail, Green | 100 | 85 | 70 | 100 | Foxtail, Green | 60 | — | 40 | 95 |
| Galium | — | 75 | 5 | 20 | Galium | 10 | — | 0 | 5 |
| Kochia | 80 | 100 | 70 | 100 | Kochia | — | 30 | 95 | 100 |
| Lambsquarters | 20 | 75 | 95 | — | Lambsquarters | 0 | 75 | 20 | 95 |
| Mustard, Wild | — | 100 | 100 | 100 | Mustard, Wild | 40 | 100 | 40 | 100 |
| Oat, Wild | 15 | 35 | 10 | 50 | Oat, Wild | 0 | 0 | 0 | 0 |
| Oilseed Rape | 40 | 50 | 15 | 40 | Oilseed Rape | 30 | 20 | 10 | 25 |
| Pigweed | 100 | 70 | 100 | 100 | Pigweed | 20 | 60 | 75 | 100 |
| Radish, Wild | 60 | 100 | 100 | 100 | Radish, Wild | 75 | 100 | 100 | 100 |
| Russian Thistle | 100 | 100 | 50 | 100 | Russian Thistle | 20 | 0 | 85 | 100 |
| Ryegrass, Italian | 10 | 25 | 15 | 0 | Ryegrass, Italian | 0 | 0 | 0 | 0 |
| Speedwell | 100 | 100 | — | 100 | Speedwell | 100 | 100 | — | 100 |
| Wheat, Spring | 10 | 15 | 10 | 30 | Wheat, Spring | 0 | 0 | 0 | 15 |
| Wheat, Winter | 10 | 30 | 5 | 0 | Wheat, Winter | 0 | 0 | 5 | 0 |
| Windgrass | 100 | 60 | 35 | 100 | Windgrass | 20 | 50 | 5 | 80 |

| 31 g ai/ha | Compounds | | | | 16 g ai/ha | Compound |
|---|---|---|---|---|---|---|
| Preemergence | 1 | 2 | 14 | 17 | Preemergence | 14 |
| Barley, Spring | 0 | 0 | 10 | 15 | Barley, Spring | 5 |
| Barley, Winter | 0 | 0 | 5 | 10 | Barley, Winter | 15 |
| Blackgrass | 0 | 5 | 0 | 0 | Blackgrass | 0 |
| Bluegrass | 0 | 0 | 0 | 0 | Bluegrass | 5 |
| Bromegrass, Downy | 0 | 0 | 0 | 10 | Bromegrass, Downy | 0 |
| Buckwheat, Wild | 0 | 0 | 15 | 0 | Buckwheat, Wild | 15 |
| Canarygrass | 0 | 0 | 5 | 0 | Canarygrass | 5 |
| Chamomile | — | 0 | 10 | 0 | Chamomile | 5 |
| Chickweed | 100 | 100 | — | 100 | Chickweed | 10 |
| Deadnettle | 20 | 100 | 15 | 100 | Deadnettle | 60 |
| Field Poppy | 50 | 100 | 100 | 100 | Field Poppy | 95 |
| Field Violet | 60 | 60 | 95 | 75 | Field Violet | 85 |
| Foxtail, Green | 0 | 20 | 15 | 15 | Foxtail, Green | 0 |
| Galium | 0 | 0 | 0 | 5 | Galium | 0 |
| Kochia | 70 | 20 | 65 | 100 | Kochia | 35 |
| Lambsquarters | 0 | 20 | 25 | 90 | Lambsquarters | 5 |
| Mustard, Wild | — | 0 | 35 | 100 | Mustard, Wild | 30 |
| Oat, Wild | — | 0 | 0 | 0 | Oat, Wild | 0 |
| Oilseed Rape | 30 | 20 | 5 | 25 | Oilseed Rape | 0 |
| Pigweed | — | 30 | 95 | 10 | Pigweed | 35 |
| Radish, Wild | — | 100 | 100 | 30 | Radish, Wild | 100 |
| Russian Thistle | — | — | 50 | 0 | Russian Thistle | 0 |
| Ryegrass, Italian | 0 | 0 | 0 | 0 | Ryegrass, Italian | 0 |
| Speedwell | 100 | 100 | — | 100 | Wheat, Spring | 0 |
| Wheat, Spring | 0 | 0 | 0 | 0 | Wheat, Winter | 0 |
| Wheat, Winter | 0 | 0 | 5 | 0 | Windgrass | 10 |
| Windgrass | 0 | 20 | 5 | 80 | | |

Test E

Seeds of plant species selected from corn (*Zea mays*), soybean (*Glycine max*), lambsquarters (*Chenopodium album*), poinsettia, wild (wild poinsettia, *Euphorbia heterophylla*), pigweed, palmer (palmer pigweed, *Amaranthus palmeri*), waterhemp (common waterhemp, *Amaranthus rudis*), surinam grass (*Brachiaria decumbens*), crabgrass, large (large crabgrass *Digitaria sanguinalis*), crabgrass, Brazil (Brazilian crabgrass, *Digitaria horizontalis*), panicum, fall (fall panicum, *Panicum dichotomiflorum*), foxtail, giant (giant foxtail, *Setaria faberii*), foxtail, green (green foxtail, *Setaria viridis*), goosegrass (*Eleusine indica*), johnsongrass (*Sorghum halepense*), ragweed (common ragweed, *Ambrosia elatior*), barnyardgrass (*Echinochloa crus-galli*), sandbur (southern sandbur, *Cenchrus echinatus*), arrowleaf sida (*Sida rhombifolia*), ryegrass, Italian (Italian ryegrass, *Lolium multiflorum*), dayflower, VA (Virginia dayflower, *Commelina virginica*), field bindweed (*Convolvulus arvensis*), cocklebur (common cocklebur, *Xanthium strumarium*), morningglory (*Ipomoea coccinea*), nightshade (eastern black nightshade, *Solanum ptycanthum*), kochia (*Kochia scoparia*), nutsedge, yellow (yellow nutsedge, *Cyperus esculentus*), smartweed (ladysthumb smartweed, *Polygonum persicaria*), velvetleaf (*Abutilon theophrasti*), and beggarticks (hairy beggarticks, *Bidens pilosa*), were planted into a silt loam soil and treated preemergence with test chemicals formulated in a non-phytotoxic solvent mixture which included a surfactant.

At the same time, plants from these crop and weed species and also waterhemp_RES1, (ALS & Triazine resistant common waterhemp, *Amaranthus rudis*), and waterhemp_RES2, (ALS & HPPD resistant common waterhemp, *Amaranthus rudis*) were planted in pots containing Redi-Earth® planting medium (Scotts Company, 14111 Scottslawn Road, Marysville, Ohio 43041) comprising spaghnum peat moss, vermiculite, wetting agent and starter nutrients were treated with postemergence applications of test chemicals formulated in the same manner. Plants ranged in height from 2 to 18 cm for postemergence treatments (1- to 4-leaf stage). Treated plants and controls were maintained in a greenhouse for 14 to 21 d, after which time all species were compared to controls and visually evaluated. Plant response ratings, summarized in Table E, are based on a scale of 0 to 100 where 0 is no effect and 100 is complete control. A dash (-) response means no test result.

TABLE E

Postemergence

| | 250 g ai/ha Compounds | |
|---|---|---|
| | 16 | 17 |
| Arrowleaf Sida | 80 | 70 |
| Barnyardgrass | 50 | 65 |
| Beggarticks | 50 | 55 |
| Corn | 50 | 65 |
| Crabgrass, Brazil | 50 | 70 |
| Dayflower, VA | 70 | 40 |
| Field Bindweed | 75 | 75 |
| Panicum, Fall | 50 | 50 |
| Pigweed, Palmer | 95 | 100 |
| Poinsettia, Wild | 75 | 50 |
| Ryegrass, Italian | 40 | 15 |
| Sandbur | 50 | 75 |
| Smartweed | 70 | 60 |
| Soybean | 85 | 85 |
| Waterhemp | 100 | 95 |
| Waterhemp_RES1 | 100 | 90 |
| Waterhemp_RES2 | 100 | 95 |

| | 125 g ai/ha Compounds | |
|---|---|---|
| | 16 | 17 |
| Arrowleaf Sida | — | 50 |
| Barnyardgrass | 30 | 20 |
| Beggarticks | 50 | 35 |
| Corn | 40 | 35 |
| Crabgrass, Brazil | 30 | 30 |
| Dayflower, VA | 60 | 30 |
| Field Bindweed | 65 | 60 |
| Panicum, Fall | 40 | 30 |
| Pigweed, Palmer | 75 | 80 |
| Poinsettia, Wild | 70 | 40 |
| Ryegrass, Italian | 20 | 0 |
| Sandbur | 35 | 35 |
| Smartweed | 70 | 40 |
| Soybean | 50 | 60 |
| Waterhemp | 80 | 85 |
| Waterhemp_RES1 | 100 | 85 |
| Waterhemp_RES2 | 95 | 90 |

| | 62 g ai/ha Compounds | |
|---|---|---|
| | 16 | 17 |
| Arrowleaf Sida | 60 | 50 |
| Barnyardgrass | 15 | 20 |
| Beggarticks | 30 | 30 |
| Corn | 30 | 10 |
| Crabgrass, Brazil | 20 | 20 |
| Dayflower, VA | 20 | 15 |
| Field Bindweed | 50 | 50 |
| Panicum, Fall | 30 | 20 |
| Pigweed, Palmer | 70 | 30 |
| Poinsettia, Wild | 60 | 40 |
| Ryegrass, Italian | 20 | 0 |
| Sandbur | 30 | 20 |
| Smartweed | 40 | 30 |
| Soybean | 35 | 50 |
| Waterhemp | 80 | 80 |
| Waterhemp_RES1 | 95 | 60 |
| Waterhemp_RES2 | 90 | 80 |

| | 31 g ai/ha Compound 17 |
|---|---|
| Arrowleaf Sida | 40 |
| Barnyardgrass | 10 |
| Beggarticks | 30 |
| Corn | 10 |
| Crabgrass, Brazil | 20 |
| Dayflower, VA | 10 |
| Field Bindweed | 40 |
| Panicum, Fall | 20 |
| Pigweed, Palmer | 20 |
| Poinsettia, Wild | 30 |
| Ryegrass, Italian | 0 |
| Sandbur | 20 |
| Smartweed | 15 |
| Soybean | 30 |
| Waterhemp | 50 |
| Waterhemp_RES1 | 60 |
| Waterhemp_RES2 | 80 |

| | 16 g ai/ha Compound 17 |
|---|---|
| Arrowleaf Sida | 30 |
| Barnyardgrass | 0 |
| Beggarticks | 20 |
| Corn | 0 |
| Crabgrass, Brazil | 20 |
| Dayflower, VA | 10 |
| Field Bindweed | 40 |
| Panicum, Fall | 15 |
| Pigweed, Palmer | 20 |
| Poinsettia, Wild | 20 |
| Ryegrass, Italian | 0 |
| Sandbur | 10 |
| Smartweed | 10 |
| Soybean | 30 |
| Waterhemp | 40 |

TABLE E-continued

| | |
|---|---|
| Waterhemp_RES1 | 50 |
| Waterhemp_RES2 | 60 |

Preemergence

| | 250 g ai/ha Compounds | |
|---|---|---|
| | 16 | 17 |
| Arrowleaf Sida | 5 | 0 |
| Barnyardgrass | 70 | 80 |
| Beggarticks | 20 | 20 |
| Cocklebur | 0 | — |
| Corn | 65 | 80 |
| Crabgrass, Brazil | 100 | 100 |
| Crabgrass, Large | 100 | 100 |
| Dayflower, VA | 65 | 80 |
| Field Bindweed | 100 | 98 |
| Foxtail, Giant | 100 | 100 |
| Foxtail, Green | 100 | 100 |
| Goosegrass | 50 | 98 |
| Johnsongrass | 60 | 90 |
| *Kochia* | 98 | 98 |
| Lambsquarters | 100 | 100 |
| Morningglory | 80 | 70 |
| Nightshade | 100 | 98 |
| Nutsedge, Yellow | 40 | 70 |
| Panicum, Fall | 100 | 100 |
| Pigweed, Palmer | 98 | 100 |
| Poinsettia, Wild | 65 | 100 |
| Ragweed | 95 | 80 |
| Ryegrass, Italian | 50 | 75 |
| Sandbur | 80 | 98 |
| Smartweed | 100 | 75 |
| Soybean | 50 | 80 |
| Surinam Grass | 98 | 75 |
| Velvetleaf | 50 | 70 |
| Waterhemp | 100 | 98 |

| | 125 g ai/ha Compounds | | |
|---|---|---|---|
| | 16 | 17 | 25 |
| Arrowleaf Sida | 0 | 0 | 40 |
| Barnyardgrass | 50 | 80 | 60 |
| Beggarticks | 0 | 5 | 15 |
| Cocklebur | 0 | — | 65 |
| Corn | 40 | 65 | 35 |
| Crabgrass, Brazil | 100 | 100 | 100 |
| Crabgrass, Large | 100 | 100 | 100 |
| Dayflower, VA | 20 | — | 70 |
| Field Bindweed | 30 | 5 | 100 |
| Foxtail, Giant | 90 | 100 | 20 |
| Foxtail, Green | 95 | 75 | 100 |
| Goosegrass | 20 | 95 | 98 |
| Johnsongrass | 60 | 75 | 65 |
| *Kochia* | 98 | 98 | 95 |
| Lambsquarters | 98 | 98 | 100 |
| Morningglory | 65 | 65 | 65 |
| Nightshade | 100 | 98 | 100 |
| Nutsedge, Yellow | 20 | 50 | 0 |
| Panicum, Fall | 90 | 100 | 100 |
| Pigweed, Palmer | 98 | 80 | 100 |
| Poinsettia, Wild | 35 | 40 | 10 |
| Ragweed | 0 | 35 | 50 |
| Ryegrass, Italian | 20 | 50 | 50 |
| Sandbur | 65 | 70 | 60 |
| Smartweed | 98 | 20 | — |
| Soybean | 20 | 65 | 30 |
| Surinam Grass | 40 | 75 | 100 |
| Velvetleaf | 0 | 25 | 80 |
| Waterhemp | 100 | 98 | 100 |

| | 62 g ai/ha Compounds | | |
|---|---|---|---|
| | 16 | 17 | 25 |
| Arrowleaf Sida | 0 | 0 | 35 |
| Barnyardgrass | 35 | 35 | 35 |
| Beggarticks | 0 | 0 | 0 |
| Cocklebur | — | 0 | 65 |
| Corn | 40 | 30 | 40 |
| Crabgrass, Brazil | 100 | 100 | 100 |
| Crabgrass, Large | 100 | 100 | 100 |
| Dayflower, VA | 5 | 20 | 20 |
| Field Bindweed | 5 | 0 | 5 |
| Foxtail, Giant | 75 | 65 | 5 |
| Foxtail, Green | 50 | 75 | 90 |
| Goosegrass | 5 | 60 | 75 |
| Johnsongrass | 35 | 35 | 35 |
| *Kochia* | 98 | 95 | 100 |
| Lambsquarters | 98 | 98 | 100 |
| Morningglory | 25 | 60 | 50 |
| Nightshade | 80 | 98 | 98 |
| Nutsedge, Yellow | 20 | 35 | 0 |
| Panicum, Fall | 50 | 98 | 100 |
| Pigweed, Palmer | 98 | 25 | 100 |
| Poinsettia, Wild | 35 | 30 | 50 |
| Ragweed | 0 | 10 | 20 |
| Ryegrass, Italian | 20 | 25 | 40 |
| Sandbur | 40 | 40 | 30 |
| Smartweed | 98 | 0 | — |
| Soybean | 0 | 0 | 20 |
| Surinam Grass | 25 | 65 | 100 |
| Velvetleaf | 0 | 20 | 30 |
| Waterhemp | 100 | 98 | 100 |

| | 31 g ai/ha Compounds | |
|---|---|---|
| | 17 | 25 |
| Arrowleaf Sida | 0 | 5 |
| Barnyardgrass | 20 | 15 |
| Beggarticks | 0 | 0 |
| Cocklebur | — | 20 |
| Corn | 0 | 25 |
| Crabgrass, Brazil | 100 | 98 |
| Crabgrass, Large | 100 | 75 |
| Dayflower, VA | 10 | 15 |
| Field Bindweed | 0 | 0 |
| Foxtail, Giant | 40 | 0 |
| Foxtail, Green | 50 | 35 |
| Goosegrass | 20 | 15 |
| Johnsongrass | 10 | 10 |
| *Kochia* | 90 | 70 |
| Lambsquarters | 98 | 100 |
| Morningglory | 35 | 5 |
| Nightshade | 80 | 80 |
| Nutsedge, Yellow | 0 | 0 |
| Panicum, Fall | 90 | 50 |
| Pigweed, Palmer | 0 | 95 |
| Poinsettia, Wild | 20 | 0 |
| Ragweed | 0 | 0 |
| Ryegrass, Italian | 25 | 30 |
| Sandbur | 5 | 20 |
| Smartweed | 0 | — |
| Soybean | 0 | 0 |
| Surinam Grass | 20 | 80 |
| Velvetleaf | 0 | 0 |
| Waterhemp | 98 | 100 |

| | 16 g ai/ha Compounds | |
|---|---|---|
| | 17 | 25 |
| Arrowleaf Sida | 0 | 5 |
| Barnyardgrass | 0 | 5 |
| Beggarticks | 0 | 0 |
| Cocklebur | 0 | 50 |
| Corn | 0 | 10 |

TABLE E-continued

| | | |
|---|---|---|
| Crabgrass, Brazil | 100 | 75 |
| Crabgrass, Large | 35 | 0 |
| Dayflower, VA | 0 | 0 |
| Field Bindweed | 0 | 0 |
| Foxtail, Giant | 0 | 0 |
| Foxtail, Green | 0 | 5 |
| Goosegrass | 0 | 5 |
| Johnsongrass | 0 | 0 |
| Kochia | 70 | 50 |
| Lambsquarters | 98 | 98 |
| Morningglory | 0 | 0 |
| Nightshade | 0 | 50 |
| Nutsedge, Yellow | 0 | 0 |
| Panicum, Fall | 80 | 35 |
| Pigweed, Palmer | 0 | 95 |
| Poinsettia, Wild | 20 | 0 |
| Ragweed | 0 | 0 |
| Ryegrass, Italian | 20 | 30 |
| Sandbur | 0 | 0 |
| Smartweed | 0 | — |
| Soybean | 0 | 0 |
| Surinam Grass | 0 | 10 |
| Velvetleaf | 0 | 20 |
| Waterhemp | 75 | 50 |

| | 8 g ai/ha Compound 25 |
|---|---|
| Arrowleaf Sida | 0 |
| Barnyardgrass | 0 |
| Beggarticks | 0 |
| Cocklebur | 0 |
| Corn | 0 |
| Crabgrass, Brazil | 0 |
| Crabgrass, Large | 0 |
| Dayflower, VA | 0 |
| Field Bindweed | 0 |
| Foxtail, Giant | 0 |
| Foxtail, Green | 0 |
| Goosegrass | 5 |
| Johnsongrass | 0 |
| Kochia | 40 |
| Lambsquarters | 65 |
| Morningglory | 0 |
| Nightshade | 5 |
| Nutsedge, Yellow | 0 |
| Panicum, Fall | 0 |
| Pigweed, Palmer | 0 |
| Poinsettia, Wild | 0 |
| Ragweed | 0 |
| Ryegrass, Italian | 0 |
| Sandbur | 0 |
| Soybean | 0 |
| Surinam Grass | 5 |
| Velvetleaf | 0 |
| Waterhemp | 35 |

What is claimed is:
1. A compound selected from Formula 1, N-oxides and salts thereof

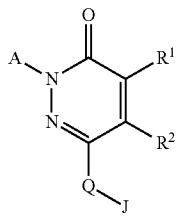

wherein

A is phenyl substituted with $R^3$; or a 5- or 6-membered heteroaromatic ring, said ring substituted with $R^4$ on carbon ring members and with $R^5$ on nitrogen ring members and attached to the remainder of Formula 1 through a carbon atom;

$R^1$ is H, halogen, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_6$ alkylcarbonyloxy, $C_1$-$C_4$ hydroxyalkyl, $SO_p(R^{16})$, $C_2$-$C_4$ alkylthioalkyl, $C_2$-$C_4$ alkylsulfonylalkyl, $C_1$-$C_4$ alkylamino, $C_2$-$C_4$ dialkylamino, $C_3$-$C_6$ cycloalkyl or hydroxy;

$R^2$ is H, halogen, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_6$ alkylcarbonyloxy, $C_1$-$C_4$ hydroxyalkyl, $SO_q(R^{17})$, $C_2$-$C_4$ alkylthioalkyl, $C_2$-$C_4$ alkylsulfonylalkyl, $C_1$-$C_4$ alkylamino, $C_2$-$C_4$ dialkylamino, $C_3$-$C_6$ cycloalkyl or hydroxy; or $R^1$ and $R^2$ are taken together as $C_3$-$C_6$ alkylene or $C_3$-$C_6$ alkenylene;

Q is $C(R^6)(R^7)$ or O;

J is phenyl substituted with 1 $R^9$ and optionally substituted with up to 2 $R^{10}$; or J is a 6-membered heteroaromatic ring substituted with 1 $R^9$ and optionally substituted with up to 2 $R^{10}$ on carbon ring members; or J is a 5-membered heteroaromatic ring substituted with 1 $R^{11}$ on carbon ring members and $R^{13}$ on nitrogen ring members; and optionally substituted with 1 $R^{12}$ on carbon ring members;

each $R^3$ is independently H, halogen, cyano, nitro, $SF_5$, $C_1$-$C_4$ alkoxy, $C_1$-$C_4$ haloalkoxy, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy or $S(O)_rR^{18}$;

each $R^4$ is independently H, halogen, cyano, nitro, $C_1$-$C_4$ alkyl, $C_1$-$C_4$ haloalkyl, $C_1$-$C_4$ alkoxy, $C_1$-$C_4$ haloalkoxy or $S(O)_tR^{19}$;

$R^5$ is H, $C_1$-$C_4$ alkyl or $C_1$-$C_4$ haloalkyl;

$R^6$ is H, F, Cl, Br, cyano, $C_1$-$C_4$ alkyl, OH, $C_1$-$C_4$ haloalkyl, $OR^{14a}$ or $CO_2R^{15a}$;

$R^7$ is H, F, Cl, Br, cyano, $C_1$-$C_4$ alkyl, OH, $C_1$-$C_4$ haloalkyl, $OR^{14b}$ or $CO_2R^{15b}$; or $R^6$ and $R^7$ are taken together with the carbon to which they both are attached to form $C(=O)$, $C(=NOR^{24})$ or $C(=N-N(R^{25})(R^{26}))$;

$R^9$ is $SF_5$, $C_1$-$C_4$ haloalkyl, $C_1$-$C_4$ haloalkoxy or $S(O)_uR^{20}$;

each $R^{10}$ is independently halogen, cyano, $C_1$-$C_4$ alkyl, $C_1$-$C_4$ haloalkyl, $C_1$-$C_4$ alkoxy, $C_1$-$C_4$ haloalkoxy or $S(O)_vR^{21}$; or $R^9$ and $R^{10}$ are taken together with two adjacent carbon atoms to form a 5-membered ring containing ring members selected from carbon atoms and up to two O atoms and up to two S atoms, and optionally substituted on carbon atom ring members with up to five halogen atoms;

$R^{11}$ is $SF_5$, $C_1$-$C_4$ haloalkyl, $C_1$-$C_4$ haloalkoxy or $S(O)_wR^{22}$;

$R^{12}$ is halogen, cyano, $C_1$-$C_4$ alkyl, $C_1$-$C_4$ haloalkyl, $C_1$-$C_4$ alkoxy, $C_1$-$C_4$ haloalkoxy or $S(O)_xR^{23}$;

$R^{13}$ is $C_1$-$C_4$ alkyl or $C_1$-$C_4$ haloalkyl;

each $R^{14a}$ and $R^{14b}$ is independently $C_1$-$C_4$ alkyl or $C_1$-$C_4$ haloalkyl; or $R^{14a}$ and $R^{14b}$ are taken together as —$CH_2CH_2$— or —$CH_2CH_2CH_2$—;

each $R^{15a}$ and $R^{15b}$ is independently $C_1$-$C_4$ alkyl or $C_1$-$C_4$ haloalkyl;

each $R^{16}$, $R^{17}$, $R^{18}$, $R^{19}$, $R^{20}$, $R^{22}$ and $R^{23}$ is independently $C_1$-$C_4$ alkyl or $C_1$-$C_4$ haloalkyl;

$R^{21}$ is $C_1$-$C_4$ haloalkyl;

$R^{24}$ is H or $C_1$-$C_4$ alkyl;

$R^{25}$ is $C_1$-$C_4$ alkyl or $C_1$-$C_4$ haloalkyl;

$R^{26}$ is $C_1$-$C_4$ alkyl or $C_1$-$C_4$ haloalkyl; and each p, q, r, t, u, v, w and x is independently 0, 1 or 2.

2. The compound of claim 1 wherein

A is phenyl substituted with $R^3$; or a 6-membered heteroaromatic ring, said ring substituted with $R^4$ on carbon ring members and with $R^5$ on nitrogen ring members and attached to the remainder of Formula 1 through a carbon atom;

$R^1$ is H, halogen, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl or $C_2$-$C_4$ alkynyl;

$R^2$ is H, halogen, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_6$ alkylcarbonyloxy, $C_1$-$C_4$ hydroxyalkyl, $SO_q(R^{17})$, $C_2$-$C_4$ alkylthioalkyl, $C_2$-$C_4$ alkylsulfonylalkyl, $C_1$-$C_4$ alkylamino, $C_2$-$C_4$ dialkylamino or $C_3$-$C_6$ cycloalkyl; or $R^1$ and $R^2$ are taken together as $C_3$-$C_6$ alkylene;

J is independently selected from J-1 through J-33;

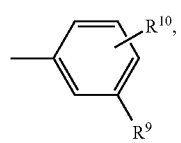 J-1

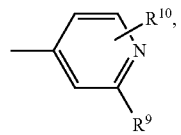 J-2

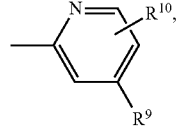 J-3

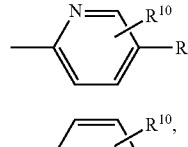 J-4

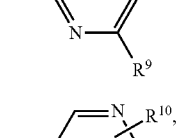 J-5

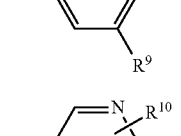 J-6

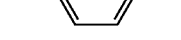 J-7

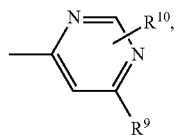 J-8

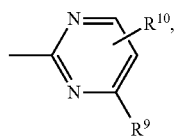 J-9

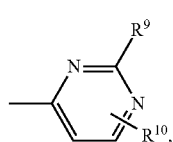 J-12

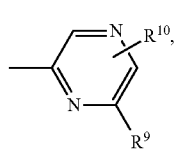 J-13

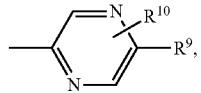 J-14

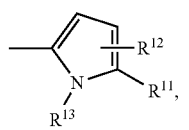 J-15

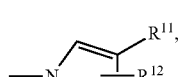 J-16

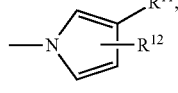 J-17

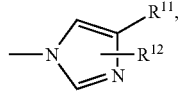 J-18

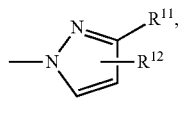 J-19

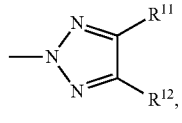 J-20

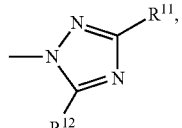 J-21

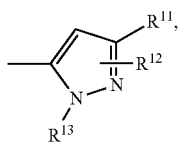

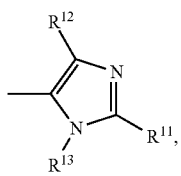

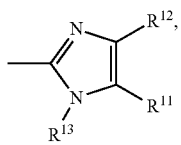

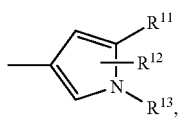

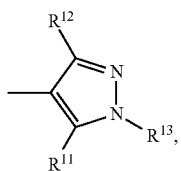

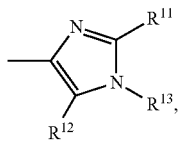

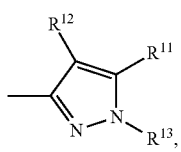

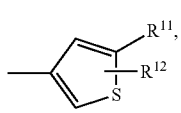

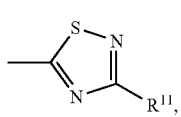

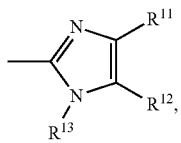

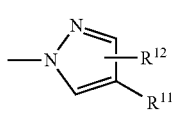 and

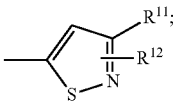

each $R^3$ is independently H, halogen, cyano, $C_1$-$C_4$ alkoxy, $C_1$-$C_4$ haloalkoxy, $C_1$-$C_4$ alkyl or $C_1$-$C_4$ haloalkyl;
each $R^4$ is independently H, halogen, nitro, $C_1$-$C_4$ alkyl, $C_1$-$C_4$ haloalkyl or $C_1$-$C_4$ alkoxy;
$R^5$ is H, halogen or $C_1$-$C_4$ haloalkyl;
$R^6$ is H, Cl or $C_1$-$C_4$ alkyl;
$R^7$ is H, F, Cl, OH, $C_1$-$C_4$ haloalkyl, $OR^{14b}$ or $CO_2R^{15b}$; or
$R^6$ and $R^7$ are taken together with the carbon to which they both are attached to form C(=O);
$R^9$ is $C_1$-$C_4$ haloalkyl, $C_1$-$C_4$ haloalkoxy or $S(O)_u R^{20}$;
each $R^{10}$ is independently halogen, $C_1$-$C_4$ alkyl or $C_1$-$C_4$ haloalkyl; or
$R^9$ and $R^{10}$ are taken together with two adjacent carbon atoms to form a 5-membered ring containing ring members selected from carbon atoms and two O atoms, and optionally substituted on carbon atom ring members with up to 2 halogen atoms;
$R^{11}$ is $C_1$-$C_4$ haloalkyl, $C_1$-$C_4$ haloalkoxy or $S(O)_w R^{22}$;
$R^{12}$ is halogen, $C_1$-$C_4$ alkyl or $C_1$-$C_4$ haloalkyl;
$R^{13}$ is H, $CH_3$ or $CH_2CF_3$;
each $R^{14b}$ is independently $C_1$-$C_4$ alkyl;
each $R^{15b}$ is independently $C_1$-$C_4$ alkyl;
each $R^{17}$, $R^{20}$ and $R^{22}$ is independently $C_1$-$C_4$ alkyl;
$R^{21}$ is $CF_3$; and
each q, u, w and x is independently 0 or 2.

3. The compound of claim 2 wherein
A is phenyl substituted with $R^3$;
$R^1$ is H, $C_1$-$C_4$ alkyl or $C_1$-$C_4$ haloalkyl;
$R^2$ is H, $C_1$-$C_4$ alkoxy, $C_1$-$C_4$ haloalkoxy, $C_1$-$C_4$ alkyl, $C_1$-$C_4$ haloalkyl, $C_3$-$C_4$ alkenyloxy, $C_3$-$C_4$ alkynyloxy, $C_2$-$C_6$ alkylcarbonyloxy, $C_1$-$C_4$ alkylamino or $C_2$-$C_4$ dialkylamino; or
$R^1$ and $R^2$ are taken together as $C_4$ alkylene;
J is selected from J-1 through J-14;
each $R^3$ is independently H, halogen or $C_1$-$C_4$ haloalkyl;
each $R^4$ is independently H, halogen, $C_1$-$C_4$ alkyl, $C_1$-$C_4$ haloalkyl;
$R^6$ is H, Cl or $CH_3$;
$R^7$ is H, OH or $OR^{14b}$;
$R^9$ is $CF_3$, $CH_2CF_3$, —$OCF_3$ or —$SCF_3$; and
each $R^{10}$ is independently Cl, F or $CH_3$.

4. The compound of claim 3 wherein
$R^1$ is H or $C_1$-$C_4$ alkyl;
$R^2$ is $C_1$-$C_4$ alkoxy, $C_1$-$C_4$ alkyl or $C_2$-$C_4$ dialkylamino;
Q is O;
J is selected from J-1 and J-2;
each $R^3$ is H, F, Cl, Br or $CF_3$;
each $R^4$ is independently H, F, Cl, Br, $CH_3$ or $CF_3$;
$R^9$ is $CF_3$; and
each $R^{10}$ is independently F.

5. The compound of claim 3 wherein
$R^1$ is H or $CH_3$;
$R^2$ is $C_1$-$C_4$ alkoxy;
Q is $C(R^6)(R^7)$;
$R^6$ is H, Cl or $CH_3$; and
$R^7$ is H or OH.

6. The compound of claim 2 wherein
A is phenyl substituted with $R^3$;
$R^1$ is H, $C_1$-$C_4$ alkyl or $C_1$-$C_4$ haloalkyl;
$R^2$ is H, $C_1$-$C_4$ alkoxy, $C_1$-$C_4$ haloalkoxy, $C_1$-$C_4$ alkyl, $C_1$-$C_4$ haloalkyl, $C_3$-$C_4$ alkenyloxy, $C_3$-$C_4$ alkynyloxy, $C_2$-$C_6$ alkylcarbonyloxy, $C_1$-$C_4$ alkylamino or $C_2$-$C_4$ dialkylamino; or
$R^1$ and $R^2$ are taken together as $C_4$ alkylene;
J is selected from J-15 through J-33;
$R^6$ is H, Cl or $CH_3$;
$R^7$ is H, OH or $OR^{14b}$;
$R^{11}$ is $CF_3$, $CH_2CF_3$, $-OCF_3$ or $-SCF_3$;
$R^{12}$ is Cl, $CH_3$ or $CF_3$;
$R^{13}$ is H or $CH_3$;
$R^{14b}$ is $CH_3$; and
$R^{15b}$ is $CH_3$.

7. The compound of claim 2 wherein
$R^1$ is H or $C_1$-$C_4$ alkyl;
$R^2$ is $C_1$-$C_4$ alkoxy, $C_1$-$C_4$ alkyl or $C_2$-$C_4$ dialkylamino;
Q is $C(R^6)(R^7)$;
J is selected from J-1 and J-2;
each $R^3$ is H, F, Cl, Br or $CF_3$;
each $R^4$ is independently H, F, Cl, Br, $CH_3$ or $CF_3$;
$R^6$ is H or $CH_3$;
$R^7$ is H or OH;
$R^9$ is $CF_3$; and
each $R^{10}$ is independently F.

8. The compound of claim 7 wherein
$R^1$ is H or $CH_3$;
$R^2$ is $C_1$-$C_4$ alkoxy;
$R^3$ is H, F or $CF_3$;
$R^6$ is H; and
$R^7$ is H or OH.

9. The compound of claim 1 selected from the group consisting of
2-(4-fluorophenyl)-5-methyl-6-[[2-(trifluoromethyl)-4-pyridinyl]methyl]-3(2H)-pyridazinone;
5-methyl-2-[4-(trifluoromethyl)phenyl]-6-[[2-(trifluoromethyl)-4-pyridinyl]methyl]-3 (2H)-pyridazinone;
4-methyl-2-[4-(trifluoromethyl)phenyl]-6-[[2-(trifluoromethyl)-4-pyridinyl]oxy]-3(2H)-pyridazinone;
2-(4-fluorophenyl)-5-methyl-6-[[2-(trifluoromethyl)-4-pyridinyl]oxy]-3(2H)-pyridazinone;
5-methoxy-2-[4-(trifluoromethyl)phenyl]-6-[[2-(trifluoromethyl)-4-pyridinyl]methyl]-3(2H)-pyridazinone;
2-(4-fluorophenyl)-5-methoxy-6-[[2-(trifluoromethyl)-4-pyridinyl]methyl]-3(2H)-pyridazinone;
5-ethoxy-2-(4-fluorophenyl)-6-[hydroxy[2-(trifluoromethyl)-4-pyridinyl]methyl]-3(2H)-pyridazinone; and
5-ethoxy-2-(4-fluorophenyl)-6-[[2-(trifluoromethyl)-4-pyridinyl]methyl]-3(2H)-pyridazinone.

10. A herbicidal composition comprising a compound of claim 1 and at least one component selected from the group consisting of surfactants, solid diluents and liquid diluents.

11. A herbicidal composition comprising a compound of claim 1, at least one additional active ingredient selected from the group consisting of other herbicides and herbicide safeners, and at least one component selected from the group consisting of surfactants, solid diluents and liquid diluents.

12. A herbicidal mixture comprising (a) a compound of claim 1, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, and (b16) herbicide safeners; and salts of compounds of (b1) through (b16).

* * * * *